(12) United States Patent
Babcook et al.

(10) Patent No.: US 11,208,497 B2
(45) Date of Patent: Dec. 28, 2021

(54) ANTIBODIES COMPRISING C-TERMINAL LIGHT CHAIN POLYPEPTIDE EXTENSIONS AND CONJUGATES AND METHODS OF USE THEREOF

(71) Applicant: ZYMEWORKS INC., Vancouver (CA)

(72) Inventors: John Babcook, Vancouver (CA); James R. Rich, Vancouver (CA); Jan Peter Bergqvist, Vancouver (CA); Stuart Daniel Barnscher, Vancouver (CA)

(73) Assignee: ZYMEWORKS INC.

( * ) Notice: Subject to any disclaimer, the term of this patent is extended or adjusted under 35 U.S.C. 154(b) by 0 days.

(21) Appl. No.: 15/107,884

(22) PCT Filed: Dec. 23, 2014

(86) PCT No.: PCT/CA2014/051263
§ 371 (c)(1),
(2) Date: Jun. 23, 2016

(87) PCT Pub. No.: WO2015/095972
PCT Pub. Date: Jul. 2, 2015

(65) Prior Publication Data
US 2017/0008970 A1    Jan. 12, 2017

Related U.S. Application Data

(60) Provisional application No. 61/920,425, filed on Dec. 23, 2013.

(51) Int. Cl.
| | | |
|---|---|---|
| *C07K 16/32* | (2006.01) | |
| *A61K 47/68* | (2017.01) | |
| *C07K 16/00* | (2006.01) | |
| *A61K 49/00* | (2006.01) | |
| *A61K 39/00* | (2006.01) | |

(52) U.S. Cl.
CPC ......... *C07K 16/32* (2013.01); *A61K 47/6835* (2017.08); *A61K 47/6851* (2017.08); *A61K 49/0039* (2013.01); *A61K 49/0058* (2013.01); *C07K 16/00* (2013.01); *A61K 2039/505* (2013.01); *C07K 2317/14* (2013.01); *C07K 2317/24* (2013.01); *C07K 2317/52* (2013.01); *C07K 2317/522* (2013.01); *C07K 2317/53* (2013.01); *C07K 2317/56* (2013.01); *C07K 2317/73* (2013.01); *C07K 2317/92* (2013.01)

(58) Field of Classification Search
CPC .... C07K 16/32; C07K 16/00; C07K 2317/24; C07K 2317/73; C07K 2317/522; C07K 2317/52; C07K 2317/53; C07K 2317/56; C07K 2317/92; A61K 47/6851; A61K 47/6835; A61K 49/0039; A61K 49/0058; A61K 2039/505; A61K 47/6803; A61K 39/395; A61P 43/00; A61P 35/00
See application file for complete search history.

(56) References Cited

U.S. PATENT DOCUMENTS

| | | | | |
|---|---|---|---|---|
| 6,165,476 A | * | 12/2000 | Strom | C07K 14/505 424/195.11 |
| 6,652,863 B1 | * | 11/2003 | Jordan | C07K 14/3153 424/133.1 |
| 2006/0099150 A1 | | 5/2006 | Houston et al. | |
| 2008/0153752 A1 | | 6/2008 | Takashima et al. | |
| 2009/0068202 A1 | * | 3/2009 | Chen | A61K 51/1027 424/173.1 |
| 2009/0148905 A1 | * | 6/2009 | Ashman | C07K 16/468 435/69.6 |
| 2009/0155275 A1 | | 6/2009 | Wu et al. | |
| 2011/0217302 A1 | * | 9/2011 | Odegard | C07K 16/2809 424/134.1 |
| 2012/0020966 A1 | | 1/2012 | Barbas, III | |
| 2012/0195879 A1 | * | 8/2012 | Walker | A61K 39/39591 424/130.1 |
| 2012/0308584 A1 | * | 12/2012 | Kim | C12Q 1/48 424/179.1 |

(Continued)

FOREIGN PATENT DOCUMENTS

| | | |
|---|---|---|
| RU | 2170589 C2 | 7/2001 |
| WO | WO 99/02711 A2 | 1/1999 |

(Continued)

OTHER PUBLICATIONS

Messerschmidt et al., Bioconjugate Chemistry 19: 362-369, 2008.*
Harlow et al in Antibodies a Laboratory Manual, 1988, Cold Spring harbor laboratory publication, Cold Spring Harbor, NY, pp. 626-629.*
Rudikoff et al., PNAS 79: 1979-1983, 1982.*
Stancovski et al., PNAS, 88: 8691-8695, 1991.*
Backstrom et al., Immunity 5: 437-447 (Year: 2002).*

(Continued)

*Primary Examiner* — Phuong Huynh
(74) *Attorney, Agent, or Firm* — Todd Lorenz; Eric John Zylstra

(57) ABSTRACT

The present disclosure provides light chain polypeptides that include a C-terminal extension, as well as antibodies and antibody conjugates containing such modified light chain polypeptides, where the C-terminal extension includes one or more cysteine residues. Conjugates that include an antibody of the present disclosure conjugated to an agent via the cysteine residue of the C-terminal amino acid extension are also provided. The present disclosure further provides nucleic acids encoding an antibody light chain polypeptide that includes a C-terminal amino acid extension including a cysteine residue. Pharmaceutical compositions including the antibodies or conjugates of the present disclosure are also provided, as are methods of making and use of the modified anti-bodies and conjugates of the present disclosure.

39 Claims, 50 Drawing Sheets
Specification includes a Sequence Listing.

(56) References Cited

U.S. PATENT DOCUMENTS

| | | | | |
|---|---|---|---|---|
| 2013/0011394 A1* | 1/2013 | Knoetgen | ............... | C12P 21/00 424/133.1 |
| 2014/0186350 A1 | 7/2014 | Ghosh et al. | | |
| 2016/0297854 A1 | 10/2016 | Ghosh et al. | | |

FOREIGN PATENT DOCUMENTS

| | | | | |
|---|---|---|---|---|
| WO | WO-9902711 A2 * | 1/1999 | ............. | A61P 35/02 |
| WO | WO 2005/000902 A1 | 1/2005 | | |
| WO | WO-2007103288 A2 * | 9/2007 | ......... | A61K 47/6811 |
| WO | WO-2007146968 A2 * | 12/2007 | ......... | C07K 16/2803 |
| WO | WO-2009026274 A1 * | 2/2009 | ......... | C07K 16/2875 |
| WO | WO 2009/088805 A2 | 7/2009 | | |
| WO | WO 2010/108153 A2 | 9/2010 | | |
| WO | WO 2012/059882 A2 | 5/2012 | | |
| WO | WO 2012/162561 A2 | 11/2012 | | |
| WO | WO-2012175508 A1 * | 12/2012 | ....... | C07K 14/70539 |
| WO | WO 2013/070565 A1 | 5/2013 | | |
| WO | WO 2013/096829 A2 | 6/2013 | | |
| WO | WO-2013128031 A1 * | 9/2013 | ............. | A61P 11/00 |
| WO | WO 2014/099997 A1 | 6/2014 | | |

OTHER PUBLICATIONS

Shen et al., "Conjugation site modulates the in vivo stability and therapeutic activity of antibody-drug conjugates," Nat. Biotech., vol. 30, pp. 184-189 (2012).

Goldmacher, V.S. and Kovtun, Y.V., "Antidoby-drug conjugates: using monoclonal antibodies for delivery of cytotoxic payloads to cancer cells," Therapeutic Delivery, vol. 2, No. 3, pp. 397-416 (2011).

Orcutt et al., "A modular IgG-scFv bispecific antibody topology," Protein Engineering, vol. 23, No. 4, pp. 221-228 (2009).

Shen, Y., et al., "Removal of a C-terminal serine residue proximal to the inter-chain disulfide bond of a human IgG1 lambda light chain mediates enhanced antibody stability and antibody dependent cell-mediated cytotoxicity," MAbs,vol. 5(3), pp. 418-431 (2013).

Spangler, J.B., et al., Triepitopic antibody fusions inhibit cetuximab-resistant BRAF and KRAS mutant tumors via EGFR signal repression. J Mol Biol, vol. 422(4), pp. 532-544 (2012).

Strop et al., "Location matters: site of conjugation modulates stability and pharmacokinetcis of antibody drug conjugates," Chemistry and Biology, vol. 20, No. 2, pp. 161-167 (2013).

Torrance et al., "Oriented immobilisation of engineered single-chain antibodies to develop biosensors for virus detection," J. Virol. Methods, vol. 134, No. 1-2, pp. 164-170 (2006).

PCT/CA2014/051263—IPRP issued Mar. 3, 2015.

Lambert, John M., "Drug-conjugated antibodies for the treatment of cancer," British J. of Clinical Pharm., vol. 76, No. 2, pp. 248-262 (2012).

Levary et al., "Protein-Protein Fusion Catalyzed by Sortase A," PLOS One, Public Library of Science, Vo. 6, No. 4, pp. e18342.1-e18342.6 (2011).

Royt, A., "Antibodies and dedicated cell receptors", Immunolgoy, Moscow, MIR, pp. 110-111 (2000).

Pakula et al., "Genetic analysis of protein stability and function," Annu. Rev. Genet., vol. 23, pp. 289-310 (1989).

Sirk et al., "Site-specific, Thiol-medicated Conjugation of Fluorescent Probes to Cysteine-modified Diabodies Targeting CD20 or HER2", Bioconjug. Chem., vol. 19(12), pp. 2527-2534 (2008).

Singer et al., Genes and genomes, Moscow, Mir, vol. 1, pp. 63-64 (1998).

Yakubke H.D. et al., Amino acids, peptides, proteins, Moscow, Mir, pp. 356-363 (1985).

English translation of Office Action dated Apr. 21, 2020 in Russian Patent Application No. 2016129724.

* cited by examiner

FIG. 4
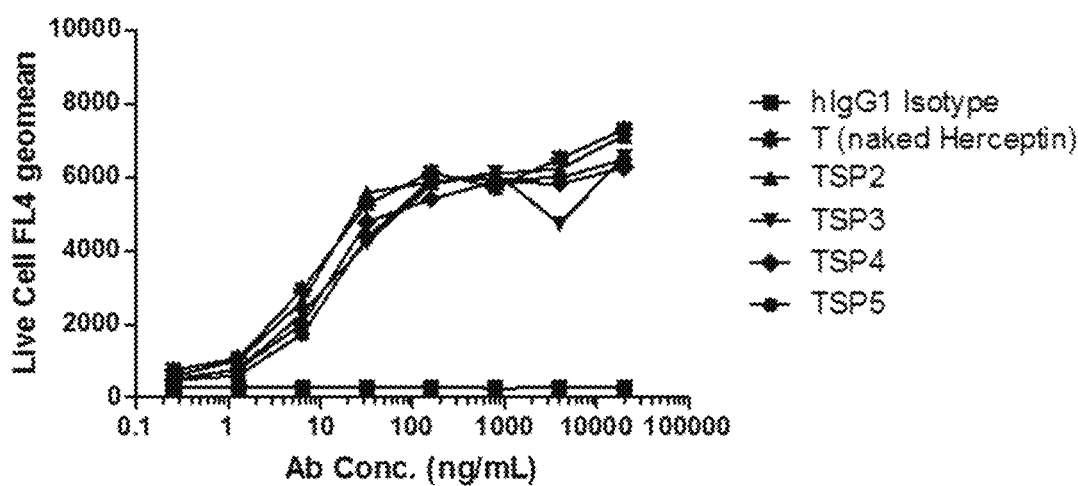
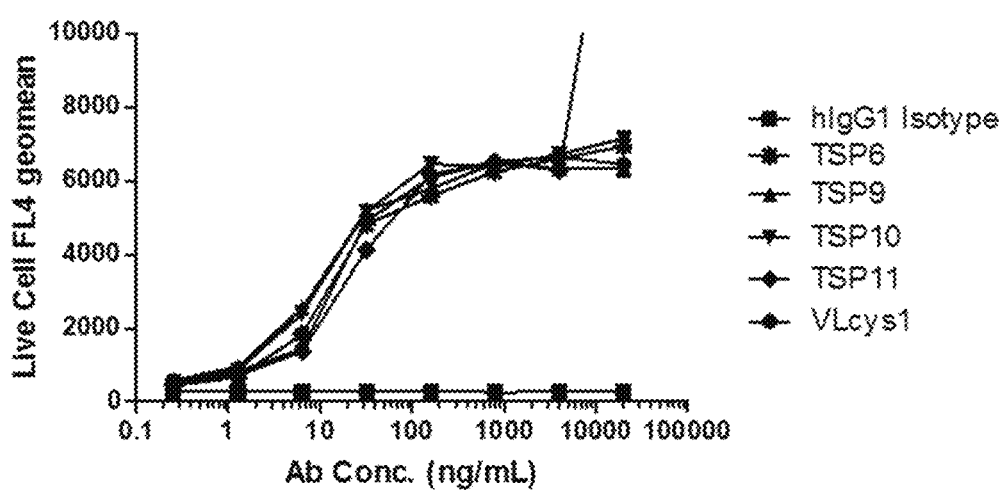

FIG. 63
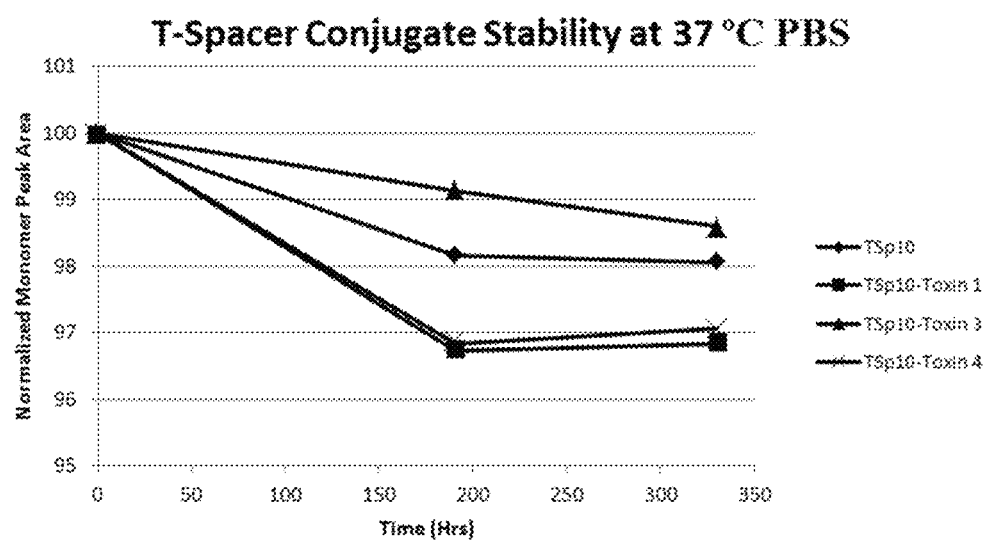
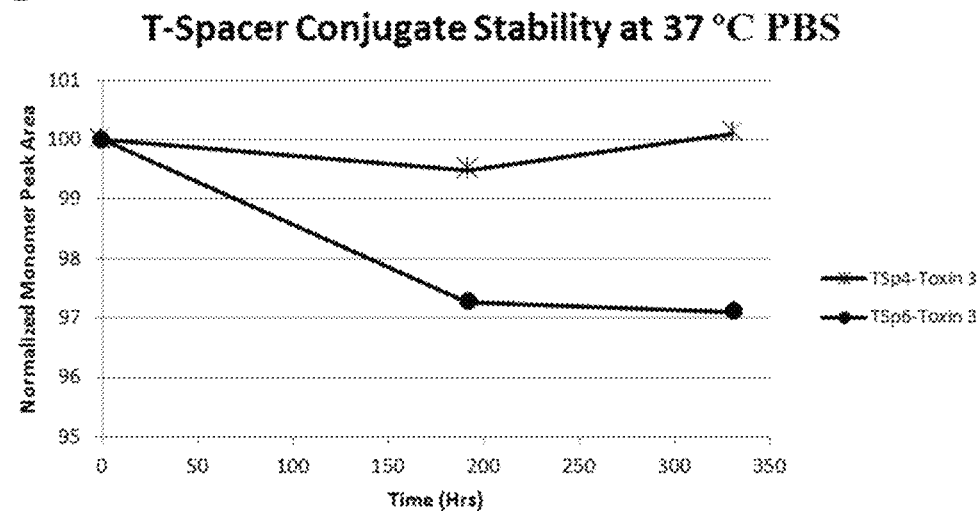

ANTIBODIES COMPRISING C-TERMINAL LIGHT CHAIN POLYPEPTIDE EXTENSIONS AND CONJUGATES AND METHODS OF USE THEREOF

CROSS-REFERENCE TO RELATED APPLICATION

Pursuant to 35 U.S.C. §119(e), this application claims priority to the filing date of U.S. Provisional Patent Application Ser. No. 61/920,425, filed Dec. 23, 2013, the disclosure of which is incorporated herein by reference.

INTRODUCTION

Significant advances have been made in recent years to develop therapeutic agents with improved selectivity for the cells underlying the etiology of the particular disease being treated. The antigen specificity of antibodies has been exploited to provide for antigen-specific delivery of a drug payload.

Such drug-bearing antibodies are referred to as antibody drug conjugates (ADCs). ADCs are generally composed of an antibody chemically or enzymatically coupled to a drug (e.g., a cytotoxic drug), often via a linker. ADCs are typically designed to be stable in circulation and to effect intracellular drug release following antigen-specific binding and, in some instances, internalization of the ADC. Because ADCs may be designed to deliver a "payload" (such as a cytotoxic drug) to the cellular target, the efficiency of target cell modulation by the agent (e.g., target cell killing) may be much greater in the context of an ADC as compared to the corresponding antibody or drug alone.

ADCs that provide for conjugation of a drug payload at selected site(s) in the antibody are of interest. for a number of reasons, including the desire for homogeneity of product in an antibody drug conjugate preparation. To this end, some groups have explored amino acid substitution at specific sites within antibodies in an attempt to facilitate site-specific payload attachment while maintaining antibody structure and function. For example, Shen et al., have systematically examined cysteine substitution at various positions within antibody heavy and light chains to reveal the impact of site selection on conjugate stability (e.g., Nat. Biotech., 30:184-189, 2012). Notably, these studies have revealed that solvent accessibility of the site of attachment on an antibody can negatively impact the stability of a resulting ADC.

Furthermore, modifications that negatively impact antibody stability, including light chain association with heavy chain, may compromise antibody affinity for antigen as well ADC stability, thereby increasing toxicity, reducing specificity and diminishing utility. Locating or creating sites amenable to payload attachment in a site-specific manner without significantly compromising antibody affinity or the stability of resultant ADCs is highly desired.

The antigen specificity of antibodies has also been exploited to provide diagnostic and imaging tools that incorporate labeled agents and recognize epitopes and/or cells that inform diagnostic or prognostic determinations and the course of therapy. Such diagnostic and prognostic tools rely on the affinity of tool antibodies for antigen detection and rely on the retention of labeled agents by tool antibodies for specific signaling. Accordingly, as with ADCs, locating or creating sites amenable to label attachment in a site-specific manner without compromising antibody affinity or the stability of resultant conjugates is highly desired.

SUMMARY

The present disclosure provides antibody light chain polypeptides that include a C-terminal amino acid extension, as well as antibodies and antibody conjugates containing such modified light chain polypeptides, where the C-terminal extension includes one or more cysteine residues. Conjugates that include an antibody of the present disclosure conjugated to an agent via the cysteine residue of the C-terminal amino acid extension are also provided. The present disclosure further provides nucleic acids encoding an antibody light chain polypeptide that includes a C-terminal amino acid extension including a cysteine residue. Pharmaceutical compositions including the antibodies or conjugates of the present disclosure are also provided, as are methods of making and use of the antibodies and conjugates of the present disclosure.

In certain aspects, the present disclosure provides an antibody including a light chain polypeptide that includes a C-terminal amino acid extension including a cysteine residue.

In some embodiments, the present disclosure provides an antibody that includes a light chain polypeptide including a C-terminal amino acid extension that includes a cysteine residue, where the C-terminal amino acid extension does not specifically bind antigen (e.g., the extension does not include an antigen-binding portion of an antibody or an antigen-binding portion of an antibody fragment).

In certain aspects, the present disclosure provides an antibody that includes at least one monoepitopic antigen-binding dimer, where the monoepitopic antigen-binding dimer includes a heavy chain polypeptide and a light chain polypeptide that includes a C-terminal amino acid extension, which extension includes a cysteine residue. Each of the two monoepitopic dimers may bind to the same epitope. In other aspects, each of the two monoepitopic dimers binds a different epitope.

According to certain embodiments, the C-terminal amino acid extension of any of the antibodies summarized above includes an amino acid spacer that does not include a cysteine residue. In certain aspects, the spacer is from 1 to 30 amino acids, from 3 to 20 amino acids, or from 4 to 17 amino acids. In certain embodiments, the spacer includes a glycine (G) residue and a serine (S) residue. For example, the spacer may consist of one or more glycine (G) residues and one or more serine (S) residues. Such a spacer optionally has the sequence GGGS. In certain embodiments, the extension includes endogenous human amino acid sequences or modified human amino acid sequences. These may include human antibody hinge region sequences, T-cell receptor sequences or other human sequences. In certain aspects, the extension may include extracellular protein amino acid sequences and/or amino acid sequences of extracellular domains of proteins present on a cell surface. In one embodiment, the extension includes an endogenous human amino acid sequence that includes one or more naturally occurring cysteine residues. These may include human antibody hinge region sequences, T-cell receptor sequences or other human protein cysteine containing sequences. In certain aspects, the extension may include extracellular protein amino acid sequences and/or amino acid sequences of extracellular domains of proteins present on a cell surface. In one embodiment, the extension includes a modified human amino acid sequence wherein one or more cysteines has been introduced into the endogenous human amino acid sequence by insertion or substitution.

The C-terminal amino acid extension of the antibodies of the present disclosure may include more than one spacer. For example, the C-terminal amino acid extension may include from 2 to 10 spacers. The spacers may have the same amino acid sequence. In other aspects, the amino acid sequence of at least two of the spacers is different. According to certain embodiments, a cysteine is present between each of the spacers. Alternatively, at least two of the spacers may be contiguous, e.g., at least two of the spacers in the C-terminal amino acid extension do not include any amino acids (e.g., any cysteines) between the spacers. In one embodiment, the C-terminal amino acid extension terminates in a cysteine.

In certain aspects, a cysteine within the C-terminal amino acid extension of an antibody of the present disclosure includes a reduced sulfhydryl group. According to certain embodiments, the antibody includes an agent conjugated to the cysteine residue of the C-terminal amino acid extension. In one embodiment, the agent is directly conjugated to the cysteine residue of the C-terminal amino acid extension. In one embodiment, the agent is indirectly conjugated to the cysteine residue of the C-terminal amino acid extension via a linker. In one embodiment, the agent is preferentially conjugated to the cysteine of the C-terminal amino acid extension of the light chain over a cysteine residue outside the C-terminal amino acid extension. In one embodiment, the agent is exclusively conjugated to the antibody via the cysteine of the C-terminal amino acid extension of the light chain of the antibody. In certain aspects, the agent is a therapeutic agent (e.g., a cytotoxic agent) or a labeling agent (e.g., an in vivo imaging agent). According to certain embodiments, the C-terminal amino acid extension includes two or more cysteines each conjugated to an agent independently selected from a therapeutic agent and a labeling agent.

In one embodiment, two or more agents are independently directly or indirectly conjugated to two or more cysteine residues of the C-terminal amino acid extension. In one embodiment, the agents are preferentially conjugated to the cysteines of the C-terminal amino acid extension of the light chain over a cysteine residue outside the C-terminal amino acid extension. In one embodiment, the agents are exclusively conjugated to the antibody via the cysteines of the C-terminal amino acid extension of the light chain of the antibody.

Antibodies of the present disclosure may be an antibody or binding fragment thereof. For example, the antibody may be an IgG, Fab, F(ab')2, Fab', Fv, ScFv, bispecific antibody, or the like.

Also provided by the present disclosure are conjugates. According to some embodiments, the conjugates include an antibody including a light chain polypeptide that includes a C-terminal amino acid extension including a cysteine residue.

In certain aspects, the conjugates include an antibody that includes a light chain polypeptide including a C-terminal amino acid extension that includes a cysteine residue, where the C-terminal amino acid extension does not specifically bind antigen (e.g., the extension does not include an antigen-binding portion of an antibody or an antigen-binding portion of an antibody fragment).

In some embodiments, the conjugates include an antibody that includes at least one monoepitopic antigen-binding dimer, where the monoepitopic antigen-binding dimer includes a heavy chain polypeptide and a light chain polypeptide that includes a C-terminal amino acid extension, which extension includes a cysteine residue. The antibodies of such conjugates may include two monoepitopic antigen-binding dimers. Each of the two monoepitopic dimers may bind to the same epitope. In other aspects, each of the two monoepitopic dimers binds a different epitope.

The conjugates further include an agent conjugated to the antibody via the cysteine residue of the C-terminal amino acid extension. The antibody and agent of the conjugates of the present disclosure may have any of the antibody and agent features summarized above or described in the detailed description and examples section hereinbelow, and may be conjugated using the conjugation strategies described herein or any other suitable strategy that provides for the same conjugation results.

Aspects of the present disclosure include nucleic acids that encode all or a portion of the antibodies of the present disclosure. For example, provided is a nucleic acid that encodes an antibody light chain polypeptide including a C-terminal amino acid extension including a cysteine residue. The C-terminal amino acid extension may include any of the features summarized above with respect to the antibodies of the present disclosure, and as described in the detailed description and examples section hereinbelow. Vectors that include such nucleic acids, and host cells (e.g., prokaryotic or eukaryotic host cells) that include the nucleic acids and vectors of the present disclosure are also provided.

In certain aspects, the present disclosure provides pharmaceutical compositions. According to certain embodiments, the pharmaceutical compositions include any of the antibodies or conjugates summarized above with respect to the antibodies and conjugates of the present disclosure, and as described in the detailed description and examples section hereinbelow. Also provided are methods that include administering to a patient in need thereof a therapeutically effective amount of any of the pharmaceutical compositions, the antibodies or conjugates summarized above with respect to the antibodies and conjugates of the present disclosure, and as described in the detailed description and examples section hereinbelow.

Methods of making a light chain of an antibody are also provided. Such methods include expressing in a host cell a nucleic acid encoding an antibody light chain polypeptide including a C-terminal amino acid extension that includes a cysteine residue. In certain aspects, the methods further include reducing the sulfhydryl group of the cysteine residue in the C-terminal amino acid extension. In one embodiment, the methods comprise the preferential (or "biased") reduction of the sulfhydryl group of the cysteine residue in the C-terminal amino acid extension over the reduction of cysteine residues outside the C-terminal amino acid extension. In one embodiment, the methods comprise the exclusive reduction of the sulfhydryl group of the cysteine residue in the C-terminal amino acid extension over the reduction of cysteine residues outside the C-terminal amino acid extension.

In certain aspects, the C-terminal amino acid extension includes two or more cysteine residues. In certain aspects, the methods further include reducing the sulfhydryl groups of the cysteine residues in the C-terminal amino acid extension. In one embodiment, the methods comprise the preferential (or "biased") reduction of the sulfhydryl groups of the cysteine residues in the C-terminal amino acid extension over the reduction of cysteine residues outside the C-terminal amino acid extension. In one embodiment, the methods comprise the exclusive reduction of the sulfhydryl groups of the cysteine residues in the C-terminal amino acid extension over the reduction of cysteine residues outside the C-terminal amino acid extension.

Aspects of the present disclosure include methods of making antibody conjugates. The methods include conjugating an agent to an antibody including a light chain polypeptide that includes a C-terminal amino acid extension including a cysteine residue, where the agent is conjugated to the cysteine residue of the C-terminal amino acid extension. The methods of making antibody conjugates may further include reducing the sulfhydryl group of the cysteine in the C-terminal amino acid extension prior to conjugating the agent to the antibody. In certain aspects, the conjugating includes crosslinking the agent to the reduced sulfhydryl group using maleimide reaction chemistry, haloacetyl reaction chemistry, vinyl sulfone reaction chemistry or pyridyl disulfide reaction chemistry. According to certain aspects, the agent that is conjugated to the cysteine residue of the C-terminal amino acid extension is a therapeutic agent or a labeling agent. In one embodiment, the agent is conjugated to the cysteine residue of the C-terminal amino acid extension preferentially over cysteine residues outside the C-terminal amino acid extension. In one embodiment, the agent is conjugated to the cysteine residue of the C-terminal amino acid extension and not to any cysteine residues outside the C-terminal amino acid extension.

In certain aspects, the C-terminal amino acid extension includes two or more cysteine residues, and two or more agents are conjugated to the cysteine residues of the C-terminal amino acid extension. The methods of making such antibody conjugates may further include reducing the sulfhydryl groups of the cysteines in the C-terminal amino acid extension prior to conjugating the agents to the antibody. In certain aspects, the conjugating includes crosslinking the agents to the reduced sulfhydryl groups using maleimide reaction chemistry, haloacetyl reaction chemistry, vinyl sulfone reaction chemistry or pyridyl disulfide reaction chemistry. According to certain aspects, the agents that are conjugated to the cysteine residues of the C-terminal amino acid extensions are therapeutic agents and/or labeling agents. In one embodiment, the agents are conjugated to the cysteine residues of the C-terminal amino acid extension preferentially over cysteine residues outside the C-terminal amino acid extension. In one embodiment, the agents are conjugated to the cysteine residues of the C-terminal amino acid extension and not to any cysteine residues outside the C-terminal amino acid extension.

BRIEF DESCRIPTION OF THE FIGURES

FIG. 4, Panels A and B show antibody binding data for unconjugated antibodies according to certain embodiments of the present disclosure.

Figures 30, 31:
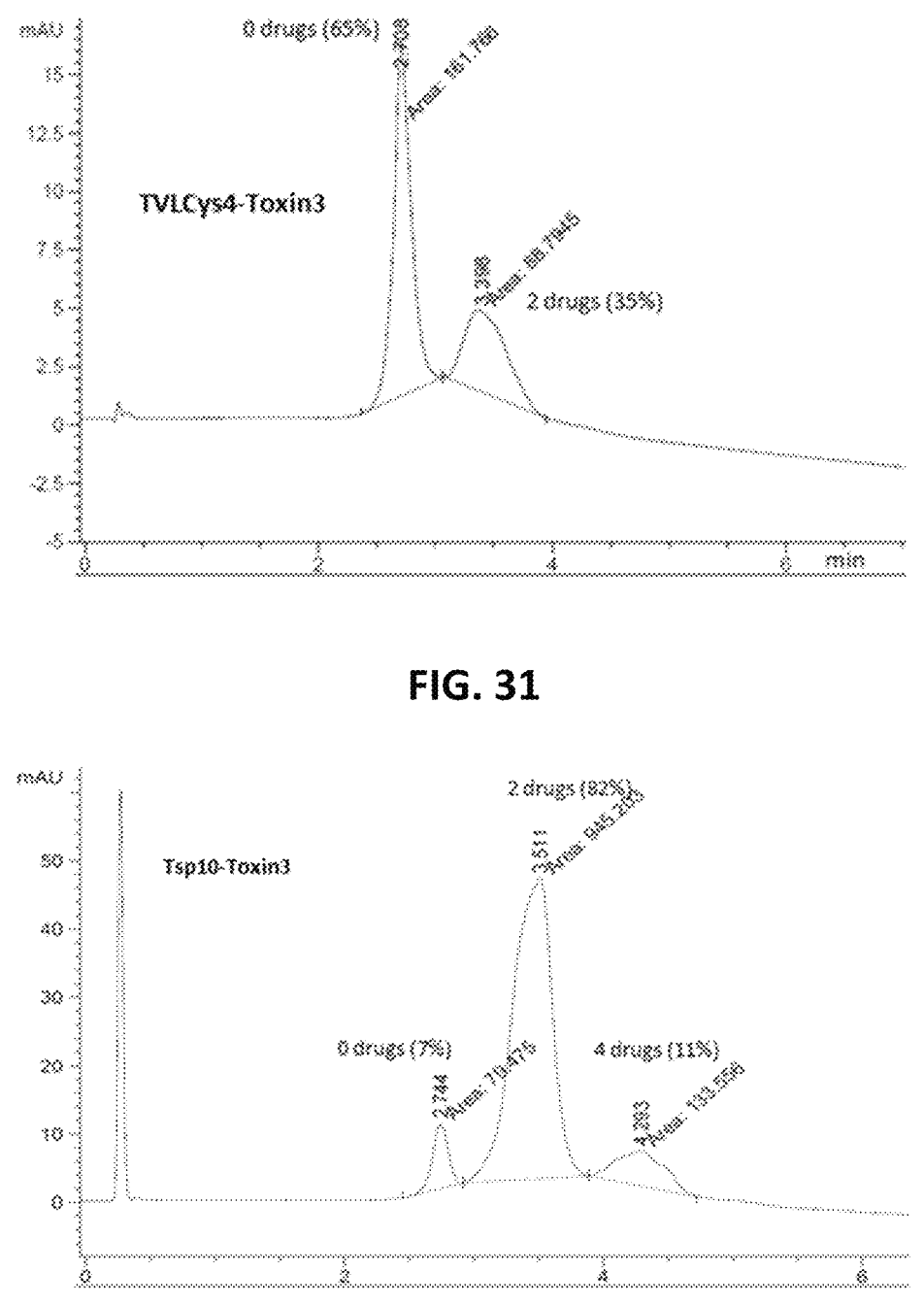

FIG. 30 shows an HIC chromatograph of conjugation reaction products for TVLCys4-Toxin3. The average drug loading value was 0.70.

FIG. 31 shows an HIC chromatograph of conjugation reaction products for Tsp10-Toxin 3 (larger scale). The average drug loading value was 2.12.

FIG. 63 provides stability data for trastuzumab light chain extension antibody drug conjugates as determined using a thermal stability assay.

DETAILED DESCRIPTION

Figure 1:
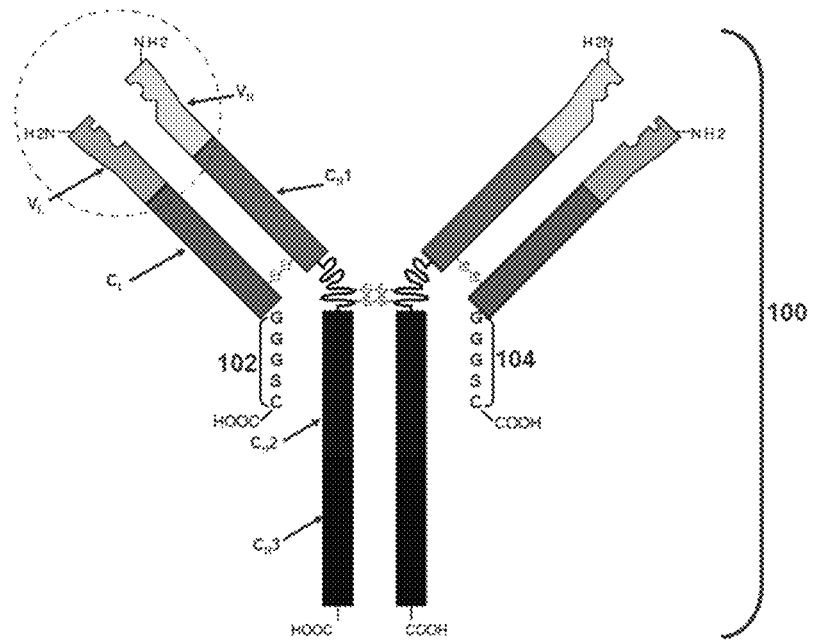
FIG. 1 is a schematic illustration of an antibody that includes a C-terminal light chain extension according to one embodiment of the present disclosure.

Investigators evaluating the structural differences between antibody light chains and the impact thereof on antibody stability have predicted that amino acid additions to the C-terminus of antibody light chains will have a destabilizing effect (Shen et al., mAbs 5:3, 418-431, 2013). Indeed others have reported that the linkage of scFvs and single domain protein scaffolds to the C terminus of IgG light chains to generate multi-specific antibodies destabilizes the light chain-heavy chain disulfides, leading to an increase of partially assembled IgG fusion molecules (Orcutt et al., Prot. Eng. Des. Sel, 23:221-228, 2010; Spangler et al., J Mol Biol, 422:532-544, 2012). In addition, it has been reported that solvent accessibility of the site of payload attachment can negatively impact ADC stability (Shen et al., Nat. Biotech., 30:184-189, 2012). Contrary to these reports, the present invention derives in part from the surprising finding that a C-terminal amino acid extension (also referred to herein as a "payload adaptor") covalently linked to the C-terminus of an antibody light chain as an extension thereof can provide a stable point of attachment for payload, resulting in antibody payload conjugates that are stable and retain affinity for antigen.

Accordingly, the present disclosure provides antibody light chain polypeptides that include a C-terminal amino acid extension, as well as antibodies and antibody conjugates containing such modified light chain polypeptides, where the C-terminal extension includes one or more cysteine residues. Conjugates that include an antibody of the present disclosure conjugated to an agent via a cysteine residue of the C-terminal amino acid extension are also provided. The present disclosure further provides nucleic acids encoding an antibody light chain polypeptide that includes a C-terminal amino acid extension including a cysteine residue. Pharmaceutical compositions including the antibodies or conjugates of the present disclosure are also provided, as are methods of making and use of the modified antibodies and conjugates of the present disclosure.

Before the antibodies, conjugates, nucleic acids, pharmaceutical compositions and methods of the present disclosure are described in greater detail, it is to be understood that such aspects of the present disclosure are not limited to particular embodiments described, as such may, of course, vary. It is also to be understood that the terminology used herein is for the purpose of describing particular embodiments only, and is not intended to be limiting, since the scope of the antibodies, conjugates, nucleic acids, pharmaceutical compositions and methods of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the antibodies, conjugates, nucleic acids, pharmaceutical compositions and methods. The upper and lower limits of these smaller ranges may independently be included in the smaller ranges and are also encompassed within the antibodies, conjugates, nucleic acids, pharmaceutical compositions and methods, subject to any specifically excluded limit in the stated range. Where the stated range includes one or both of the limits, ranges excluding either or both of those included limits are also included in the antibodies, conjugates, nucleic acids, pharmaceutical compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the antibodies, conjugates, nucleic acids, pharmaceutical compositions and methods belong. Although any antibodies, conjugates, nucleic acids, pharmaceutical compositions and methods similar or equivalent to those described herein can also be used in the practice or testing of the antibodies, conjugates, nucleic acids, pharmaceutical compositions and methods, representative illustrative antibodies, conjugates, nucleic acids, pharmaceutical compositions and methods are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. For example, as used herein, a C-terminal amino acid extension that "includes a cysteine", or is described as "including a cysteine", may contain multiple cysteine residues (i.e., the extension includes at least one cysteine). It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the antibodies, conjugates, nucleic acids, pharmaceutical compositions and methods, which may be, for clarity, described in the context of separate embodiments, may also be provided in combination in a single embodiment. Conversely, various features of the antibodies, conjugates, nucleic acids, pharmaceutical compositions and methods, which may be, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable antibodies, conjugates, nucleic acids, pharmaceutical compositions and methods. In addition, all sub-combinations listed in the embodiments describing such variables are also specifically embraced by the present antibodies, conjugates, nucleic acids, pharmaceutical compositions and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present antibodies, conjugates, nucleic acids, pharmaceutical compositions and methods. Any recited method can be carried out in the order of events recited or in any other order which is logically possible.

DEFINITIONS

The terms "antibody" and "immunoglobulin" include antibodies or immunoglobulins of any isotype, whole antibodies (e.g., antibodies composed of a tetramer which in turn is composed of two heterodimers of a heavy and light chain polypeptide, including whole IgG, IgA, IgD, IgE, or IgM antibodies); half antibodies (e.g., antibodies that include a single dimer of a heavy and light chain polypeptide); antibody fragments (e.g., fragments of whole antibodies, such as fragments of IgG, IgA, IgD, IgE, or IgM antibodies) which retain specific binding to an antigen of interest, including, but not limited to Fab, F(ab')2, Fab', Fv, scFv, bispecific antibodies and diabodies; chimeric antibodies; monoclonal antibodies; humanized antibodies (e.g., humanized monoclonal antibodies, or humanized antibody fragments); or fully human antibodies (an antibody that comprises human immunoglobulin protein sequences only). Also included are human monoclonal antibodies that possess somatic mutations and/or N- or P-nucleotide additions and deletions as a result of V-D-J rearrangement. Also included are human antibodies to which synthetic sequences have been inserted into the CDRs (see, e.g., Miersch S & Sidhu S S (2012) Synthetic antibodies: concepts, potential and practical considerations. *Methods* 57(4):486-98; and Knappik et al. (2000) Fully synthetic human combinatorial antibody libraries (HuCAL) based on modular consensus frameworks and CDRs randomized with trinucleotides. *J. Mol. Biol.* 296(1):57-86). In certain aspects, an antibody of the present disclosure is selected from an IgG (e.g., an IgG1, IgG2, IgG3 or IgG4 antibody), Fab, F(ab')2, and Fab'.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Fv" comprises the minimum antibody fragment which contains a complete antigen-recognition and antigen-binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "sFv" antibody fragments comprise the $V_H$ and $V_L$ domains of an antibody, where these domains are present in a single polypeptide chain. In some embodiments, the Fv polypeptide further comprises a polypeptide linker between the $V_H$ and $V_L$ domains, which enables the sFv to form the desired structure for antigen binding.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites.

A "light chain polypeptide" as used herein refers to a polypeptide having at least an antibody light chain variable region ($V_L$). A light chain polypeptide may include a partial or full-length antibody light chain constant region ($C_L$). A "full-length light chain polypeptide" includes a full-length light chain variable region ($V_L$) and a full-length light chain constant region ($C_L$). The light chain polypeptide may be from any vertebrate species (e.g., mammalian, e.g., human, rodent, and the like).

A "heavy chain polypeptide" or "heavy chain" as used herein refers to a polypeptide having at least an antibody heavy chain variable region ($V_H$). A heavy chain polypeptide may include a partial or full-length antibody heavy chain constant region ($C_H$) comprising CH1, CH2 and CH3 domains. A "full-length heavy chain polypeptide" includes a full-length heavy chain variable region ($V_L$) and a full-length heavy chain constant region ($C_H$). Encompassed are heavy chain polypeptides of antibodies (immunoglobulins) from any vertebrate species (e.g., mammalian, e.g., rodent, human, and the like), and any class of immunoglobulin. Heavy chain polypeptides, and antibodies containing such heavy chain polypeptides, are categorized into classes based on the amino acid sequence of the constant domain of the heavy chain polypeptide. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2.

The term "recombinant" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences, including, for example, in-vitro translation technology (see, e.g., Yin et al. (2012) Aglycosylated antibodies and antibody fragments produced in a scalable in vitro transcription-translation system, *Landes Bioscience*, Volume 4, Issue 2). Such recombinant antibodies include humanized, CDR grafted, chimeric, deimmunized, and in vitro generated antibodies; and can optionally include constant regions derived from human germline immunoglobulin sequences.

The term "humanized antibody" refers to immunoglobulins, half antibodies, immunoglobulin chains (e.g., a light chain polypeptide) or fragments thereof (such as Fv, scFv, Fab, Fab', F(ab')2 or other antigen-binding subsequences of antibodies) which contain minimal sequence derived from non-human immunoglobulin. The humanized antibodies may be human immunoglobulins (recipient antibody) in which residues from a complementary determining region (CDR) of the recipient are replaced by residues from a CDR of a non-human species (donor antibody) such as mouse, rat, lama, camel or rabbit having the desired specificity, affinity and capacity. In some instances, Fv framework residues of the human immunoglobulin are replaced by corresponding non-human residues. Furthermore, a humanized antibody may comprise residues which are found neither in the recipient antibody nor in the imported CDR or framework sequences.

Human light chain polypeptides are typically classified as kappa and lambda light chains. Furthermore, human heavy chain polypeptides are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids.

By "treating," "treat," or "treatment" is meant alleviating or abrogating a disease or disorder and/or at least one of its attendant symptoms. As used herein, to "alleviate" a disease or disorder means reducing the severity and/or occurrence frequency of the symptoms of the disease or disorder. It will be understood that references herein to "treating," "treat," or "treatment" include references to curative, palliative and prophylactic treatment.

By "therapeutically effective amount" or "efficacious amount" is meant a dosage sufficient to produce a desired result, e.g., an amount sufficient to effect beneficial or desired therapeutic (including preventative) results, such as a reduction in a symptom of a disease (e.g., cancer or any other disease of interest), as compared to a control. The "therapeutically effective amount" will vary depending on the antibody or conjugate, the disease and its severity, and the age, weight, etc., of the patient to be treated.

Light Chain Polypeptides Having a C-Terminal Extension ("Payload Adaptor")

In one aspect, the present disclosure provides payload adaptors (also referred to herein as a "C-terminal amino acid extension" or "C-terminal extension") for the attachment of payloads to antibodies, as well as antibodies comprising such payload adaptors.

The payload adaptors of the present disclosure are protein modules that serve as substrates for covalent attachment of payloads, with each payload adaptor constituting a C-terminus extension of an antibody light chain and thereby linking one or more payloads to an antibody. The payload adaptors comprise at least one cysteine residue for payload attachment.

Payload adaptors of the present disclosure are capable of being expressed as C-terminus extensions of antibody light chains and are capable of covalent conjugation to a wide variety of payloads with the use of appropriate chemistry such that the antibodies comprising payloads and payload adaptors exhibit stability and retain affinity for antigen.

In one embodiment, an antibody comprising a payload adaptor of the present disclosures does not comprise a cysteine substitution within its native antibody sequence, which might otherwise be introduced to provide a compensatory disulfide bond accommodating addition of a polypeptide to the C-terminus end of a light chain. Thus, in one embodiment, an antibody comprising a payload adaptor of the present disclosures contains all cysteine residues that are present in the parent antibody. In one embodiment, the payload adaptor comprises multiple cysteine residues that do not form an intramolecular disulfide bond or a disulfide bond with another payload adaptor.

In one embodiment, a payload adaptor does not specifically bind antigen. In one embodiment, the payload adaptor does not contribute an epitope binding activity to the antibodies or antibody conjugates of the invention. In this embodiment, antigen binding by the antibodies and antibody conjugates of the present disclosure is determined by elements other than the payload adaptors. In one embodiment, a payload adaptor does not contain a ligand binding domain of a growth factor receptor, such as an EGF receptor). In another embodiment, the payload adaptor does not contain a ligand of a growth factor receptor (e.g., does not contain a ligand of an EGF receptor).

More particularly, as summarized above, the present disclosure provides light chain polypeptides having a C-terminal extension having one or more cysteine residues, and antibodies having at least one of such modified light chain polypeptides. The light chain polypeptide having the C-terminal extension can contain an amino acid sequence of a light chain polypeptide of any type (e.g., a lambda (λ) or kappa (κ) light chain polypeptide) and can contain amino acid sequences of a light chain polypeptide of any origin of interest, e.g., any vertebrate species (e.g., mammalian, e.g., rodent, human, and the like).

The term "C-terminal light chain polypeptide extension", "C-terminal light chain amino acid extension", "C-terminal extension", "payload adaptor", and equivalents thereof, is used herein to refer to an amino acid (e.g., a cysteine) or a contiguous stretch of two or more amino acids located C-terminal to the residue of the light chain polypeptide that would otherwise constitute the C-terminal residue in a parental light chain polypeptide absent the extension.

In certain aspects, the parental light chain polypeptide only includes a light chain variable region ($V_L$) (e.g., the parental antibody may be an ScFv), such that the extension is C-terminal to (e.g., extends from) the residue that would otherwise constitute the C-terminus of a $V_L$ in a parental light chain polypeptide. In other aspects, the parental light chain polypeptide includes a light chain variable region ($V_L$) and a partial light chain constant region ($C_L$), such that the extension is C-terminal to (e.g., extends from) the residue that would otherwise constitute the C-terminus of a partial $C_L$ in a parental light chain polypeptide.

According to certain embodiments, the parental light chain polypeptide is a full-length light chain polypeptide that includes a full-length light chain variable region ($V_L$) and a full-length light chain constant region ($C_L$), such that the extension is C-terminal to (e.g., extends from) the residue that would otherwise constitute the C-terminus of a full-length $C_L$ in a parental light chain polypeptide. According to one embodiment, the N-terminal portion of the extension includes at least a portion of a sequence that would otherwise be present in a full-length parental light chain polypeptide, such that extending the C-terminus of the parental light chain polypeptide includes "adding back" parental sequence as part of the "extension."

According to some embodiments, the parental light chain polypeptide includes a deletion of the terminal cysteine normally present at the C-terminus of a full-length wild-type light chain polypeptide, such that the light chain extension is C-terminal to (e.g., extends from) the residue immediately N-terminal to the position in which the C-terminal cysteine is deleted. In one embodiment, the parental light chain polypeptide includes a substitution of the terminal cysteine normally present at the C-terminus of a full-length wild-type light chain polypeptide.

In certain aspects, the parental antibody has a truncated heavy chain polypeptide, e.g., a heavy chain polypeptide that only includes a heavy chain variable region ($V_H$), or a heavy chain polypeptide that includes a heavy chain variable region ($V_H$) and a portion of heavy chain constant region ($C_H$). According to these aspects, the C-terminal light chain polypeptide extension may comprise native (e.g., wild-type) light chain polypeptide sequence unpaired with heavy chain polypeptide sequence (due to the truncation). According to one embodiment, such a C-terminal light chain polypeptide extension may further include one or more non-native amino acids (e.g., one or more cysteines not present in the parental light chain polypeptide), which in certain aspects may be a non-native sequence of two or more amino acids.

In certain aspects, the present disclosure provides an antibody including a light chain polypeptide that includes a C-terminal amino acid extension including a cysteine residue.

In some embodiments, the present disclosure provides an antibody that includes a light chain polypeptide including a C-terminal amino acid extension that includes a cysteine residue, which C-terminal amino acid extension does not specifically bind antigen (e.g., the extension does not include an antigen-binding portion of an antibody or an antigen-binding portion of an antibody fragment).

In certain aspects, the present disclosure provides an antibody that includes at least one monoepitopic antigen-binding dimer, where the monoepitopic antigen-binding dimer includes a heavy chain polypeptide and a light chain polypeptide that includes a C-terminal amino acid extension, which extension includes a cysteine residue. Each of the two monoepitopic dimers may bind to the same epitope. In other aspects, each of the two monoepitopic dimers binds a different epitope.

"Monoepitopic antigen-binding domain" as used herein indicates an antigen-binding domain formed by interaction of the CDRs of a heavy chain polypeptide and the CDRs of a light chain polypeptide. Monoepitopic antigen-binding domains" can be defined by, for example, a dimer comprising a heavy chain polypeptide and a light chain polypeptide, or, in the case of a single chain antibody (ScFv) a monomeric fusion protein comprising a heavy chain polypeptide and a light chain polypeptide. Thus, in a monoepitopic antigen-binding domain comprising a light chain C-terminal amino acid extension, the amino acid extension of the light chain polypeptide does not specifically bind antigen. Antibodies of the present disclosure include antibodies comprising the same or different monoepitopic antigen-binding dimer. For example, an antibody comprising a dimer of heterodimers (i.e., a tetramer) may include: 1) a first monoepitopic antigen-binding domain comprising a heavy chain polypeptide and a light chain polypeptide, and a second monoepitopic antigen-binding domain comprising a heavy chain polypeptide and a light chain polypeptide, wherein one or both of the light chain polypeptides comprises a C-terminal amino acid extension, and wherein the first and second monoepitopic antigen-binding domains bind the same epitope; or 2) first and second monoepitopic antigen binding domains, wherein one or both of the light chain polypeptides of the domains comprises a C-terminal amino acid extension, where the antigen-binding region of the first monoepitopic antigen-binding domain binds a different epitope as that bound by the second monoepitopic antigen-binding domain.

The C-terminal extension may be any desired length. According to certain embodiments, the extension is from 1 to 200 amino acids, from 1 to 150 amino acids, from 1 to 100 amino acids, from 1 to 75 amino acids, from 1 to 50 amino acids, from 1 to 25 amino acids, from 1 to 20 amino acids, from 1 to 15 amino acids, from 1 to 10 amino acids, or from 1 to 5 amino acids in length, and may be from 5 to 200 amino acids, from 5 to 150 amino acids, from 5 to 100 amino acids, from 5 to 75 amino acids, from 5 to 50 amino acids, from 5 to 25 amino acids, from 5 to 20 amino acids, from 5 to 15 amino acids, or from 5 to 10 amino acids in length. In certain aspects, the extension is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids in length.

The C-terminal extension can contain any desired number of cysteines, e.g., 1, 2, 3, 4, 5, 6, 7, 8, 9, 10, 11, 12, 13, 14, 15, 16, 17, 18, 19 or 20 cysteines. In some embodiments, the C-terminal extension contains at least 2, 3, 4, 5, or more cysteines. In some embodiments the C-terminal extension contains no more than 2, 3, 4, 5, 6, 7, 8, 9 or 10 cysteines. In certain aspects, the extension includes from 1 to 5 cysteines, from 6 to 10 cysteines, from 11 to 15 cysteines, or from 16 to 20 cysteines.

According to certain embodiments, the C-terminal extension includes two or more contiguous cysteines. For example, the extension may include two adjacent cysteines having non-cysteine-containing spacer sequences N-terminal and C-terminal to the two adjacent cysteines. Having contiguous cysteines (e.g., two adjacent cysteines) in the C-terminal extension finds use, e.g., when the conjugation or labeling strategy includes metal chelation, when the conjugation or labeling strategy involves "bridging" (e.g., as is the case with certain dihalo-maleimide conjugation chemistries, and the like). As such, in certain aspects, the present disclosure provides conjugates and methods of making the same in which the agent (e.g., a drug or labeling agent) is attached to multiple contiguous cysteines (e.g., 2 adjacent cysteines), either directly or through one or more linkers.

In one embodiment, the C-terminal extension includes an N-terminal cysteine that when taken together with the parental light chain terminal cysteine provides two contiguous cysteines that find use as described above.

In certain aspects, the present disclosure provides conjugates and methods of making the same in which the agent (e.g., a drug or labeling agent) is attached to multiple non-contiguous cysteines, either directly or through one or more linkers.

In some embodiments, the cysteines of the C-terminal extension are separated by one or more spacers, such that the cysteines are not contiguous residues of the C-terminal extension. By "spacer" is meant one or more consecutive non-cysteine amino acids disposed between two cysteine residues in the extension; between what would otherwise constitute the C-terminal residue of the light chain polypeptide, or fragment thereof containing a light chain variable region and at least a portion of a light chain constant region, and the first cysteine residue in the C-terminal extension; and/or optionally one or more consecutive non-cysteine amino acids disposed C-terminal to the most C-terminal cysteine in the extension. Any number of spacers may be provided in the C-terminal extension. According to certain embodiments, the C-terminal extension can include from 1 to 50 spacers, from 1 to 40 spacers, from 1 to 30 spacers, from 1 to 20 spacers, from 1 to 10 spacers (e.g., from 2 to 10 spacers), or 1, 2, 3, 4, 5, 6, 7, 8, 9, or 10 spacers.

When the C-terminal extension includes 2 or more spacers, each of the spacers may have the same amino acid sequence. Alternatively, when the extension includes 2 or more spacers, the amino acid sequence of at least two of the spacers may be different. When the extension includes multiple spacers, a cysteine may be present between each of the spacers. In other aspects, when the extension includes multiple spacers, at least two of the spacers are contiguous, e.g., the spacers are not separated by one or more cysteine residues.

The spacer may include any of the 20 non-cysteine, naturally-occurring, genetically encodable amino acids (alanine (A), arginine (R), asparagine (N), aspartic acid (D), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y), and/or valine (V)), or variants thereof (e.g., variants that arise as a result of post-translation modification), naturally occurring non-encodable or non-natural amino acids, and may be of any desired sequence and length. In certain aspects, the spacer includes from 1 to 30 amino acids, such as from 3 to 20 amino acids, 3 to 15 amino acids, 3 to 10 amino acids, 3 to 5 amino acids, and may be, e.g., from 4 to 17 amino acids. For example, the spacer may contain 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more amino acids, and may in some instances contain not more than 30 or more than 25 amino acids, may be of any desired amino acid sequence with the proviso the spacer does not include a cysteine residue.

In certain aspects, the spacer includes at least one glycine (G) residue and at least one serine (S) residue. For example, the spacer may contain one or more glycine residues and one or more serine residues.

An example of a spacer of interest is a spacer having the sequence GGGS (SEQ ID NO:1). In other aspects, the spacer may include or consist of any of the following amino acid sequences: AKTTPKLEEGEFSEAR (SEQ ID NO:2); AKTTPKLEEGEFSEARV (SEQ ID NO:3); AKTTPKLGG (SEQ ID NO:4); SAKTTPKLGG (SEQ ID NO:5); AKTTPKLEEGEFSEARV (SEQ ID NO:6); SAKTTP (SEQ ID NO:7); SAKTTPKLGG (SEQ ID NO:8); RADAAP (SEQ ID NO:9); RADAAPTVS (SEQ ID NO:10); RADAAAAGGPGS (SEQ ID NO:11); RADAAAA (G$_4$S)$_4$ (SEQ ID NO:12), SAKTTP (SEQ ID NO:13); SAKTTPKLGG (SEQ ID NO:14); SAKTTPKLEEGEFSEARV (SEQ ID NO:15); ADAAP (SEQ ID NO:16); ADAAPTVSIFPP (SEQ ID NO:17); TVAAP (SEQ ID NO:18); TVAAPSVFIFPP (SEQ ID NO:19); QPKAAP (SEQ ID NO:20); QPKAAPSVTLFPP (SEQ ID NO:21); AKTTPP (SEQ ID NO:22); AKTTPPSVTPLAP (SEQ ID NO:23); AKTTAP (SEQ ID NO:24); AKTTAPSVYPLAP (SEQ ID NO:25); ASTKGP (SEQ ID NO:26); ASTKGPSVFPLAP (SEQ ID NO:27); GGGGSGGGGSGGGGS (SEQ ID NO:28); GENKVEYAPALMALS (SEQ ID NO:29); GPAKELTPLKEAKVS (SEQ ID NO:30); GHEAAAVMQVQYPAS (SEQ ID NO:31); AA; GGGGS (SEQ ID NO:128); GGGGSSGGGGSS; (SEQ ID NO:131); or variants thereof that include 1, 2, 3, 4, or 5 amino acid substitutions.

In certain aspects, the C-terminal extension of the light chain polypeptide includes an amino acid sequence having endogenous human amino acid sequences or modified human amino acid sequences. These may include human antibody hinge region sequences, T-cell receptor sequences, or any other human protein sequences of interest. Additional amino acid sequences that may be employed include, but are not limited to, extracellular protein amino acid sequences, as well as the sequences of extracellular domains of proteins present on a cell surface. In one embodiment, the extension includes an endogenous human amino acid sequence that includes one or more naturally occurring cysteine residues. When such native human sequences include one or more cysteine residues, in the absence of sequence modifications, the non-cysteine-containing amino acid sequences N-terminal and C-terminal to the cysteine residues constitute spacer sequences of the C-terminal extension. In one embodiment, the extension includes a modified human amino acid sequence in which one or more cysteines has been introduced into the endogenous human amino acid sequence by insertion or substitution. Naturally occurring cysteine residues may also be substituted or deleted in the context of such sequences.

According to certain embodiments, when the C-terminal extension includes an endogenous human amino acid sequence or modified human amino acid sequence, the immunogenicity of the antibody (or conjugate thereof) when administered to a patient is reduced as compared to a corresponding extension lacking the human amino acid sequence or modified human amino acid sequence.

Figure 2:
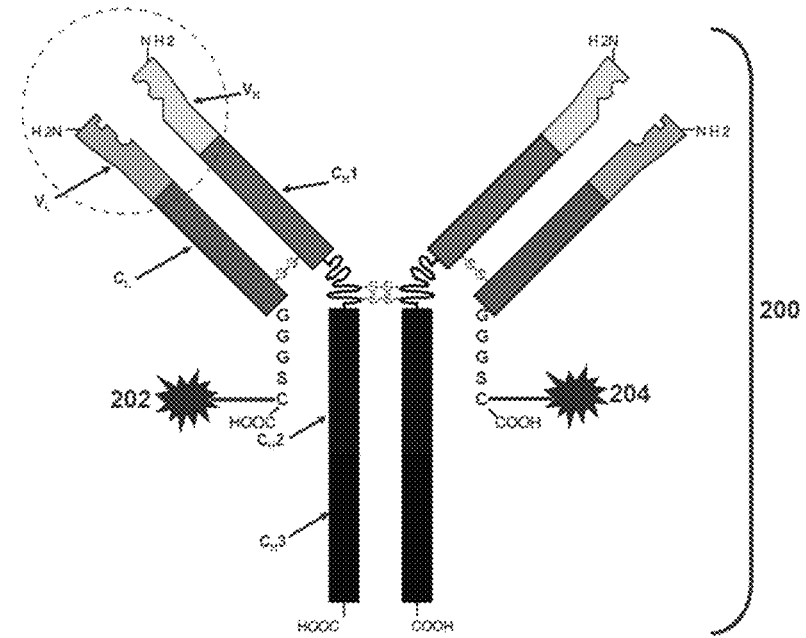
FIG. 2 is a schematic illustration of a conjugate according to one embodiment of the present disclosure.

Preferred spacers include amino acid sequences with at least 85%, 90%, 95%, 98% or 100% sequence identity to the wild-type sequence, such as a portion of a hinge region, or fragment thereof, of a wild-type IgM, IgG, IgA, IgE or IgD antibody molecule or T cell receptor. In one aspect, the "hinge" region refers to the amino acid sequence of an antibody (such as depicted in the examples of FIGS. 1 and 2) located between the C$_H$1 and C$_H$2 domains of a heavy chain polypeptide, e.g., a heavy chain polypeptide of an IgG, IgA or IgD antibody. The hinge region of the constructs of the present disclosure may vary in length and amino acid sequence. For example, the hinge regions of human IgG$_1$, IgG$_2$ and IgG$_4$ are 12-15 amino acids in length, while human IgG$_3$ has a 62 amino acid hinge region. Human IgD antibody molecules have a 64 amino acid hinge region. According to certain embodiments, when the C-terminal extension includes a hinge region sequence or sequence variant thereof, the immunogenicity of the antibody (or conjugate thereof) when administered to a patient is reduced as compared to a corresponding extension lacking the hinge region sequence, and the flexibility of the extension may be increased relative to an extension lacking the hinge region sequence.

Non-limiting examples of hinge region amino acid sequences, of which all or a portion thereof (e.g., at least 2, 3, 4, 5, 6 or more contiguous residues) may be included in the C-terminal extensions of the present disclosure, include but are not limited to, ESSCDVKLVEKSFET (SEQ ID NO: 32) (T cell receptor alpha constant); DCGFTS (SEQ ID NO: 33) (T cell receptor beta constant); DVITMDPKDNCSKDAN (SEQ ID NO: 34) (T cell receptor gamma constant); DHVKPKETENTKQPSKSCHKPK (SEQ ID NO: 35) (T cell receptor delta constant); EPKSCDKTHTCPPCP (SEQ ID NO: 36) (IgCHG1); ERKCCVECPPCP (SEQ ID NO: 37) (IgCHG2); ELKTPLGDTTHTCPRCP (SEQ ID NO: 38) (IgCH3-H1); EPKSCDTPPPCPRCP (SEQ ID NO: 39) (IgCH3-H2, IgCH3-H3, and IgCH3-H4); ESKYGPPCPSCP (SEQ ID NO: 40) (IgH4); VPPPPP (SEQ ID NO: 41) (IgA2) and ESPKAQASSVPTAQPQAEGSLAKATTAPATTRNTGRGGEEKKKEKEKEEQEERETKTP (SEQ ID NO: 42).

Non-limiting examples of non-cysteine-containing amino acid sequences derived from hinge region amino acid sequences, of which all or a portion thereof (e.g., at least 2, 3, 4, 5, 6 or more contiguous residues) may be used as spacers in the C-terminal extensions of the present disclosure, include but are not limited to, ESS (SEQ ID NO: 43); DVKLVEKSFET (SEQ ID NO: 44); GFTS (SEQ ID NO: 45); DVITMDPKDN (SEQ ID NO: 46); SKDAN (SEQ ID NO: 47); DHVKPKETENTKQPSKS (SEQ ID NO: 48); HKPK (SEQ ID NO: 49); EPKS (SEQ ID NO: 50); DKTHT (SEQ ID NO: 51); ERK (SEQ ID NO: 52); ELKTPLGDTTHT (SEQ ID NO: 53); DTPPP (SEQ ID NO: 54); VE (SEQ ID NO: 55); PR (SEQ ID NO: 56); PP (SEQ ID NO: 57); PS (SEQ ID NO: 58); ESKYGPP (SEQ ID NO: 59); and DVKLV (SEQ ID NO:91).

The C-terminal extension of a light chain polypeptide of the present disclosure may be designed to include any desired combination of one or more spacers (or no spacer) and one or more cysteine residues. As such, an aspect of the present disclosure is to provide an extension at the C-terminus of a light chain polypeptide having one or more cysteines (e.g., spaced apart from each other or not spaced apart from each other; spaced from the C-terminus of the parental light chain polypeptide or not spaced from the C-terminus of the parental light chain polypeptide; and/or spaced from the C-terminus of the light chain extension or not spaced from the C-terminus of the light chain extension), so that one may control the corresponding number and spacing of agents (e.g., cytotoxic agents, labeling agents, and/or the like) linked to such cysteine(s) in a conjugated product of such an antibody.

According to certain embodiments, the C-terminal extension comprises an amino acid sequence which may be represented, from N-terminus to C-terminus, by Formula I:

$$(X_a C_b)_c (X'_d C_e)_f \qquad (I)$$

wherein

X and X' represent a spacer of one or more amino acids, wherein the amino acid sequence of each X and X' is independently selected from any amino acid sequence of interest, including any of the examples of spacer amino acid sequences provided herein;

C represents a cysteine residue, a, b, c, d, e and f are integers independently selected from 0, 1, 2, 3, 4, 5, 6, 7, 8, 9, 10, 11, 12, 13, 14, 15, 16, 17, 18, 19 and 20, wherein the sum of b and e is at least 1, and the sum of c and f is at least 1. X and X' may be the same or different. Where c is greater than 1, then each X of $(X_a C_b)_c$ may be the same or different amino acid sequence within each repeat unit of $(X_a C_b)_c$. Where d is greater than 1, then each X' of $(X'_d C_e)_f$ may the same or different amino acid sequence within each repeat unit of $(X'_d C_e)_f$.

The present disclosure also provides nucleic acids encoding a C-terminal extension of Formula I, as well as nucleic acids encoding a light chain polypeptide comprising a C-terminal extension of Formula I.

In certain embodiments, the C-terminal extension may be represented, from N-terminus to C-terminus, by Formula I above, where b and e are integers independently selected from 0, 1, and 2, wherein the sum of b and e is at least 1, and a, c, d, and f are integers independently selected from 0, 1, 2, 3, 4, 5, 6, 7, 8, 9, 10, 11, 12, 13, 14, 15, 16, 17, 18, 19 and 20, where the sum of c and f is at least 1.

In certain embodiments, the C-terminal extension may be represented, from N-terminus to C-terminus, by Formula I above, where b and e are integers independently selected from 0, 1, and 2, wherein the sum of b and e is at least 2, and a, c, d, and f are integers independently selected from 0, 1, 2, 3, 4, 5, 6, 7, 8, 9, 10, 11, 12, 13, 14, 15, 16, 17, 18, 19 and 20, where the sum of c and f is at least 1.

In certain embodiments, the C-terminal extension may be represented, from N-terminus to C-terminus, by Formula I above, where b and e are integers independently selected from 0, 1, and 2, where the sum of b and e is at least 1, a and d are integers independently selected from 0, 1, 2, 3, 4, 5, 6, 7, 8, 9, and 10, and c and f are integers independently selected from 0, 1, 2, 3, 4, 5, 6, 7, 8, 9, and 10, where the sum of c and f is at least 1.

In certain embodiments, the C-terminal extension may be represented, from N-terminus to C-terminus, by the formula I above, wherein b and e are integers independently selected from 0, 1, and 2, wherein the sum of b and e is at least 2, a and d are integers independently selected from 0, 1, 2, 3, 4, 5, 6, 7, 8, 9, and 10, and c and f are integers independently selected from 0, 1, 2, 3, 4, 5, 6, 7, 8, 9, and 10, where the sum of c and f is at least 1.

As an example, with reference to Formula I, where X is a spacer having the sequence GGGS (SEQ ID NO:1) for purposes of illustration; a, b and c each=1; and f=0, then the C-terminal extension has the sequence GGGSC (SEQ ID NO:60) (also referred to herein as "Cys1"). An example of an antibody having a light chain polypeptide with a C-terminal extension according to this embodiment is schematically illustrated in FIG. 1. As shown, antibody 100 includes two light chain polypeptides that include light chain variable ($V_L$) and constant ($C_L$) domains, and C-terminal extensions 102 and 104 having the sequence GGGSC extending from the C-terminal residue of each of the ($C_L$) domains.

In one embodiment, when X is GGGS (SEQ ID NO:1), a is 1, c is 1, and f is 0.

In one example, with reference to Formula I above, where X is a spacer having the sequence GGGS (SEQ ID NO:1) for purposes of illustration; a and c each=1, b=2, and f=0, then the C-terminal extension has the sequence GGGSCC (SEQ ID NO:61).

In one example, with reference to Formula I above, where X is GGGS (SEQ ID NO:1) for purposes of illustration, where a=2, b=1, c=1, and f=0, the C-terminal extension has the sequence GGGSGGGSC (SEQ ID NO:62) when each spacer sequence is the same.

In one example, with reference to Formula I above, where X is GGGS (SEQ ID NO:1) for purposes of illustration, and where a=1, b=1, c=2, and f=0, the C-terminal extension has the sequence GGGSCGGGSC (SEQ ID NO:63) (also referred to herein as "Cys2") when each spacer sequence is the same.

In one example, with reference to Formula I above, where X is GGGS (SEQ ID NO:1) for purposes of illustration, and where a=1, b=1, c=4, and f=0, the extension would have the sequence GGGSCGGGSCGGGSCGGGSC (SEQ ID NO:64) (also referred to herein as "Cys4") when each spacer sequence is the same.

In one example, with reference to Formula I above, where X is GGGS (SEQ ID NO:1) for purposes of illustration, and where a=1, b=1, c=1, d=3, e=1, and f=1, the extension would have the sequence GGGSCGGGSGGGSGGGSC (SEQ ID NO:65) when each spacer sequence is the same.

In one example, with reference to Formula I above, where X is GGGS (SEQ ID NO:1) for purposes of illustration, and where a=2, b=1, c=1, d=1, e=1, and f=1, the extension would have the sequence GGGSGGGSCGGGSC (SEQ ID NO:66) when each spacer sequence is the same.

In one example, with reference to Formula I above, where X is GGGS (SEQ ID NO:1) for purposes of illustration, and where a=1, b=1, c=1, d=2, e=1, and f=1, the extension would have the sequence GGGSCGGGSGGGSC (SEQ ID NO:67) when each spacer sequence is the same.

In one example, with reference to Formula I above, where X is GGGS (SEQ ID NO:1) and X' is AKTTPKLEEGEFSEAR (SEQ ID NO:2) for purposes of illustration, and where a=1, b=1, c=1, d=2, e=1, and f=1, the extension would have the sequence GGGSCAKTTPKLEEGEFSEARC (SEQ ID NO:89).

In one example, with reference to Formula I above, where c=2 and X is GGGS (SEQ ID NO:1) in the context of the first occurrence of $(X_aC_b)_c$ and X is AKTTPKLEEGEFSEAR (SEQ ID NO:2) in the context of the second occurrence of $(X_aC_b)_c$, and X' is AKTTPKLEEGEFSEAR (SEQ ID NO:2) for purposes of illustration, and where a=1, b=1, c=2, d=2, e=1, and f=1, the extension would have the sequence GGGSCAKTTPKLEEGEFSEARCAKTTPKLEEGEFSEARC (SEQ ID NO:90).

As an example, with reference to Formula I, where X is a spacer having the sequence AKTTPKLEEGEFSEAR (SEQ ID NO:2) for purposes of illustration, where a, b and c are each=1; and f=0, then the C-terminal extension has the sequence AKTTPKLEEGEFSEARC (SEQ ID NO:68).

In one example, with reference to Formula I above, where X is AKTTPKLEEGEFSEAR (SEQ ID NO:2) for purposes of illustration, where a=2, b=1, c=1, and f=0, the C-terminal extension has the sequence AKTTPKLEEGEFSEAR-AKTTPKLEEGEFSEARC (SEQ ID NO:69) when each spacer sequence is the same.

In one example, with reference to Formula I above, where X is AKTTPKLEEGEFSEAR (SEQ ID NO:2) for purposes of illustration, and where a=1, b=1, c=2, and f=0, the C-terminal extension has the sequence AKTTPKLEEGEFSEARCAKTTPKLEEGEFSEARC (SEQ ID NO:70) when each spacer sequence is the same.

In one example, with reference to Formula I above, where X is AKTTPKLEEGEFSEAR (SEQ ID NO:2) for purposes of illustration, and where a=1, b=1, c=4, and f=0, the extension would have the sequence AKTTPKLEEGEFSEARCAKTTPKLEEGEFSEARCAKTTPKLEEGEFSEARCAKTTPKLEE GEFSEARC (SEQ ID NO:71) when each spacer sequence is the same.

In one example, with reference to formula I above, where X is AKTTPKLEEGEFSEAR (SEQ ID NO:2) for purposes of illustration, and where a=1, b=1, c=1, d=3, e=1, and f=1, the extension would have the sequence AKTTPKLEEGEFSEARCAKTTPKLEEGEFSEAR-AKTTPKLEEGEFSEARAKTTPKLEEGEF SEARC (SEQ ID NO:72) when each spacer sequence is the same.

In one example, with reference to Formula I above, where X is AKTTPKLEEGEFSEAR (SEQ ID NO:2) for purposes of illustration, and where a=2, b=1, c=1, d=1, e=1, and f=1, the extension would have the sequence AKTTPKLEEGEFSEAR-AKTTPKLEEGEFSEARCAKTTPKLEEGEFSEARC (SEQ ID NO:73) when each spacer sequence is the same.

In one example, with reference to Formula I above, where X is AKTTPKLEEGEFSEAR (SEQ ID NO:2) for purposes of illustration, and where a=1, b=1, c=1, d=2, e=1, and f=1, the extension would have the sequence AKTTPKLEEGEFSEARCAKTTPKLEEGEFSEAR-AKTTPKLEEGEFSEARC (SEQ ID NO:74) when each spacer sequence is the same.

In another example, a C-terminal extension of the present disclosure may be represented by Formula II:

$$(X_aC_b)_c(X'_dC_e)_f(X''_gC_h)_i \quad (II)$$

where

X, X', and X" represent a spacer of one or more amino acids, wherein the amino acid sequence of each X, X' and X" is independently selected from any amino acid sequence of interest, including any of the examples of spacer amino acid sequences provided herein;

C is a cysteine residue: and a, b, c, d, e, f, g, h and i are integers independently selected from 0, 1, 2, 3, 4, 5, 6, 7, 8, 9, 10, 11, 12, 13, 14, 15, 16, 17, 18, 19 and 20, where the sum of b, e and h is at least 1, and the sum of c, f and i is at least 1. X, X', and X" may be the same or different. Where c is greater than 1, then each X of $(X_aC_b)_c$ may be the same or different amino acid sequence within each repeat unit of $(X_aC_b)_c$. Where d or f is greater than 1, then each X' of $(X'_dC_e)_f$ may the same or different amino acid sequence within each repeat unit of $(X'_dC_e)_f$. Where g or i is greater than 1, then each X" of $(X''_gC_h)_i$ may the same or different amino acid sequence within each repeat unit of $(X''_gC_h)_i$.

A C-terminal extension of the present disclosure may include (e.g., consist of) an amino acid sequence selected from: EPKSCDKTHTC (SEQ ID NO:92) (also referred to herein as extension 1); EPKSCDKTHTCPPC (SEQ ID NO:93) (also referred to herein as extension 2); EPKSC (SEQ ID NO:94) (also referred to herein as extension 3); ESKYGPPC (SEQ ID NO:95) (also referred to herein as extension 4); ERKCCVECPPC (SEQ ID NO:96) (also referred to herein as extension 5); ERKC (SEQ ID NO:97) (also referred to herein as extension 6); DVITMDPKDNC (SEQ ID NO:98) (also referred to herein as extension 7); DHVKPKETENTKQPSKSCHKPK (SEQ ID NO:99) (also referred to herein as extension 8); ESSC (SEQ ID NO:100) (also referred to herein as extension 9); ESSCDVKLV (SEQ ID NO:101) (also referred to herein as extension 10); DHVKPKETENTKQPSKSC (SEQ ID NO:102) (also referred to herein as extension 11); DVITMDPKDNCSK-DAN (SEQ ID NO:103) (also referred to herein as extension 12); CAA, CCAA (SEQ ID NO:132), AACAA (SEQ ID NO:129), and GGGGSCAA (SEQ ID NO:130).

The present disclosure also provides nucleic acids encoding any of the C-terminal extensions described herein (e.g., C-terminal extension of Formula II, etc.), as well as nucleic acids encoding any of the light chain polypeptides described herein (e.g., light chain polypeptides comprising a C-terminal extension of Formula II, etc.).

The present disclosure provides antibodies having at least one light chain polypeptide having a C-terminal extension of the present disclosure. In some embodiments, the antibody has two light chain polypeptides having a C-terminal extension of the present disclosure. In some embodiments, such antibodies can be conjugated to an agent/payload (e.g., a drug) through covalent attachment to at least one cysteine in the C-terminal extension present in at least one of the light chain polypeptides of the antibody. In one embodiment, the payload is directly attached to the cysteine of the C-terminal extension. In another embodiment, the payload is attached via a linker to the cysteine of the C-terminal extension. In one embodiment, the payload is preferentially attached to the cysteine of the C-terminal extension over a cysteine outside the C-terminal amino acid extension. In one embodiment, the payload is exclusively attached to the cysteine of the C-terminal extension.

Nucleic Acids, Vectors and Host Cells

The present disclosure provides nucleic acids encoding a light chain polypeptide having a C-terminal amino acid extension (referred to herein for convenience as a "modified light chain polypeptide"), as well as vectors and host cells containing such nucleic acids. The modified light chain polypeptide encoded by the nucleic acid may include any of the features described above, in any combination. For example, the C-terminal extension portion of the light chain polypeptide may include any of the C-terminal extension features described above with respect to the length of the extension, the amino acid sequence of the extension, the number of spacers in the extension and amino acid sequences thereof, extension configurations based on combinations of one or more spacers and one or more cysteine residues, and any other aspects of the C-terminal extensions described above and elsewhere herein.

A nucleic acid (e.g., DNA or RNA) encoding a C-terminal extension-containing light chain polypeptide can be operably linked to one or more regulatory elements, such as a promoter and enhancer, that allow expression of the nucleic acid in a host cell (e.g., a cell that is genetically modified to synthesize the encoded modified light chain polypeptide).

For example, where the host cell is a prokaryotic hose cell, example of promoters include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter, a pagC promoter; a nirB promoter; a sigma70 promoter, e.g., a consensus sigma70 promoter; a stationary phase promoter, e.g., a dps promoter, an spy promoter, and the like; a promoter derived from the pathogenicity island SPI-2; an actA promoter; an rpsM promoter; a tet promoter; an SP6 promoter; and the like. Examples of strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator.

In some embodiments, e.g., for expression in a yeast cell, the promoter can be a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC 1 promoter, a TRP 1 promoter, a URA3 promoter, a LEU2 promoter, an ENO promoter, a TP1 promoter, and AOX1 (e.g., for use in *Pichia*).

A nucleotide sequence encoding the modified light chain polypeptide can be present in an expression vector and/or a cloning vector. When it is desirable to express the modified light chain polypeptide and one or more other polypeptide components of an antibody, e.g., to provide for an antibody having a modified light chain polypeptide of the present disclosure, the corresponding nucleotide sequences encoding the two or more polypeptides may be cloned in the same or separate vectors. An expression vector can include a selectable marker, an origin of replication, and other features that provide for replication and/or maintenance of the vector.

Expression vectors generally have convenient restriction sites located near the promoter sequence to provide for the insertion of nucleic acid sequences encoding heterologous proteins. Examples of expression vectors include, but are not limited to, viral vectors (e.g. viral vectors based on vaccinia virus; poliovirus; adenovirus; adeno-associated virus; SV40; herpes simplex virus; human immunodeficiency virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Also provided is a host cell that includes any of the nucleic acids encoding the modified light chain polypeptide, or vectors including the same. In certain aspects, the host cell is a prokaryotic host cell or a eukaryotic host cell. The host cell may be an isolated genetically modified host cell (e.g., an in vitro cell) that is genetically modified (e.g., transformed or transfected) with a nucleic acid of the present disclosure. In some embodiments, a genetically modified host cell of the present disclosure can produce a modified light chain polypeptide of the present disclosure, which antibody light chain polypeptide can have any of the features described elsewhere herein.

Examples of host cells include eukaryotic host cells, such as a mammalian cell, an insect host cell, a yeast cell; and prokaryotic cells, such as a bacterial cell. Introduction of a the nucleic acid into the host cell can be effected, for example by calcium phosphate precipitation, DEAE dextran mediated transfection, liposome-mediated transfection, electroporation, or other known methods.

Examples of mammalian host cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Examples of yeast host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Examples of prokaryotic cells include, but are not limited to, any of a variety of laboratory strains of *Escherichia coli, Lactobacillus* sp., *Salmonella* sp., *Shigella* sp., and the like. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella disenteriae*. Typically, the laboratory strain is one that is non-pathogenic. Non-limiting examples of other suitable bacteria include, but are not limited to, *Bacillus subtilis*, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, *Rhodococcus* sp., and the like.

Methods of Producing Antibody Light Chain Polypeptides and Antibodies

As discussed above, the present disclosure provides methods of making modified light chain polypeptides (i.e., a light chain polypeptide having a C-terminal extension of the present disclosure), as well as antibodies containing one or more of such modified light chain polypeptides.

According to one embodiment, provided is a method of making a light chain polypeptide of an antibody, the method including expressing in a host cell a nucleic acid encoding a light chain polypeptide that includes a C-terminal amino acid extension as described herein. The light chain polypeptide may be produced by any convenient method, e.g., conventional synthetic methods for protein synthesis, recombinant DNA methods, etc. The light chain polypeptide having a C-terminal amino acid extension may be produced in combination with the production of a heavy chain polypeptide of interest, or may be combined with a heavy chain polypeptide following production (e.g., by fusion of recombinant cells which separately express a light chain polypeptide of the present disclosure and a heavy chain polypeptide).

Recombinant methods can be used for production of the light chain polypeptide. For example, nucleic acids encoding a light chain polypeptide of interest may be inserted into an expression vector. The nucleic acid segment encoding the light chain polypeptide may be operably linked to one or more control sequences in the expression vector that ensure the expression of the light chain polypeptide. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for a desired level of expression of the nucleotide sequences, and the collection and purification of the light chain polypeptide.

Because of the degeneracy of the genetic code, a variety of nucleic acid sequences can encode the desired light chain polypeptide. The nucleic acid sequence encoding the light chain polypeptide can be produced by de novo solid-phase DNA synthesis, by polymerase chain reaction (PCR) mutagenesis (e.g., overlapping PCR) of a nucleic acid that encodes a light chain polypeptide of a parental antibody that lacks a C-terminal amino acid extension. An example approach which utilizes overlapping PCR for generating nucleic acids that encode light chain polypeptides having C-terminal amino acid extensions is described in detail in the Examples section herein.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences. Examples of expression vectors and host cells are discussed above. For example, the host cells can be prokaryotic cells, (e.g., *Escherichia coli*, bacilli (such as *Bacillus subtilis*) *Salmonella*, *Serratia*, *Pseudomonas* species, and the like), yeast cells (e.g., *Saccharomyces* (e.g., *S. cerevisiae*), *Pichia* and the like), and mammalian cells (e.g., CHO cell lines, Cos cell lines, HeLa cells, myeloma cell lines, transformed B-cells, hybridomas and the like).

Where the light chain polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of the light chain polypeptide. Various forms of SPPS, such as Fmoc and Boc, are available for synthesizing the light chain polypeptide. Techniques for solid phase synthesis are available in the art. For example, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Once synthesized (either recombinantly or chemically), the modified light chain polypeptides, either alone or as part of an antibody, can be purified according to standard procedures. The modified light chain polypeptide, either alone or as part of an antibody, can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than the light chain polypeptide, and the like.

According to certain embodiments the light chain polypeptide is produced by in vitro translation. See, e.g., Yin et al. (2012) Aglycosylated antibodies and antibody fragments produced in a scalable in vitro transcription-translation system, *Landes Bioscience*, Volume 4, Issue 2.

The antibody may be a recombinant antibody, e.g., a chimeric, humanized, fully human, bispecific, deimmunized, and/or an in vitro generated antibody.

Conjugates

The present disclosure provides antibodies having at least one light chain polypeptide having a C-terminal extension, where at least one cysteine of the C-terminal extension is conjugated to an agent (e.g., drug).

The light chain polypeptide having a C-terminal extension of the antibody portion of the conjugates of the present disclosure may include any of the features described above, and in any combination. For example, the C-terminal extension of the antibody portion of the conjugate may include any of the C-terminal extension features described above with respect to the length of the extension, the amino acid composition of the extension, the number of spacers in the extension and amino acid sequences thereof, extension configurations based on combinations of one or more spacers and one or more cysteine residues, and any other aspects of the C-terminal extensions described above and elsewhere herein.

Accordingly, the antibody conjugates of the present disclosure have at least one light chain polypeptide having a C-terminal extension, where at least one cysteine residue of the C-terminal extension is conjugated to an agent. In some embodiments, each of the light chain polypeptides of the antibody conjugates of the present disclosure have a C-terminal extension, where at least one cysteine residue of the C-terminal extensions of each of the modified light chain polypeptides is conjugated to an agent. For example, a first agent may be conjugated to a cysteine residue of the C-terminal extension of a first modified light chain polypeptide, and a second agent may be conjugated to a cysteine residue of the C-terminal extension of a second light chain polypeptide. In one embodiment, the agent is preferentially attached to the cysteine residue of the C-terminal extension rather than a cysteine residue outside the C-terminal amino acid extension. In certain aspects, the agent is exclusively attached to the cysteine residue of the C-terminal extension. Antibody conjugates of the present disclosure can include any number of agents conjugated to the C-terminal extension of the modified light chain polypeptide(s), according to the number of cysteines in the C-terminal extension available for conjugation, e.g., 1, 2, 3, 4, 5, 6, 7, 8, 9, 10, 11, 12, 13, 14, 15, 16, 17, 18, 19, or more cysteines. In some embodiments, the C-terminal extension of a modified light chain polypeptide(s) of the antibody is conjugated to an agent or agents via covalent binding to at least 1, 2, 3, 4, 5, or more cysteines of the C-terminal extension. In some embodiments the C-terminal extension of a modified light chain polypeptide(s) of the antibody is conjugated to an agent or agents via covalent binding to no more than 2, 3, 4, 5, 6, 7, 8, 9 or 10 cysteines of the C-terminal extension. In certain aspects, the extension includes an agent that is conjugated to two or more adjacent cysteine residues in the extension, either directly or via one or more linkers. For example, the extension may include an agent that is conjugated to two adjacent cysteine residues in the extension.

In certain embodiments, the number of agents conjugated to the C-terminal extensions of modified light chain polypeptide(s) of the antibody can be characterized by the drug-to-antibody ratio (DAR). In some instances, a distribution of a plurality of antibody conjugates may be characterized by measuring the average DAR of the antibody conjugates in the distribution, where the average DAR indicates the average number of agents conjugated to the C-terminal extensions of modified light chain polypeptide(s) of the antibodies in the distribution. By "average" is meant the arithmetic mean. In certain cases, average DAR is assayed by Hydrophobic Interaction Chromatography (HIC). Thus, an average DAR provides an indication of the average drug-to-antibody ratio of the antibody conjugates in a distribution provided by the DAR assay.

In some instances, the DAR of an antibody conjugate according to the present disclosure ranges from 0 to 20, such as from 1 to 17, or 1 to 15, or 1 to 12, or 1 to 10, or 1 to 9, or 1 to 8, or 1 to 7, or 1 to 6, or 1 to 5, or 1 to 4, or 1 to 3. For instance, a DAR of 0 indicates that the antibody is unconjugated; a DAR of 1 indicates that one agent (e.g., drug) is conjugated to a C-terminal extension of a modified light chain polypeptide of the antibody; a DAR of 2 indicates that two agents are conjugated to one or more C-terminal extensions of modified light chain polypeptide(s) of the antibody; a DAR of 3 indicates that three agents are conjugated to one or more C-terminal extensions of modified light chain polypeptide(s) of the antibody; a DAR of 4 indicates that four agents are conjugated to one or more C-terminal extensions of modified light chain polypeptide(s) of the antibody; etc. In some instances, the DAR of an antibody conjugate according to the present disclosure is 1, 2, 3, 4, 5, 6, 7, 8, 9, 10, 11, 12, 13, 14, 15, 16, 17, 18, 19 or 20.

In some instances, the average DAR of a distribution of antibody conjugates according to the present disclosure ranges from 0 to 20, such as from 1 to 17, or 1 to 15, or 1 to 12, or 1 to 10, or 1 to 9, or 1 to 8, or 1 to 7, or 1 to 6, or 1 to 5, or 1 to 4, or 1 to 3. For instance, an average DAR of 0 indicates that, on average, the antibodies in the distribution are unconjugated; an average DAR of 1 indicates that, on average, one agent (e.g., drug) is conjugated to each antibody in the distribution; an average DAR of 2 indicates that, on average, two agents are conjugated each antibody in the distribution; an average DAR of 3 indicates that, on average, three agents are conjugated to each antibody in the distribution; an average DAR of 4 indicates that, on average, four agents are conjugated to each antibody in the distribution; etc. In some instances, an average DAR of a distribution of antibody conjugates according to the present disclosure is 1, 2, 3, 4, 5, 6, 7, 8, 9, 10, 11, 12, 13, 14, 15, 16, 17, 18, 19 or 20.

In certain embodiments, a sample containing antibody conjugates according to the present disclosure includes a mixture of distributions of unconjugated and conjugated (e.g., mono-conjugated, di-conjugated, tri-conjugated, etc.) antibodies. The average DAR of each distribution of antibody conjugates may be assayed (e.g., by HIC). For example, a sample containing antibody conjugates may include a distribution of unconjugated antibodies (i.e., antibody conjugates having an average DAR=0), a distribution of mono-conjugated antibodies (i.e., antibody conjugates having an average DAR=1), a distribution of di-conjugated antibodies (i.e., antibody conjugates having an average DAR=2), a distribution of tri-conjugated antibodies (i.e., antibody conjugates having an average DAR=3), etc.

An example antibody conjugate according to an embodiment of the present disclosure is schematically illustrated in FIG. 2. As shown, conjugate 200 includes an antibody having two light chain polypeptides that include light chain variable ($V_L$) and constant ($C_L$) domains, and C-terminal extensions having the sequence GGGSC extending from the C-terminal residue of each of the ($C_L$) domains. Conjugate 200 further includes agents 202 and 204 linked to the cysteine residue of the extension via a linker.

Linkers

In certain aspects, the agent is conjugated to the cysteine residue via a linker. Linkers that find use in the conjugates of the present disclosure include maleimide or maleimide-based linkers; valine-citrulline linkers; hydrazone linkers; N-succinimidyl-4-(2-pyridyldithio)butyrate (SPDB) linkers; Succinimidyl-4-(N-maleimidomethyl)cyclohexane-1-carboxylate (SMCC) linkers; vinylsulfone-based linkers; linkers involving metal atom(s) coordinated to cysteine; linkers that include polyethylene glycol (PEG), such as, but not limited to tetraethylene glycol; linkers that include propanoic acid; linker that include caproleic acid; linkers that include Fleximer® polymers (Mersana Therapeutics, Cambridge, Mass.) or the linkers used to attach drugs to Fleximer polymers (see, e.g., U.S. Pat. No. 8,524,214, incorporated herein by reference in its entirety); and linkers including any combination thereof.

In certain aspects, the linker is a chemically-labile linker, such as an acid-cleavable linker that is stable at neutral pH (bloodstream pH 7.3-7.5) but undergoes hydrolysis upon internalization into the mildly acidic endosomes (pH 5.0-6.5) and lysosomes (pH 4.5-5.0) of a target cell (e.g., a cancer cell). Chemically-labile linkers include, but are not limited to, hydrazone-based linkers. According to certain embodiments, the linker is an enzyme-labile linker, such as an enzyme-labile linker that is stable in the bloodstream but undergoes enzymatic cleavage upon internalization into a target cell, e.g., by a lysosomal protease (such as cathepsin or plasmin) in a lysosome of the target cell (e.g., a cancer cell). Enzyme-labile linkers include, but are not limited to, linkers that include peptidic bonds, e.g., valine-citrulline linkers, such as a maleimidocaproyl-valine-citruline-p-aminobenzyl (MC-vc-PAB) linker, and the like. In certain aspects, the linker is a non-cleavable linker, such as a linker that includes a non-cleavable thioether bond. Chemically-labile linkers, enzyme-labile, and non-cleavable linkers are known and described in detail, e.g., in Ducry & Stump (2010) *Bioconjugate Chem.* 21:5-13.

According to certain embodiments, the linker is (or includes) a sulfhydryl-reactive chemical group capable of reacting with one or more reduced sulfhydryl group (or thiol, -SH) of the cysteine residue(s) of the C-terminal amino acid extension. Sulfhydryl-reactive chemical groups that find use in linking the agent to the cysteine of the C-terminal extension include, but are not limited to, maleimides, haloacetyls, pyridyl disulfides, aziridines, acryloyls, arylating agents, vinylsulfones, TNB-thiols, metals, and disulfide reducing agents. Such groups may conjugate to sulfhydryls by alkylation (e.g., by the formation of a thioether bond), disulfide exchange (formation of a disulfide bond), or the like.

Agents

The agents which are the payload of the antibody conjugates of the present disclosure can be any suitable agent. The agent selected for use in the antibody conjugates of the present disclosure will vary depending on the application for which the conjugate is employed (e.g., killing, prevention of cell proliferation, hormone therapy, target imaging, and/or gene therapy, etc.). Agents of interest include, but are not limited to, therapeutic agents (e.g., drugs (e.g., cytotoxic agents)), detectable agents (e.g., in vivo imaging agents), and/or any other agent useful for a particular antibody-based application of interest.

Non-limiting examples of such agents include toxins, fragments of toxins, lectins, alkylating agents, enzymes, antibiotics such as antibacterials, antifungals, antimycoplasmals, etc., antiviral agents, antimetabolites, antiproliferative or antineoplastic agents, DNA, radioopaque dyes, radioactive isotopes (e.g., $I^{123}$, $I^{131}$ as well as radioactive metal ions), metal ions, fluorogenic compounds, marker compounds, and compounds which alter cell membrane permeability. In certain aspects, the agent is (or includes) a member of a specific binding pair, e.g., biotin (which forms a specific binding pair with avidin/streptavidin).

According to certain embodiments, the agent is a therapeutic agent. Therapeutic agents of interest include agents capable of affecting the function of a cell/tissue to which the conjugate binds via specific binding of the antibody portion of the conjugate to an antigen on the surface of the cell/tissue. For example, the agent may boost the function of the cell/tissue to which the conjugate specifically binds. Alternatively, when the function of the cell/tissue is pathological, an agent that reduces the function of the cell/tissue may be employed. In certain aspects, a conjugate of the present disclosure includes an agent that reduces the function of a target cell/tissue by inhibiting cell proliferation and/or killing the cell/tissue. Such agents may vary and include cytostatic agents and cytotoxic agents (e.g., an agent capable of killing a target cell tissue with or without being internalized into a target cell).

In certain aspects, the therapeutic agent is a cytotoxic agent selected from an enediyne, a lexitropsin, a duocarmycin, a taxane, a puromycin, a dolastatin, a maytansinoid, and a *vinca* alkaloid. In some embodiments, the cytotoxic agent is paclitaxel, docetaxel, CC-1065, CPT-11 (SN-38), topotecan, doxorubicin, morpholino-doxorubicin, rhizoxin, cyanomorpholino-doxorubicin, dolastatin-10, echinomycin, combretastatin, calicheamicin, maytansine, maytansine DM1, maytansine DM4, DM-1, an auristatin or other dolastatin derivatives, such as auristatin E or auristatin F, AEB (AEB-071), AEVB (5-benzoylvaleric acid-AE ester), AEFP (antibody-endostatin fusion protein), MMAE (monomethylauristatin E), MMAF (monomethylauristatin F), pyrrolobenzodiazepines (PBDs), eleutherobin, netropsin, or any combination thereof.

According to certain embodiments, the agent is a protein toxin selected from hemiasterlin and hemiasterlin analogs such as HTI-286 (e.g., see U.S. Pat. No. 7,579,323; WO 2004/026293; and U.S. Pat. No. 8,129,407, the full disclosures of which are incorporated herein by reference), abrin, brucine, cicutoxin, diphtheria toxin, batrachotoxin, botulism toxin, shiga toxin, endotoxin, *Pseudomonas* exotoxin, *Pseudomonas* endotoxin, tetanus toxin, pertussis toxin, anthrax toxin, cholera toxin, falcarinol, fumonisin B1, fumonisin B2, afla toxin, maurotoxin, agitoxin, charybdotoxin, margatoxin, slotoxin, scyllatoxin, hefutoxin, calciseptine, taicatoxin, calcicludine, geldanamycin, gelonin, lotaustralin, ocratoxin A, patulin, ricin, strychnine, trichothecene, zearlenone, and tetradotoxin. Enzymatically active toxins and fragments thereof which may be employed include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes.

In certain aspects, the agent is a labeling agent. By "labeling agent" (or "detectable label") is meant the agent detectably labels the antibody, such that the antibody may be detected in an application of interest (e.g., in vitro and/or in vivo research and/or clinical applications). Detectable labels of interest include radioisotopes, enzymes that generate a detectable product (e.g., horseradish peroxidase, alkaline phosphatase, etc.), fluorescent proteins, paramagnetic atoms, and the like. In certain aspects, the antibody is conjugated to a specific binding partner of detectable label (e.g., conjugated to biotin such that detection may occur via a detectable label that includes avidin/streptavidin).

According to certain embodiments, the agent is a labeling agent that finds use in in vivo imaging, such as near-infrared (NIR) optical imaging, single-photon emission computed tomography (SPECT)/CT imaging, positron emission tomography (PET), nuclear magnetic resonance (NMR) spectroscopy, or the like. Labeling agents that find use in such applications include, but are not limited to, fluorescent labels, radioisotopes, and the like. In certain aspects, the labeling agent is a multi-modal in vivo imaging agent that permits in vivo imaging using two or more imaging approaches (e.g., see Thorp-Greenwood and Coogan (2011) *Dalton Trans.* 40:6129-6143).

In certain aspects, the labeling agent is an in vivo imaging agent that finds use in near-infrared (NIR) imaging applications, which agent is selected from a Kodak X-SIGHT dye, Pz 247, DyLight 750 and 800 Fluors, Cy 5.5 and 7 Fluors, Alexa Fluor 680 and 750 Dyes, IRDye 680 and 800 CW Fluors. According to certain embodiments, the labeling agent is an in vivo imaging agent that finds use in SPECT imaging applications, which agent is selected from $^{99m}Tc$, $^{111}$In, $^{123}$In, $^{201}$Tl, and $^{133}$Xe. In certain aspects, the labeling agent is an in vivo imaging agent that finds use in positron emission tomography (PET) imaging applications, which agent is selected from $^{11}$C, $^{13}$N, $^{15}$O, $^{18}$F, $^{64}$Cu, $^{62}$Cu, $^{124}$I, $^{76}$Br, $^{82}$Rb and $^{68}$Ga.

Conjugation Methods

The present disclosure also provides methods of making antibody conjugates. The methods include conjugating an agent to an antibody that includes a light chain polypeptide including a C-terminal amino acid extension, which extension includes a cysteine residue, where the agent is conjugated to the cysteine residue (directly or indirectly (e.g., via a linker)) of the C-terminal amino acid extension. In one embodiment, the method involves the preferential (or "biased") conjugation of agent to the cysteine residue of the C-terminal amino acid extension rather than a cysteine residue outside the C-terminal extension. In certain aspects, the conjugation includes conjugating a linker to a sulfhydryl group of the cysteine residue, e.g., using maleimide reaction chemistry, haloacetyl reaction chemistry, pyridyl disulfide reaction chemistry, or any other suitable reaction chemistry as described herein. The methods of making the conjugate may further include reducing the cysteine residue to a sulfhydryl group (i.e., thiol) prior to the conjugating step, e.g., using a suitable reducing agent and reaction conditions as described above. Suitable reducing agents include, but are not limited to, DTPA, cysteamine, TCEP (tris(2-carboxyethyl)phosphine hydrochloride), combinations thereof, and the like. In certain embodiments, methods of making the conjugate include contacting the antibody that includes a light chain polypeptide including a C-terminal amino acid extension with a reducing agent. In certain embodiments, methods of making the conjugate include contacting the antibody that includes a light chain polypeptide including a C-terminal amino acid extension with a first reducing agent, followed by contacting the antibody that includes a light chain polypeptide including a C-terminal amino acid extension with a second reducing agent. An alternative embodiment of the present disclosure does not require a reduction step as the cysteine within the light chain extension is already in a reduced state as a synthesis product. In certain embodiments, the reduced antibody may be contacted with a suitable oxidizing agent. Suitable oxidizing agents include, but are not limited to, dehydroascorbic acid (DHAA), and the like. The agent conjugated to the antibody may be any useful agent. In certain aspects, the agent is a therapeutic agent or a labeling agent, which agents are described elsewhere herein.

In certain aspects, the agent is linked to the cysteine of the C-terminal extension using maleimide reaction chemistry. The maleimide group may react specifically with sulfhydryl groups when the pH of the reaction mixture is between pH 6.5 and 7.5, resulting in the formation of a stable thioether linkage. For example, a maleimidyl-modified agent (e.g., drug) may be reacted with a reduced cysteine (e.g., sulfhydryl or thiol group) of a C-terminal amino acid extension to form a thioether linkage between the agent and the antibody. In more alkaline conditions (pH>8.5), primary amines may compete with thiols for reaction with maleimides, and also increase the rate of hydrolysis of the maleimide group to a non-reactive maleamic acid. Maleimides do not react with tyrosines, histidines or methionines. Bioconjugation approaches that employ maleimide-based linkers are described in, e.g., in Hermanson, G. T., Bioconjugate Techniques, 2nd ed. San Diego, Calif. Academic Press 2008; Aslam & Dent, Bioconjugation: Protein Coupling Techniques for the Biomedical Sciences, London Macmillan Reference Ltd 1998; Kalia & Raines, Advances in Bioconjugation, Curr. Org. Chem. 14(2):138-147. Examples of suitable conjugation approaches using a maleimide-based linker according to embodiments of the present disclosure are described in detail in the Examples section herein.

According to certain embodiments, the agent is linked to the cysteine of the C-terminal extension using haloacetyl reaction chemistry. In certain aspects, a haloacetyl linker that includes an iodoacetyl or a bromoacetyl group is employed. In certain embodiments, haloacetyls react with sulfhydryl groups at physiologic pH. The reaction of the iodoacetyl group proceeds by nucleophilic substitution of iodine with a sulfur atom from a sulfhydryl group, resulting in a stable thioether linkage.

In certain aspects, the agent is linked to the cysteine of the C-terminal extension using pyridyl disulfide reaction chemistry. In certain embodiments, pyridyl disulfides react with sulfhydryl groups over a broad pH range (with pH 4 to 5 being optimal) to form disulfide bonds. During the reaction, a disulfide exchange occurs between the sulfhydryl group of the antibody and a 2-pyridyldithiol group of a 2-pyridyldithiol-modified agent. As a result, pyridine-2-thione is released and can be measured spectrophotometrically (Amax=343 nm) to monitor the progress of the reaction.

To generate a reduced sulfhydryl in the cysteine of the C-terminal amino acid extension to which the agent may be attached (e.g., via a linker), the cysteine may be contacted with a suitable reducing agent under conditions sufficient to produce a reduced sulfhydryl group. In certain aspects, the reducing agent is selected from cysteamine hydrochloride, 2-mercaptoethanol, dithiothreitol (DTT), 2-mercaptoethylamine, tris(2-carboxyl)phosphine (TCEP), cysteine HCl, N-ethylmaleimide, Nacystelyn, dornase alfa, thymosin β4, guaifenesin TCEP HCl, and any combination thereof. Reaction conditions for such reducing agents are known in the art and may be optimized, e.g., to promote selectivity or "bias" the reduction of the cysteine(s) present in the C-terminal extension as opposed to the cysteine residues present in the parental antibody (e.g., the cysteine residues that participate in disulfide bonding between $C_L$ and $C_H1$ of the light and heavy chains, and/or between the hinge regions of the heavy chains). An alternative embodiment of the invention does not require a reduction step as the cysteine within the light chain extension is already in a reduced state as a synthesis product.

Preferential reduction of the cysteine(s) of the C-terminal amino acid extension over one or more cysteine residues outside the C-terminal amino acid extension (or exclusive reduction of the cysteine(s) of the C-terminal amino acid extension) may be achieved by selection of suitable reduction conditions. In certain aspects, suitable reduction conditions include suitable selection of one or more of the following: a mild reducing agent and/or a reducing agent having a steric bulk that confers upon the reducing agent a preference for reducing a cysteine of the C-terminal amino acid extension; concentrations of the reducing agent and substrate; the temperature at which the reduction reaction is carried out, the pH of the reduction reaction mixture; the buffer used in the reduction reaction; and/or conditions under which the cells expressing the extended C-terminal light chain polypeptides are cultured (e.g., to obtain free thiol on the C-terminal extension and/or to generate readily reduced intermolecular disulfides).

Pharmaceutical Compositions

As summarized above, the present disclosure provides compositions. Compositions of the present disclosure may include any of the antibodies, conjugates, nucleic acids, vectors, and/or host cells described above. Aspects of the present disclosure include pharmaceutical compositions. In certain embodiments, the pharmaceutical compositions include any of the antibodies described elsewhere herein (e.g., an antibody that includes a light chain polypeptide including a C-terminal amino acid extension that includes a cysteine residue as described above) or any of the conjugates described elsewhere herein (e.g., a conjugate that includes an antibody component having a light chain polypeptide including a C-terminal amino acid extension that includes a cysteine residue as described above), and a pharmaceutically acceptable excipient. The antibody or conjugate present in the pharmaceutical compositions may include any of the features described above with respect to the antibodies of the present disclosure or the conjugates of the present disclosure, in any combination. For example, the C-terminal extension of the antibody, or antibody portion of the conjugate, may include any of the C-terminal extension features described above with respect to the length of the extension, the amino acid makeup of the extension, the number of spacers in the extension and amino acid sequences thereof, extension configurations based on combinations of one or more spacers and one or more cysteine residues, and any other aspects of the C-terminal extensions described above and elsewhere herein.

The pharmaceutical compositions generally include a therapeutically effective amount of an antibody or conjugate of the present disclosure. An effective amount may be administered in one or more administrations.

The antibodies or conjugates of the present disclosure may be administered to the patient using any convenient means capable of resulting in the desired therapeutic effect or diagnostic effect. Thus, the antibody or conjugate can be incorporated into a variety of formulations for therapeutic administration. More particularly, the antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, injections, inhalants and aerosols.

Formulations of the antibodies or conjugates of the present disclosure suitable for administration to a patient (e.g., suitable for human administration) are generally sterile and may further be free of detectable pyrogens or other contaminants contraindicated for administration to a patient according to a selected route of administration.

In pharmaceutical dosage forms, the antibody can be administered in the form of their pharmaceutically acceptable salts, or they may also be used alone or in appropriate association, as well as in combination, with other pharmaceutically active compounds. The following methods and excipients are merely examples and are in no way limiting.

For oral preparations, the antibodies or conjugates can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The antibodies or conjugates can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions of the present disclosure may be prepared by mixing the antibody or conjugate having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

Example antibody or conjugate concentrations in a pharmaceutical composition according the present disclosure may range from about 1 mg/mL to about 200 mg/ml or from about 50 mg/mL to about 200 mg/mL, or from about 150 mg/mL to about 200 mg/mL.

An aqueous formulation of the antibody or conjugate may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody or conjugate formulation to modulate the tonicity of the formulation. Example tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 mM.

A surfactant may also be added to the antibody or conjugate formulation to reduce aggregation of the formulated antibody or conjugate and/or minimize the formation of particulates in the formulation and/or reduce adsorption. Example surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Example concentrations of surfactant may range from about 0.001% to about 1% w/v.

A lyoprotectant may also be added in order to protect the active ingredient (e.g. the antibody or conjugate) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In certain aspects, the formulation includes an antibody or conjugate of the present disclosure, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, the formulation can be a liquid (e.g., an aqueous solution or emulsion) or lyophilized formulation thereof, suitable for parenteral administration, and can comprise: about 1 mg/mL to about 200 mg/mL of a subject antibody or conjugate; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

An antibody or conjugate of the present disclosure can be utilized in an aerosol formulation to be administered via inhalation. The antibody can be formulated into pressurized acceptable propellants such as dichlorodifluoromethane, propane, nitrogen and the like.

Unit dosage forms for oral administration such as syrups, elixirs, and suspensions may be provided wherein each dosage unit, for example, teaspoonful, tablespoonful, or tablet, contains a predetermined amount of the composition containing one or more inhibitors. Similarly, unit dosage forms for injection or intravenous administration may comprise the antibody or conjugate in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the antibody or conjugate of interest may depend on the particular antibody employed and the effect to be achieved, and the pharmacodynamics associated with each antibody in the host.

In certain aspects, the pharmaceutical composition (optionally provided in unit dosage form) includes an antibody or conjugate of the present disclosure present at a concentration of from about 10 mg/mL to about 1000 mg/mL, e.g., from about 25 mg/mL to about 500 mg/mL, from about 50 mg/mL to about 250 mg/mL, from about 75 mg/mL to about 200 mg/mL, or from about 100 mg/mL to about 150 mg/mL (e.g., about 125 mg/mL).

In some embodiments, the antibody or conjugate is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release.

A suitable dosage can be determined by an attending physician or other qualified medical personnel, based on various clinical factors. As is well known in the medical arts, dosages for any one patient depend upon many factors, including the patient's size, body surface area, age, the particular antibody or conjugate to be administered, sex of the patient, time, and route of administration, general health, and other drugs being administered concurrently. An antibody or conjugate of the present disclosure may be administered in amounts between 1 ng/kg body weight and 25 mg/kg body weight per dose, e.g. between 0.1 mg/kg body weight to 10 mg/kg body weight, e.g. between 0.5 mg/kg body weight to 8 mg/kg body weight, e.g. between 1 mg/kg body weight to 6 mg/kg body weight, e.g. between 2 mg/kg body weight to 5 mg/kg body weight; however, doses below or above these example ranges are envisioned, especially considering the aforementioned factors. If the regimen is a continuous infusion, it can also be in the range of 1 μg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Conventional and pharmaceutically acceptable routes of administration include intravenous, intra-arterial, intramuscular, intranasal, intra-tracheal, subcutaneous, intradermal, topical application, nasal, oral, and other enteral and parenteral routes of administration. Routes of administration may be combined, if desired, or adjusted depending upon the antibody or conjugate and/or the desired effect. The pharmaceutical composition can be administered in a single dose or in multiple doses. In some embodiments, the composition is administered intravenously. In some embodiments, the composition is administered orally. In some embodiments, the composition is administered via an inhalational route. In some embodiments, the composition is administered intranasally. In some embodiments, the composition is administered locally. In some embodiments, the composition is administered intra-cranially.

Methods of Treatment

The present disclosure provides methods of treating diseases or disorders. The methods may include administering to a patient in need thereof a therapeutically effective amount of any of the antibodies, conjugates, or pharmaceutical compositions described elsewhere herein. The antibody or conjugate may be administered alone (e.g., in monotherapy) or in combination (e.g., in combination therapy) with one or more additional therapeutic agents.

In some embodiments, an effective amount of the antibody or conjugate is an amount that, when administered alone (e.g., in monotherapy) or in combination (e.g., in combination therapy) with one or more additional therapeutic agents, in one or more doses, is effective to reduce the symptoms of a disease or disorder in an individual by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the symptoms in the individual in the absence of treatment with the antibody or conjugate.

The methods of the present disclosure may be employed to treat any diseases or disorders of interest. In certain aspects, the methods are employed to treat cancer. For example, in some embodiments, an antibody or conjugate of the present disclosure inhibits growth, metastasis and/or invasiveness of a cancer cell(s) in a host when the antibody or conjugate is administered in an effective amount. By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a primary tumor, a metastatic tumor, and the like.

In certain aspects, when the methods are for treatment of cancer, the antibody or antibody component of the conjugate specifically binds to an antigen on the surface of a cancer cell. The terms "antigen" and "epitope" are well understood in the art and refer to the portion of a macromolecule (e.g., a polypeptide) which is specifically recognized by a component of the immune system, e.g., an antibody or a T-cell antigen receptor. As used herein, the term "antigen" encompasses antigenic epitopes, e.g., fragments of an antigen which are antigenic epitopes. Haptens are also examples of antigens. Epitopes can be recognized by antibodies in solution, e.g. free from other molecules. Epitopes can be recognized by T-cell antigen receptor when the epitope is associated with a class I or class II major histocompatibility complex molecule.

Antigens of interest in the context of cancer treatment include tumor-specific antigens, e.g., antigens present on the surface of malignant cells and not present on non-malignant cells. In other aspects, the antigen bound by the antibody is a tumor-associated antigen. By "tumor-associated antigen" is meant an antigen expressed on malignant cells with limited expression on cells of normal tissues, antigens that are expressed at much higher density on malignant versus normal cells, or antigens that are developmentally expressed.

Any tumor-associated antigen or tumor-specific antigen may be targeted by an antibody or conjugate of the present disclosure. In certain aspects, when the methods of the present disclosure are for treatment of cancer, the antigen specifically bound by the antibody or antibody component of a conjugate of the present disclosure may include, but is not limited to, HER2, CD19, CD22, CD30, CD33, CD56, CD66/CEACAM5, CD70, CD74, CD79b, CD138, Nectin-4, Mesothelin, Transmembrane glycoprotein NMB (GPNMB), Prostate-Specific Membrane Antigen (PSMA), SLC44A4, CA6, CA-IX, or any other tumor-associated or tumor-specific antigens of interest.

By "specific binding" or "specifically binds" in the context of a characteristic of an antibody refers to the ability of an antibody to preferentially bind to a particular antigen that is present in a homogeneous mixture of different antigens. In certain embodiments, a specific binding interaction will discriminate between desirable and undesirable antigens (or "target" and "non-target" antigens) in a sample or organism (e.g., a human), in some embodiments more than about 10 to 100-fold or more (e.g., more than about 1000- or 10,000-fold). In certain embodiments, the affinity between an antibody and antigen when they are specifically bound in an antibody-antigen complex is characterized by a KD (dissociation constant) of less than $10^{-6}$ M, less than $10^{-7}$M, less than $10^{-8}$M, less than $10^{-9}$M, less than $10^{-11}$ M, less than $10^{-11}$M, or less than about $10^{-12}$M or less.

Cancers which may be treated using the methods of the present disclosure include, but are not limited to, solid tumors, breast cancer, prostate cancer, pancreatic cancer, colorectal carcinoma, renal cell carcinoma, Hodgkin's lymphoma, Non-Hodgkin's lymphoma, anaplastic large cell lymphoma, acute myelogenous leukemia, multiple myeloma, and any other type of cancer which may be treated using an antibody-based or antibody-conjugate-based therapy.

Kits

The present disclosure also provides kits. According to certain embodiments, the kits may include any of the antibodies, conjugates, or pharmaceutical compositions of the present disclosure having any of the features as described elsewhere herein. Alternatively, or additionally, the kits may include any reagents useful for producing an antibody of the present disclosure or light chain polypeptide thereof, or any of the conjugates of the present disclosure. For example, the kit may include a nucleic acid that encodes an antibody light chain polypeptide that include a cysteine-containing C-terminal amino acid extension. Such kits may include, e.g., competent cells or cells already harboring nucleic acids encoding one or more antibody light and/or heavy chain polypeptides, a reducing agent for reducing the sulfhydryl group of a cysteine residue in the C-terminal light chain polypeptide extension, a linker for conjugating an agent to a reduced sulfhydryl of a cysteine residue, an agent (which may be attached to a linker or separate from a linker), reagents, buffers, purification columns, etc. that find use in producing an antibody or conjugate of the present disclosure, or any combinations thereof. The kits find use, e.g., in enabling one to practice the methods of the present disclosure, such as the methods of treating a disease or disorder, methods of making antibody light chain polypeptides, and/or methods of making antibody conjugates.

The kits for practicing the methods may include one or more pharmaceutical compositions that include the antibodies or conjugates described herein. As such, the kits may include a single pharmaceutical composition present as one or more unit dosages. In yet other embodiments, the kits may include two or more separate pharmaceutical compositions.

Components of the kits may be present in separate containers, or multiple components may be present in a single container. In certain embodiments, it may be convenient to provide the components in a lyophilized form, so that they are ready to use and can be stored conveniently at room temperature.

In addition to the above-mentioned components, a kit of the present disclosure may further include instructions for using the components of the kit, e.g., to treat a disease or disorder using an antibody or conjugate of the present disclosure, or to make an antibody or conjugate of the present disclosure. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXAMPLES

Example 1

Cloning of Nucleic Acids Encoding Antibodies Having C-Terminal Light Chain Polypeptide Cysteine-Containing Extensions To generate human IgG1C and human IgGkC cloning vectors the human IgGC and IgkC regions were cloned into a pTT5 vector (FIG. 1.). To facilitate cloning of variable regions in frame with the constant regions, a restriction site was introduced into the 5' end of the constant region. The heavy chain constant region sequence was changed from GCC TCC to GCT AGC which introduced a NheI restriction site while maintaining the original amino acid sequence. The light chain polypeptide constant region sequence was changed from CGA ACT to CGT ACG to generate a BsiWI restriction site while maintaining the original amino acid sequence. The changes were introduced by designing mismatch PCR primers purchased from Operon-Eurofins. Since the pTT5 vector did not contain a BsiWI site, the IgkC 5' primer was designed with a 5' NheI overhang to facilitate cloning into the vector. The 3' primers were designed with a BamHI restriction site 3' of the stop codon.

To generate a cDNA template for the PCR reactions, RNA was extracted from human peripheral blood using Qiagen® RNeasy® miniprep kits and cDNA was synthesized using an oligodT primer and Superscript® III reverse transcriptase from Invitrogen™.

Following PCR, the fragments and the vectors were digested using the relevant restriction enzymes and separated on a 1% agarose gel. The digested fragments were extracted from the gel using Qiagen gel extraction kit and ligated into the vector using T4 DNA ligase (New England Biolabs). Competent DH5α *E-coli* (Invitrogen) were transformed and single-cell colonies were grown at 37° C. over night on ampicillin selective LB plates. To isolate the plasmids, single cells colonies were inoculated into liquid LB-ampicillin media, grown overnight at 37° C., and plasmids were isolated using Qiagen® QIAprep® spin miniprep kit. The clones were screened by miniprep DNA digests, and verified by sequence analysis using Geneious sequence alignment, assembly and analysis software from Biomatters. Primer sequences used for the cloning are provided in Table 1.

TABLE 1

| IgGC and IgkC cloning primers | | | |
|---|---|---|---|
| hIgGC_for_NheI | SEQ ID NO: 75 | ATTAGCTAGCACCAAGG GCCCATCGGTCTTC |
| hIgGC_rev_BamHI | SEQ ID NO: 76 | GATATGGATCCTCATTT ACCCGGAGACAGGGA |
| hKC_for_NheI_BsiW | SEQ ID NO: 77 | TATGCTAGCGTCGTACG GTGGCTGCACCATCTGT CTTCATC |
| hKC_rev_BamHI | SEQ ID NO: 78 | GATGGATCCCTAACACT CTCCCCTGTTGAAGC |

To generate ERBB specific antibodies the 4D5 humanized variant 8, herceptin V-genes were synthesized as gBlocks® gene fragments from IDT® (Integrated DNA Technologies). The sequences synthesized are provided in Table 2.

TABLE 2

| Herceptin V sequences | | |
|---|---|---|
| Herceptin VH amino acid sequence | SEQ ID NO: 79 | MEFGLSWVFLVAILKGVQCEVQLVESGGGLVQ PGGSLRLSCAASGFNIKDTYIHWVRQAPGKGLE WVARIYPTNGYTRYADSVKGRFTISADT SKNTA YLQMNSLRAEDTAVYYCSRWGGDGFYAMDY WGQGTLVTVSSASTKGPSV |
| Herceptin VH nucleotide sequence | SEQ ID NO: 80 | AGTCAGTCGGAATTCGCCACCATGGAGTTTGG GCTGAGCTGGGTTTTCCTTGTTGCTATTTTAAA AGGTGTCCAGTGTGAGGTGCAGCTGGTGGAG AGCGGCGGCGGCCTGGTGCAGCCCGGCGGCA GCCTGAGACTGAGCTGCGCCGCCAGCGGCTTC |

TABLE 2 -continued

| Herceptin V sequences | | |
|---|---|---|
| | | AACATCAAGGACACCTACATCCACTGGGTGA GACAGGCCCTGGCAAGGGCCTGGAGTGGGT GGCCAGAATCTACCCCACCAACGGCTACACC AGATACGCCGACAGCGTGAAGGGCAGATTCA CCATCAGCGCCGACACCAGCAAGAACACCGC CTACCTGCAGATGAACAGCCTGAGAGCCGAG GACACCGCCGTGTACTACTGCAGCAGATGGG GCGGCGACGGCTTCTACGCCATGGACTACTGG GGCCAGGGCACCCTGGTGACCGTGAGCAGCG CTAGCACCAAGGGCCCATCGGTCTT |
| Herceptin Vk amino acid sequence | SEQ ID NO: 81 | MDMRVPAQLLGLLLLWLRGARCDIQMTQSPSS LSASVGDRVTITCRASQDVNTAVAWYQQKPGK APKLLIYSASFLYSGVPSRFSGSRSGTDFTLTISSL QPEDFATYYCQQHYTTPPTFGQGTKVEIKRTVA APSV |
| Herceptin Vk nucleotide sequence | SEQ ID NO: 82 | AGTCAGTCGGAATTCGCTACCATGGACATGA GGGTCCCCGCTCAGCTCCTGGGGCTCCTGCTA CTCTGGCTCCGAGGTGCCAGATGTGACATCCA GATGACCCAGAGCCCCAGCAGCCTGAGCGCC AGCGTGGGCGACAGAGTGACCATCACCTGCA GAGCCAGCCAGGACGTGAACACCGCCGTGGC CTGGTACCAGCAGAAGCCCGGCAAGGCTCCC AAGCTGCTGATCTACAGCGCCAGCTTCCTGTA CAGCGGCGTGCCCAGCAGATTCAGCGGCAGC AGAAGCGGCACCGACTTCACCCTGACCATCA GCAGCCTGCAGCCCGAGGACTTCGCCACATAC TACTGCCAGCAGCACTACACCACCCCTCCCAC CTTCGGCCAGGGCACCAAGGTGGAGATCAAG CGTACGGTGGCTGCACCATCTGTCT |

The fragments were cloned into the mentioned constant region pTT5 vectors using EcoRI and NheI digests for the heavy chain and EcoRI and BsiWI digests for the light chain polypeptide as described above.

To add a (GGGSC)x extension to the light chain polypeptide, where x is the number of repeats added, 3' end primers were designed and ordered from Eurofins MWG Operon with the desired sequences, shown in Table 3. Standard cloning procedures were performed using the previously described herceptin VK constructs as templates in the PCR reaction. To generate the 4 cysteine construct a two-step overlapping approach was taken where the primer Igk_rev_3_cys was used in the first PCR, followed by amplification using the primer Igk_rev_4_cys Bam and the PCR product from the first PCR as template. The 5' primer used in all the reactions was pTT5_for (Table 3). The PCR fragments were digested, cloned and analyzed as described above.

TABLE 3

| Cloning primers used to add cysteines to light chain polypeptide C-terminus | | |
|---|---|---|
| IgK_rev_1_cys_Bam | SEQ ID NO: 83 | ACG TGG ATC CTC AAC AGC TTC CCC CTC CAC ACT CTC CCC TGT TGA AGC |
| IgK_rev_2_cys_Bam | SEQ ID NO: 84 | ACG TGG ATC CTC AAC AGC TTC CCC CTC CGC AGC TTC CTC CTC CAC ACT CTC CCC TGT TGA AGC |
| IgK_rev_3_cys_Bam | SEQ ID NO: 85 | ACG TGG ATC CTC AAC AGC TTC CCC CTC CGC AGC TTC CTC CTC CGC AAG ATC CTC CTC CAC ACT CTC CCC TGT TGA AGC |
| IgK_rev_3_cys | SEQ ID NO: 86 | ACA GCT TCC CCC TCC GCA GCT TCC TCC TCC GCA AGA TCC TCC TCC ACA CTC TCC CCT GTT GAA GC |
| IgK_rev_4_cys_Bam | SEQ ID NO: 87 | ACG TGG ATC CTC AGC AGC TTC CTC CTC CAC AGC TTC CCC CTC CGC AGC T |
| pTT5_for | SEQ ID NO: 88 | TGC GCT AAG ATT GTC AGT TTC CA |

Example 2

Antibody Production and Purification

Qiagen maxipreps of the plasmids generated in Example 1 above were performed to isolate transfection ready plasmids. HEK293 cells were co-transfected with the Herceptin heavy chain and the Herceptin light chain-cys constructs using 293 fectin (Invitrogen). The cells were grown in Freestyle 293 expression media (Gibco) supplemented with 0.1% Pluronic F68 (Gibco) solution for 5 days. 24 hours post transfection the cells were supplemented with 0.5% tryptone. Supernatants were collected and the secreted antibodies were purified using a protein A sepharose batch gravity protocol (GEHealthcare) followed by buffer exchange into PBS PH 7.4 using an Amicon® Ultra 15 filter with a 30 kDa MW cutoff (Millipore).

Example 3

Reduction of Herceptin-VLCysX Disulfide Bonds

Samples (1-5 mg) of Herceptin and Herceptin-VLCysX (X=1, 2 or 4) in PBS were applied to Zeba™ spin columns (Pierce, catalogue #87767) preconditioned with 100 mM phosphate, 50 mM NaCl, 2 mM DTPA, pH 6.1 and buffer exchanged according to the manufacturer's instructions. The eluates were assayed using a bicinchoninic acid assay (Pierce, #23225) using Herceptin as a standard to establish protein concentration, and with Ellman's reagent using cysteine as a standard to establish the absence of free thiol groups.

Herceptin or Herceptin VLCysX (5-30 µM in 100 mM phosphate, 50 mM NaCl, 2 mM DTPA, pH 6.1) was reduced by addition of cysteamine hydrochloride (from 5 to 10 mM) from a 1.0 M stock in the same buffer and incubation for 40-180 minutes at either room temperature or 37° C. After cooling to room temperature cysteamine was removed from the reaction mixture by passage over a Zeba™ spin column (40 KDa MWCO) preconditioned with 100 mM phosphate, 50 mM NaCl, 2 mM DTPA, pH 6.1. In order to ensure excess cysteamine had been removed, the eluate was assayed with Ellman's reagent employing a standard curve generated by assay of cysteine serial dilutions. This assay also provided some measure of the average thiol content per protein.

Example 4

Conjugation of Herceptin-VLCysX to a Cytotoxic Agent

After cooling the eluates from Example 3 above on ice, maleimide toxin (toxin 1 or toxin 2) was added from a 10 mM DMSO stock solution (generally 2.0 eq. per thiol, with an equal amount added to the reduced Herceptin control (Herceptin-toxin 2)). The conjugation reaction was allowed to proceed for between 30 and 70 minutes on ice before purification and buffer exchange in to 20 mM sodium citrate, pH 5.5. The purified conjugates were sterile filtered (Costar® Spin-X® 0.22 um centrifugal filters, #8161) and assayed using the BCA reagent for total protein content.

"Toxin 1" as used herein is MC-vc-PABC-toxin, where the toxin is (S,E)-N-(4-(aminomethyl)benzylsulfonyl)-2,5-dimethyl-4-((S)-N,3,3-trimethyl-2-((S)-3-methyl-2-(methylamino)-3-phenylbutanamido)butanamido)hex-2-enamide.

"Toxin 2" as used herein is MC-vc-toxin, where the toxin is (S,E)-N-(4-aminobenzylsulfonyl)-2,5-dimethyl-4-((S)-N,3,3-trimethyl-2-((S)-3-methyl-2-(methylamino)-3-phenylbutanamido)butanamido)hex-2-enamide.

"Toxin 3" as used herein is MT-vc-toxin, where the toxin is (S,E)-N-(4-aminophenylsulfonyl)-2,5-dimethyl-4-((S)-N,3,3-trimethyl-2-((S)-3-methyl-2-(methylamino)-3-phenylbutanamido)butanamido)hex-2-enamide.

"Toxin 4" as used herein is MP(T-vc-toxin)$_2$, where the toxin is (S,E)-N-(4-aminophenylsulfonyl)-2,5-dimethyl-4-((S)-N,3,3-trimethyl-2-((S)-3-methyl-2-(methylamino)-3-phenylbutanamido)butanamido)hex-2-enamide.

"Toxin 5" as used herein is MT-vc-PABC-toxin, where the toxin is (S,E)-N-(4-(aminomethyl)benzylsulfonyl)-2,5-dimethyl-4-((S)-N,3,3-trimethyl-2-((S)-3-methyl-2-(methylamino)-3-phenylbutanamido)butanamido)hex-2-enamide.

"Toxin 6" as used herein is MT-vc-toxin, where the toxin is:

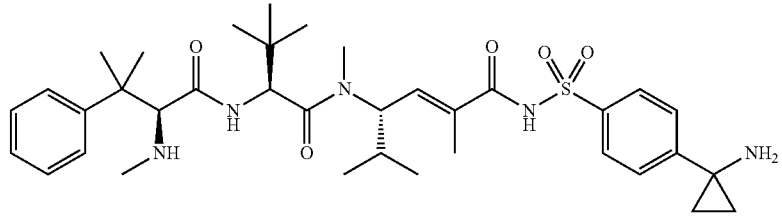 [SMILES: CN[C@H](C(=O)N[C@H](C(=O)N(C)[C@H](/C=C(\C)C(=O)NS(=O)(=O)c1ccc(C2(N)CC2)cc1)C(C)C)C(C)(C)C)C(C)(C)c1ccccc1]

Example 5

Testing the Effect of Herceptin VLCysX on Cancer Cell Viability

Figure 3:
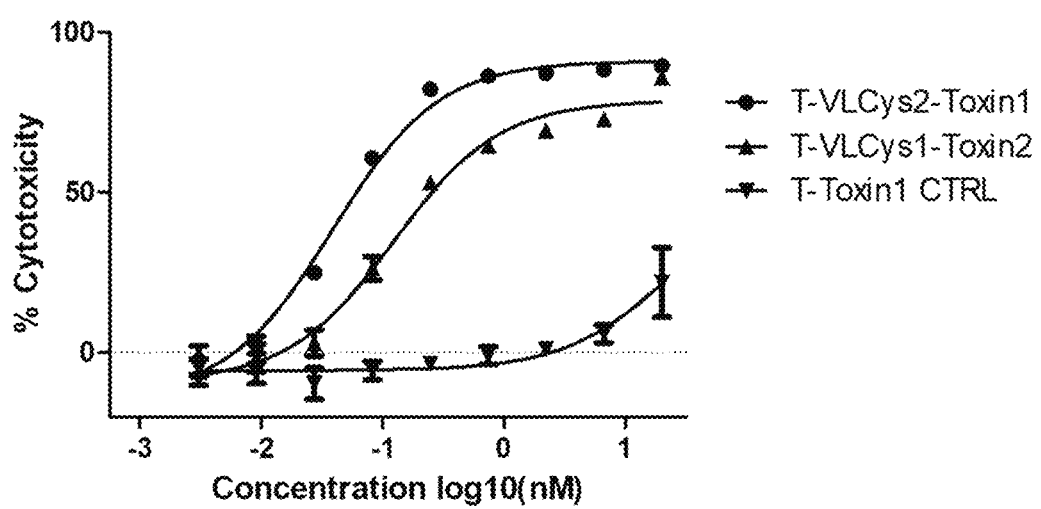
FIG. 3 provides cancer cell viability data for two example antibody conjugates according to embodiments of the present disclosure.

The antibody drug conjugates generated in Example 4 above were tested at varying concentrations against the Her2 positive human mammary carcinoma cell line HCC1954. On the day prior to adding compounds, HCC1954 cells (100 µL) were added to opaque-walled clear-bottomed 96-well tissue culture-treated microtiter plates using complete growth medium at a density of 2500 cells/100 µL of medium. The HCC1954 cells were incubated for one night at 37° C./5% CO2 to allow the cells to attach to the microtiter plate surface. Antibody drug conjugates were diluted in complete growth medium at five-times the final maximum concentration desired and compounds were then titrated 1:3 in the same medium, eight steps. A control with no compound (growth medium alone) was included on each microtiter plate in sextuplicate. The prepared compounds titrations were added (twenty-five µL/well) in triplicate to the HCC1954 cells. The cells and compound titrations were incubated at 37° C./5% CO2 for three or five nights. After the incubation, cell viability was measured using CellTiter-Glo® reagent by adding 30 µL of prepared CellTiter-Glo® to each assay well. The mixture was incubated for a minimum of twenty minutes prior to measurement of luminescence using a microplate luminometer (500 ms integration time). The collected relative luminescence units (RLU) are converted to % cytotoxicity using the growth medium alone control mentioned above (% Cytotoxicity=1−[Well RLU/average medium alone control RLU]). Data were fit to curves using non-linear regression methods available with Prism Graph Pad software. A graph showing the data from this study is provided in FIG. 3. The EC50 values of Her-VLCys2-toxin 2, Her-VLCys1-toxin 1 and Herceptin-toxin 2 are shown in Table 4.

TABLE 4

EC50 values of Her-VLCys2-toxin, Her-VLCys1-toxin and Herceptin-toxin

| | EC50 (nM) |
|---|---|
| Her-VLCys2-toxin 2 | 0.04 |
| Her-VLCys1-toxin 1 | 0.12 |
| Herceptin-toxin 2 | 22.68 |

Example 6

Cloning of Nucleic Acids Encoding Additional Antibodies Having C-Terminal Light Chain Polypeptide Cysteine-Containing Extensions To generate additional light chain extensions, synthetic gBlocks® gene fragments from IDT® were ordered with the desired sequence and cloned in frame into the Herceptin VK using a Gibson assembly cloning kit (New England Biolabs). All clones were sequence verified and analyzed as described above in Example 1.

Light chain amino acid sequences and the nucleic acid sequences encoding the same are provided in Table 5 below.

TABLE 5

Amino acid sequences for additional antibody light chains, and nucleic acid sequences encoding the same

| Name and SEQ ID NO | Description | Sequence (AA) |
|---|---|---|
| Herceptin-Igk-Ig extension1 SEQ ID NO: 104 | Herceptin VL and hIgk constant region (Km3 allotype) + a EPKSCDKTHTC tail (sequence from human IgG1 hinge) | RTVAAPSVFIFPPSDEQLKSG TASVVCLLNNFYPREAKVQ WKVDNALQSGNSQESVTEQ DSKDSTYSLSSTLTLSKADY EKHKVYACEVTHQGLSSPVT KSFNRGECEPKSCDKTHTC |
| Herceptin-Igk-Ig extension2 SEQ ID NO: 105 | Herceptin VL and hIgk constant region (Km3 allotype) + a EPKSCDKTHTCPPC tail (sequence from human IgG1 hinge) | RTVAAPSVFIFPPSDEQLKSG TASVVCLLNNFYPREAKVQ WKVDNALQSGNSQESVTEQ DSKDSTYSLSSTLTLSKADY EKHKVYACEVTHQGLSSPVT KSFNRGECEPKSCDKTHTCP PC |
| Herceptin-Igk-Ig extension3 SEQ ID NO: 106 | Herceptin VL and hIgk constant region (Km3 allotype) + a EPKSC tail (sequence from human IgG1 hinge) | RTVAAPSVFIFPPSDEQLKSG TASVVCLLNNFYPREAKVQ WKVDNALQSGNSQESVTEQ DSKDSTYSLSSTLTLSKADY EKHKVYACEVTHQGLSSPVT KSFNRGECEPKSC |
| Herceptin-Igk-Ig extension4 SEQ ID NO: 107 | Herceptin VL and hIgk constant region (Km3 allotype) + a ESKYGPPC tail (sequence from human IgG4 hinge) | RTVAAPSVFIFPPSDEQLKSG TASVVCLLNNFYPREAKVQ WKVDNALQSGNSQESVTEQ DSKDSTYSLSSTLTLSKADY EKHKVYACEVTHQGLSSPVT KSFNRGECESKYGPPC |
| Herceptin-Igk-Ig extension5 SEQ ID NO: 108 | Herceptin VL and hIgk constant region (Km3 allotype) + a ERKCCVECPPC tail (sequence from human IgG2 hinge) | RTVAAPSVFIFPPSDEQLKSG TASVVCLLNNFYPREAKVQ WKVDNALQSGNSQESVTEQ DSKDSTYSLSSTLTLSKADY EKHKVYACEVTHQGLSSPVT KSFNRGECERKCCVECPPC |
| Herceptin-Igk-Ig extension6 SEQ ID NO: 109 | Herceptin VL and hIgk constant region (Km3 allotype) + a ERKC tail (sequence from human IgG2 hinge) | RTVAAPSVFIFPPSDEQLKSG TASVVCLLNNFYPREAKVQ WKVDNALQSGNSQESVTEQ DSKDSTYSLSSTLTLSKADY EKHKVYACEVTHQGLSSPVT KSFNRGECERKC |
| Herceptin-Igk-Ig extension7 SEQ ID NO: 110 | Herceptin VL and hIgk constant region (Km3 allotype) + a DVITMDPKDNC tail (sequence from human TCRg hinge) | RTVAAPSVFIFPPSDEQLKSG TASVVCLLNNFYPREAKVQ WKVDNALQSGNSQESVTEQ DSKDSTYSLSSTLTLSKADY EKHKVYACEVTHQGLSSPVT KSFNRGECDVITMDPKDNC |
| Herceptin-Igk-Ig extension8 SEQ ID NO: 111 | Herceptin VL and hIgk constant region (Km3 allotype) + a | RTVAAPSVFIFPPSDEQLKSG TASVVCLLNNFYPREAKVQ |

TABLE 5-continued

Amino acid sequences for additional antibody light chains, and nucleic acid sequences encoding the same

| | | |
|---|---|---|
| | DHVKPKETENTKQPSKSCHKPK tail (sequence from human TCRd hinge) | WKVDNALQSGNSQESVTEQ DSKDSTYSLSSTLTLSKADY EKHKVYACEVTHQGLSSPVT KSFNRGECDHVKPKETENTK QPSKSCHKPK |
| Herceptin-Igk-Ig extension9 SEQ ID NO: 112 | Herceptin VL and hIgk constant region (Km3 allotype) + a ESSC tail (sequence from human TCRa hinge) | RTVAAPSVFIFPPSDEQLKSG TASVVCLLNNFYPREAKVQ WKVDNALQSGNSQESVTEQ DSKDSTYSLSSTLTLSKADY EKHKVYACEVTHQGLSSPVT KSFNRGECESSC |
| Herceptin-Igk-Ig extension10 SEQ ID NO: 113 | Herceptin VL and hIgk constant region (Km3 allotype) + a ESSCDVKLV tail (sequence from human TCRa hinge) | RTVAAPSVFIFPPSDEQLKSG TASVVCLLNNFYPREAKVQ WKVDNALQSGNSQESVTEQ DSKDSTYSLSSTLTLSKADY EKHKVYACEVTHQGLSSPVT KSFNRGECESSCDVKLV |
| Herceptin-Igk-Ig extension11 SEQ ID NO: 114 | Herceptin VL and hIgk constant region (Km3 allotype) + a DHVKPKETENTKQPSKSC tail (sequence from human TCRd hinge) | RTVAAPSVFIFPPSDEQLKSG TASVVCLLNNFYPREAKVQ WKVDNALQSGNSQESVTEQ DSKDSTYSLSSTLTLSKADY EKHKVYACEVTHQGLSSPVT KSFNRGECDHVKPKETENTK QPSKSC |
| Herceptin-Igk-Ig extension12 SEQ ID NO: 115 | Herceptin VL and hIgk constant region (Km3 allotype) + a DVITMDPKDNCSKDAN tail (sequence from human TCRg hinge) | RTVAAPSVFIFPPSDEQLKSG TASVVCLLNNFYPREAKVQ WKVDNALQSGNSQESVTEQ DSKDSTYSLSSTLTLSKADY EKHKVYACEVTHQGLSSPVT KSFNRGECDVITMDPKDNCS KDAN |

| Name | Description | Sequence (NT) |
|---|---|---|
| Herceptin-Igk-Ig extension1 SEQ ID NO: 116 | Herceptin VL and hIgk constant region (Km3 allotype) + a EPKSCDKTHTC tail (sequence from human IgG1 hinge) | GGCCAGGGCACCAAGGTGG AGATCAAGCGTACGGTGGC TGCACCATCTGTCTTCATCT TCCCGCCATCTGATGAGCA GTTGAAATCTGGAACTGCC TCTGTTGTGTGCCTGCTGAA TAACTTCTATCCCAGAGAG GCCAAAGTACAGTGGAAGG TGGATAACGCCCTCCAATC GGGTAACTCCCAGGAGAGT GTCACAGAGCAGGACAGCA AGGACAGCACCTACAGCCT CAGCAGCACCCTGACGCTG AGCAAAGCAGACTACGAG AAACACAAAGTCTACGCCT GCGAAGTCACCCATCAGGG CCTGAGCTCGCCCGTCACA AAGAGCTTCAACAGGGGAG AGTGTGAGCCAAAATCCTG TGACAAGACTCACACGTGT TGAGGATCCCCCGACCTCG ACCTCTGGCT |
| Herceptin-Igk-Ig extension2 SEQ ID NO: 117 | Herceptin VL and hIgk constant region (Km3 allotype) + a EPKSCDKTHTCPPC tail (sequence from human IgG1 hinge) | GGCCAGGGCACCAAGGTGG AGATCAAGCGTACGGTGGC TGCACCATCTGTCTTCATCT TCCCGCCATCTGATGAGCA GTTGAAATCTGGAACTGCC TCTGTTGTGTGCCTGCTGAA TAACTTCTATCCCAGAGAG GCCAAAGTACAGTGGAAGG TGGATAACGCCCTCCAATC GGGTAACTCCCAGGAGAGT GTCACAGAGCAGGACAGCA AGGACAGCACCTACAGCCT CAGCAGCACCCTGACGCTG AGCAAAGCAGACTACGAG AAACACAAAGTCTACGCCT GCGAAGTCACCCATCAGGG |

TABLE 5 -continued

Amino acid sequences for additional antibody light chains, and nucleic acid sequences encoding the same

| | | |
|---|---|---|
| | | CCTGAGCTCGCCCGTCACA<br>AAGAGCTTCAACAGGGGAG<br>AGTGTGAGCCTAAGTCATG<br>CGACAAGACCCACACCTGT<br>CCACCTTGTTGAGGATCCC<br>CCGACCTCGACCTCTGGCT |
| Herceptin-Igk-Ig extension3<br>SEQ ID NO: 118 | Herceptin VL and hIgk constant region (Km3 allotype) + a EPKSC tail (sequence from human IgG1 hinge) | GGCCAGGGCACCAAGGTGG<br>AGATCAAGCGTACGGTGGC<br>TGCACCATCTGTCTTCATCT<br>TCCCGCCATCTGATGAGCA<br>GTTGAAATCTGGAACTGCC<br>TCTGTTGTGTGCCTGCTGAA<br>TAACTTCTATCCCAGAGAG<br>GCCAAAGTACAGTGGAAGG<br>TGGATAACGCCCTCCAATC<br>GGGTAACTCCCAGGAGAGT<br>GTCACAGAGCAGGACAGCA<br>AGGACAGCACCTACAGCCT<br>CAGCAGCACCCTGACGCTG<br>AGCAAAGCAGACTACGAG<br>AAACACAAAGTCTACGCCT<br>GCGAAGTCACCCATCAGGG<br>CCTGAGCTCGCCCGTCACA<br>AAGAGCTTCAACAGGGGAG<br>AGTGTGAACCAAAGTCCTG<br>TTGAGGATCCCCCGACCTC<br>GACCTCTGGCT |
| Herceptin-Igk-Ig extension4<br>SEQ ID NO: 119 | Herceptin VL and hIgk constant region (Km3 allotype) + a ESKYGPPC tail (sequence from human IgG4 hinge) | GGCCAGGGCACCAAGGTGG<br>AGATCAAGCGTACGGTGGC<br>TGCACCATCTGTCTTCATCT<br>TCCCGCCATCTGATGAGCA<br>GTTGAAATCTGGAACTGCC<br>TCTGTTGTGTGCCTGCTGAA<br>TAACTTCTATCCCAGAGAG<br>GCCAAAGTACAGTGGAAGG<br>TGGATAACGCCCTCCAATC<br>GGGTAACTCCCAGGAGAGT<br>GTCACAGAGCAGGACAGCA<br>AGGACAGCACCTACAGCCT<br>CAGCAGCACCCTGACGCTG<br>AGCAAAGCAGACTACGAG<br>AAACACAAAGTCTACGCCT<br>GCGAAGTCACCCATCAGGG<br>CCTGAGCTCGCCCGTCACA<br>AAGAGCTTCAACAGGGGAG<br>AGTGTGAGTCTAAATATGG<br>ACCCCCGTGCTGAGGATCC<br>CCCGACCTCGACCTCTGGC<br>T |
| Herceptin-Igk-Ig extension5<br>SEQ ID NO: 120 | Herceptin VL and hIgk constant region (Km3 allotype) + a ERKCCVECPPC tail (sequence from human IgG2 hinge) | GGCCAGGGCACCAAGGTGG<br>AGATCAAGCGTACGGTGGC<br>TGCACCATCTGTCTTCATCT<br>TCCCGCCATCTGATGAGCA<br>GTTGAAATCTGGAACTGCC<br>TCTGTTGTGTGCCTGCTGAA<br>TAACTTCTATCCCAGAGAG<br>GCCAAAGTACAGTGGAAGG<br>TGGATAACGCCCTCCAATC<br>GGGTAACTCCCAGGAGAGT<br>GTCACAGAGCAGGACAGCA<br>AGGACAGCACCTACAGCCT<br>CAGCAGCACCCTGACGCTG<br>AGCAAAGCAGACTACGAG<br>AAACACAAAGTCTACGCCT<br>GCGAAGTCACCCATCAGGG<br>CCTGAGCTCGCCCGTCACA<br>AAGAGCTTCAACAGGGGAG<br>AGTGTGAGAGAAAGTGTTG<br>CGTAGAGTGTCCTCCCTGC<br>TGAGGATCCCCCGACCTCG<br>ACCTCTGGCT |

TABLE 5 -continued

Amino acid sequences for additional antibody light chains, and nucleic acid sequences encoding the same

| | | |
|---|---|---|
| Herceptin-Igk-Ig extension6 SEQ ID NO: 121 | Herceptin VL and hIgk constant region (Km3 allotype) + a ERKC tail (sequence from human IgG2 hinge) | GGCCAGGGCACCAAGGTGG AGATCAAGCGTACGGTGGC TGCACCATCTGTCTTCATCT TCCCGCCATCTGATGAGCA GTTGAAATCTGGAACTGCC TCTGTTGTGTGCCTGCTGAA TAACTTCTATCCCAGAGAG GCCAAAGTACAGTGGAAGG TGGATAACGCCCTCCAATC GGGTAACTCCCAGGAGAGT GTCACAGAGCAGGACAGCA AGGACAGCACCTACAGCCT CAGCAGCACCCTGACGCTG AGCAAAGCAGACTACGAG AAACACAAAGTCTACGCCT GCGAAGTCACCCATCAGGG CCTGAGCTCGCCCGTCACA AAGAGCTTCAACAGGGGAG AGTGTGAGCGGAAATGCTG AGGATCCCCCGACCTCGAC CTCTGGCT |
| Herceptin-Igk-Ig extension7 SEQ ID NO: 122 | Herceptin VL and hIgk constant region (Km3 allotype) + a DVITMDPKDNC tail (sequence from human TCRg hinge) | GGCCAGGGCACCAAGGTGG AGATCAAGCGTACGGTGGC TGCACCATCTGTCTTCATCT TCCCGCCATCTGATGAGCA GTTGAAATCTGGAACTGCC TCTGTTGTGTGCCTGCTGAA TAACTTCTATCCCAGAGAG GCCAAAGTACAGTGGAAGG TGGATAACGCCCTCCAATC GGGTAACTCCCAGGAGAGT GTCACAGAGCAGGACAGCA AGGACAGCACCTACAGCCT CAGCAGCACCCTGACGCTG AGCAAAGCAGACTACGAG AAACACAAAGTCTACGCCT GCGAAGTCACCCATCAGGG CCTGAGCTCGCCCGTCACA AAGAGCTTCAACAGGGGAG AGTGTGACGTTATAACCAT GGACCCGAAAGACAATTGC TGAGGATCCCCCGACCTCG ACCTCTGGCT |
| Herceptin-Igk-Ig extension8 SEQ ID NO 123 | Herceptin VL and hIgk constant region (Km3 allotype) + a DHVKPKETENTKQPSKSCHKPK tail (sequence from human TCRd hinge) | GGCCAGGGCACCAAGGTGG AGATCAAGCGTACGGTGGC TGCACCATCTGTCTTCATCT TCCCGCCATCTGATGAGCA GTTGAAATCTGGAACTGCC TCTGTTGTGTGCCTGCTGAA TAACTTCTATCCCAGAGAG GCCAAAGTACAGTGGAAGG TGGATAACGCCCTCCAATC GGGTAACTCCCAGGAGAGT GTCACAGAGCAGGACAGCA AGGACAGCACCTACAGCCT CAGCAGCACCCTGACGCTG AGCAAAGCAGACTACGAG AAACACAAAGTCTACGCCT GCGAAGTCACCCATCAGGG CCTGAGCTCGCCCGTCACA AAGAGCTTCAACAGGGGAG AGTGTGATCACGTGAAGCC CAAGGAGACGGAGAATAC CAAACAACCTTCCAAATCA TGTCACAAACCAAAATGAG GATCCCCCGACCTCGACCT CTGGCT |
| Herceptin-Igk-Ig extension9 SEQ ID NO: 124 | Herceptin VL and hIgk constant region (Km3 allotype) + a ESSC tail (sequence from human TCRa hinge) | GGCCAGGGCACCAAGGTGG AGATCAAGCGTACGGTGGC TGCACCATCTGTCTTCATCT TCCCGCCATCTGATGAGCA GTTGAAATCTGGAACTGCC TCTGTTGTGTGCCTGCTGAA |

TABLE 5 -continued

Amino acid sequences for additional antibody light chains, and nucleic acid sequences encoding the same

| | | |
|---|---|---|
| | | TAACTTCTATCCCAGAGAG<br>GCCAAAGTACAGTGGAAGG<br>TGGATAACGCCCTCCAATC<br>GGGTAACTCCCAGGAGAGT<br>GTCACAGAGCAGGACAGCA<br>AGGACAGCACCTACAGCCT<br>CAGCAGCACCCTGACGCTG<br>AGCAAAGCAGACTACGAG<br>AAACACAAAGTCTACGCCT<br>GCGAAGTCACCCATCAGGG<br>CCTGAGCTCGCCCGTCACA<br>AAGAGCTTCAACAGGGGAG<br>AGTGTGAAAGCAGCTGTTG<br>AGGATCCCCCGACCTCGAC<br>CTCTGGCT |
| Herceptin-Igk-Ig extension10<br>SEQ ID NO: 125 | Herceptin VL and hIgk constant region (Km3 allotype) + a ESSCDVKLV tail (sequence from human TCRa hinge) | GGCCAGGGCACCAAGGTGG<br>AGATCAAGCGTACGGTGGC<br>TGCACCATCTGTCTTCATCT<br>TCCCGCCATCTGATGAGCA<br>GTTGAAATCTGGAACTGCC<br>TCTGTTGTGTGCCTGCTGAA<br>TAACTTCTATCCCAGAGAG<br>GCCAAAGTACAGTGGAAGG<br>TGGATAACGCCCTCCAATC<br>GGGTAACTCCCAGGAGAGT<br>GTCACAGAGCAGGACAGCA<br>AGGACAGCACCTACAGCCT<br>CAGCAGCACCCTGACGCTG<br>AGCAAAGCAGACTACGAG<br>AAACACAAAGTCTACGCCT<br>GCGAAGTCACCCATCAGGG<br>CCTGAGCTCGCCCGTCACA<br>AAGAGCTTCAACAGGGGAG<br>AGTGTGAGAGCAGCTGCGA<br>TGTGAAATTGGTCTGAGGA<br>TCCCCCGACCTCGACCTCT<br>GGCT |
| Herceptin-Igk-Ig extension11<br>SEQ ID NO: 126 | Herceptin VL and hIgk constant region (Km3 allotype) + a DHVKPKETENTKQPSKSC tail (sequence from human TCRd hinge) | GGCCAGGGCACCAAGGTGG<br>AGATCAAGCGTACGGTGGC<br>TGCACCATCTGTCTTCATCT<br>TCCCGCCATCTGATGAGCA<br>GTTGAAATCTGGAACTGCC<br>TCTGTTGTGTGCCTGCTGAA<br>TAACTTCTATCCCAGAGAG<br>GCCAAAGTACAGTGGAAGG<br>TGGATAACGCCCTCCAATC<br>GGGTAACTCCCAGGAGAGT<br>GTCACAGAGCAGGACAGCA<br>AGGACAGCACCTACAGCCT<br>CAGCAGCACCCTGACGCTG<br>AGCAAAGCAGACTACGAG<br>AAACACAAAGTCTACGCCT<br>GCGAAGTCACCCATCAGGG<br>CCTGAGCTCGCCCGTCACA<br>AAGAGCTTCAACAGGGGAG<br>AGTGTGATCATGTGAAGCC<br>TAAAGAAACGGAGAATAC<br>AAAACAGCCCAGTAAGAGC<br>TGTTGAGGATCCCCCGACC<br>TCGACCTCTGGCT |
| Herceptin-Igk-Ig extension12<br>SEQ ID NO: 127 | Herceptin VL and hIgk constant region (Km3 allotype) + a DVITMDPKDNCSKDAN tail (sequence from human TCRg hinge) | GGCCAGGGCACCAAGGTGG<br>AGATCAAGCGTACGGTGGC<br>TGCACCATCTGTCTTCATCT<br>TCCCGCCATCTGATGAGCA<br>GTTGAAATCTGGAACTGCC<br>TCTGTTGTGTGCCTGCTGAA<br>TAACTTCTATCCCAGAGAG<br>GCCAAAGTACAGTGGAAGG<br>TGGATAACGCCCTCCAATC<br>GGGTAACTCCCAGGAGAGT<br>GTCACAGAGCAGGACAGCA<br>AGGACAGCACCTACAGCCT<br>CAGCAGCACCCTGACGCTG<br>AGCAAAGCAGACTACGAG |

TABLE 5 -continued

Amino acid sequences for additional antibody light chains, and nucleic acid sequences encoding the same

```
AAACACAAAGTCTACGCCT
GCGAAGTCACCCATCAGGG
CCTGAGCTCGCCCGTCACA
AAGAGCTTCAACAGGGGAG
AGTGTGATGTGATTACTAT
GGACCCAAAGGATAATTGC
AGTAAGGACGCTAATTGAG
GATCCCCCGACCTCGACCT
CTGGCT
```

Example 7

Antibody Production and Purification

Qiagen maxipreps of the clones generated in Example 6 were performed to isolate transfection ready plasmids. HEK293 cells were co-transfected with the Herceptin heavy chain and the Herceptin light chain-cys constructs using 293 fectin (Invitrogen). The cells were grown in Freestyle 293 expression media (Gibco) supplemented with 0.1% Pluronic F68 (Gibco) solution for 5 days. 24 hours post transfection the cells were supplemented with 0.5% tryptone. Supernatants were collected and the secreted antibodies were purified from supernatant using the ÄKTAxpress machine and HiTrap Mab Select SuRe columns (cat#11-0034-93) followed by buffer exchange into PBS PH 7.4 using an Amicon® Ultra 15 filter with a 30 kDa MW cutoff (Millipore).

Example 8

Double Reduction and Conjugation

Herceptin VLSpacerX (30 µM in PBS) was reduced by addition of 1.25 mM diethylenetriaminepentaacetate (DTPA) in PBS from a 2.5 mM, pH 6.7 stock solution, followed by addition of cysteamine hydrochloride (final concentration 1 mM) from a 1.0 M stock. The samples were incubated for 120 minutes at 37° C. After cooling to room temperature, cysteamine was removed from the reaction mixture by passage over a Zeba™ spin column (40 KDa MWCO) preconditioned with PBS+1 mM DTPA pH7.3.

After cooling the eluates, maleimide toxin (toxin 1, toxin 3, or toxin 4) was added from a 10 mM DMSO stock solution (generally 5.0 eq. based on the antibody concentration, with an equal amount added to the reduced Herceptin control). The conjugation reaction was allowed to proceed for between 30 and 70 minutes on ice before passage over a Zeba™ spin column (40 KDa MWCO) preconditioned with PBS.

To achieve higher drug loading, the above described reduction and conjugation procedure was repeated using the conjugated material as starting material.

Example 9

Preparation of Light Chain Extension Antibodies for Conjugation by Reduction and Reoxidation Full length, light chain extended monoclonal antibodies were reduced with about a 12 fold of TCEP (tris(2-carboxyethyl)phosphine hydrochloride for 2 hours at 37° C. in PBS and 1 mM DTPA with a final antibody concentration of 2.5 mg/mL. The reduced light chain extension antibody was loaded onto a Zeba™ Spin Desalting Column, 40K MWCO, and eluted with PBS. The eluted reduced antibody was treated with 10 equivalents of 10 mM dehydroascorbic acid (DHAA) in PBS at room temperature, for 30 minutes.

Example 10

Conjugation of Light Chain Extension Antibodies

The reoxidized antibodies from Example 9 were combined with 3.5 molar equivalents relative to the antibody, mixed, and let stand for about an hour at room temperature to effect conjugation and form the light chain extension antibody-drug conjugate (ADC), including Tsp2-Toxin 3, Tsp3-Toxin 3, Tsp4-Toxin 3, Tsp5-Toxin 3, Tsp6-Toxin 3, Tsp9-Toxin 3, Tsp10-Toxin 3, Tsp10-Toxin 4, Tsp10-Toxin 1, Tsp11-Toxin 3, TVLCys1-Toxin 3 (DAR 1.06), Bsp10-Toxin 3, Bsp10-Toxin 4, Bsp10-Toxin 1, Bsp10-Toxin 6, and Bsp10-MC-vc-PABC-MMAE. The conjugation mixture was loaded onto a Zeba™ Spin Desalting Column, 40K MWCO, and eluted with PBS.

Example 11

Antibody Binding Assay

Figure 5:
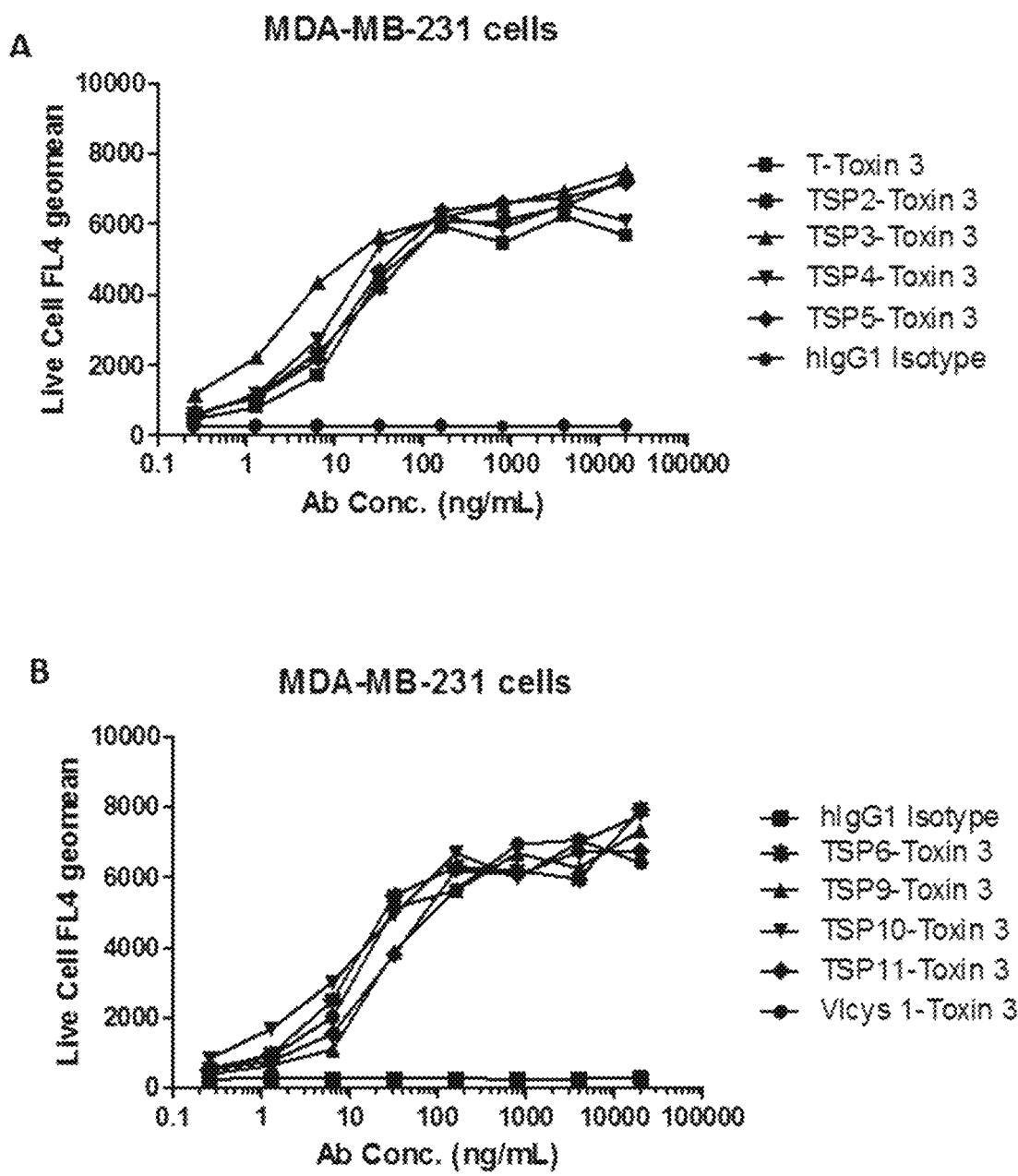
FIG. 5, Panels A and B show antibody binding data for antibody-drug conjugates according to certain embodiments of the present disclosure.

HER2 expressing MDA-MB-231 cells were trypsinized and counted, and 50,000 cells per sample were incubated with unconjugated MAbs or with conjugated ADCs for 24 hours at 4° C. in 50 µl total volume. Antibodies were applied at 20000, 4000, 800, 160, 32, 6.4, 1.28 and 0.256 ng/ml in Leibovitz's L15 media supplemented with 10% Fetal bovine serum. Following incubation the cells were washed twice in ice cold PBS+1% FBS and incubated with Alexa 647 labelled Goat anti-Human IgGFc (2 ug/mL) secondary antibodies+2.5 ug/mL 7-Aminoactinomycin D. The cells were incubated for 30 minutes and washed twice, resuspended in 50 µl PBS+1% FBS and analyzed by flow cytometry. Binding results for unconjugated antibodies are shown in FIG. 4 (Panels A and B), while binding results for ADCs are shown in FIG. 5 (Panels A and B). "TSP2" is an antibody having the light chain polypeptide of SEQ ID NO: 105. "TSP3" is an antibody having the light chain polypeptide of SEQ ID NO: 106. "TSP4" is an antibody having the light chain polypeptide of SEQ ID NO: 107. "TSP5" is an antibody having the light chain polypeptide of SEQ ID NO: 108. "TSP6" is an antibody having the light chain polypeptide of SEQ ID NO: 109. "TSP9" is an antibody having the light chain polypeptide of SEQ ID NO: 112. "TSP10" is an antibody having the light chain polypeptide of SEQ ID NO: 113. "TSP11" is an antibody having the light chain polypeptide of SEQ ID NO: 114. VLcys1 is trastuzumab having the C-terminal light chain extension GGGSC (SEQ ID NO:60).

Example 12

Differential Scanning Calorimetry (DSC)

Figure 6:
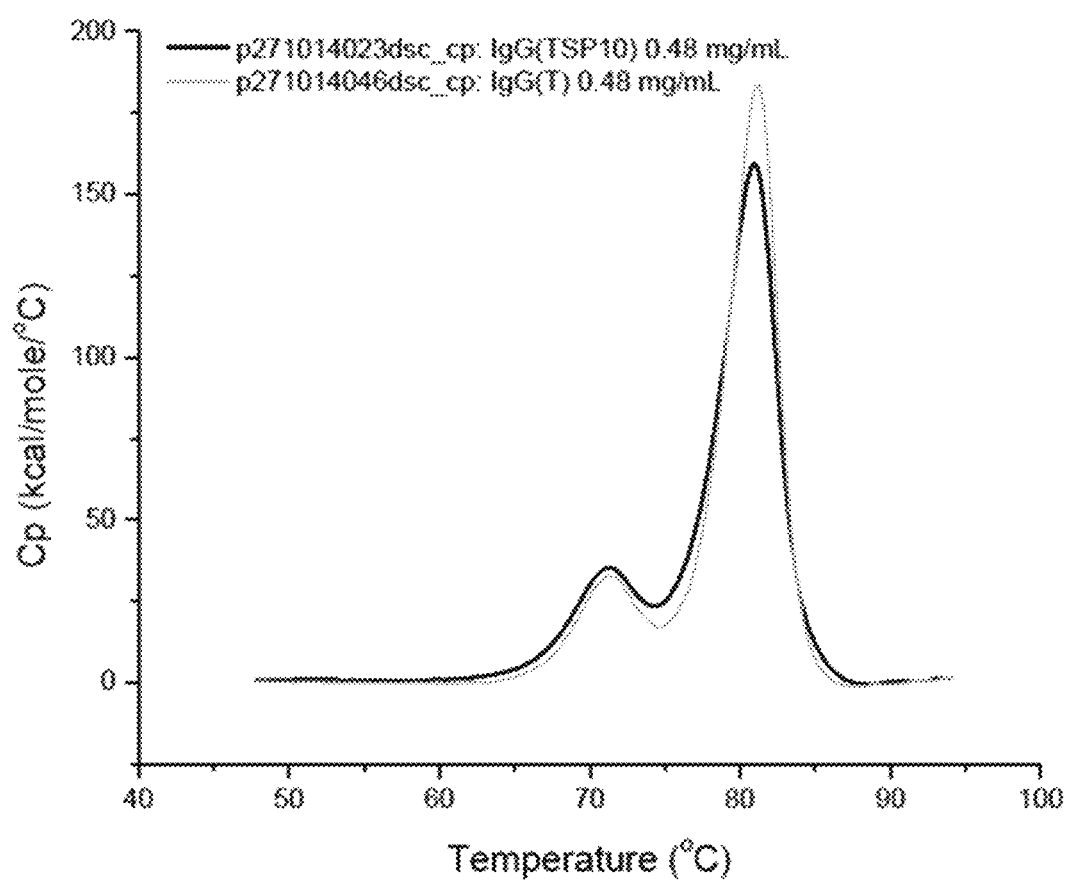
FIG. 6 shows differential scanning calorimetry (DSC) data for an antibody having a C-terminal light chain extension according to one embodiment of the present disclosure.

Differential Scanning calorimetry (DSC) experiment was performed on sample: Trastsuzumab with extension (TSP10) and Trastuzumab (T) in PBS pH 7.4. Before loading the samples in the DSC cell, sample was equilibrated at room temperature, diluted with buffer, and degassed under vacuum with stirring for 8 minutes. The samples were scanned from 10 to 100° C. at a scan rate of 60° C./hr using a VPCapillary-DSC, MicroCal. The reference cell contained PBS buffer. Results are shown in FIG. 6.

Example 13

Figure 7:
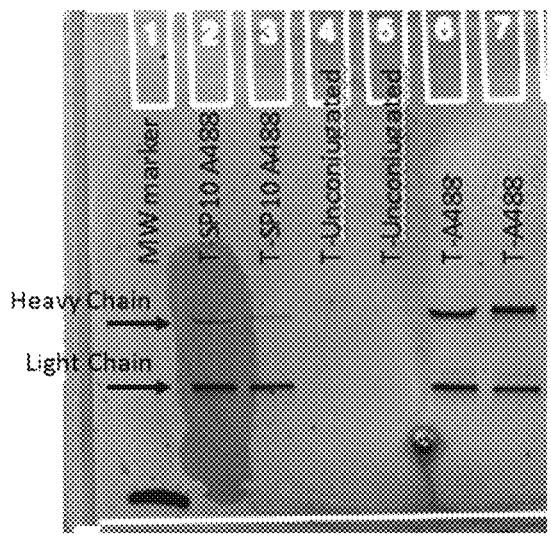
FIG. 7 is a gel image showing Alexa488 conjugation to an antibody according to an embodiment of the present disclosure.

Alexa488 Conjugation 5-maleimido-Alexa488 was conjugated to MAbs using the reduction/conjugation methods described above. The antibodies were analyzed by SDS PAGE using the samples at a dilution between 1:15 to 1:40 from 100 µg/ml in PBS and loading 20 µl in each lane. The gels were imaged using a Typhoon Trio™ imager (GE Healthcare Life Sciences) measuring the fluorescence of Alexa488. Results are shown in FIG. 7.

Example 14

In Vivo Study Protocol 7-8 week old Female NOD/SCID gamma (NSG) mice (Jackson) was inoculated with 5*106 NCI-N87 tumor cells (ATCC Cat # CRL-5822) mixed 1:1 with matrigel in a total volume of 100 µl. Tumors were measured every Monday, Wednesday, and Friday. Once tumors reached 150-200 mm$^3$ in size, animals were assigned to treatment groups as shown in Table 6 below to counterbalance the average tumor size across groups. "T" is an abbreviation for trastuzumab.

TABLE 6

In vivo study groups

| Group # | Group Name | Dose (mg/kg) | DAR |
|---|---|---|---|
| 1 | Vehicle | N/A | N/A |
| 2 | TSP6-Toxin 3 | 12 | 1.8 |
| 3 | TSP4-Toxin 3 | 12 | 2.06 |
| 4 | TSP10-Toxin 4 | 12 | 1.66 |
| 5 | TSP10-Toxin 1 | 12 | 2.04 |
| 6 | TSP10-Toxin 3 | 12 | 2.12 |
| 7 | TSP10 | 12 | N/A |

Figure 8:
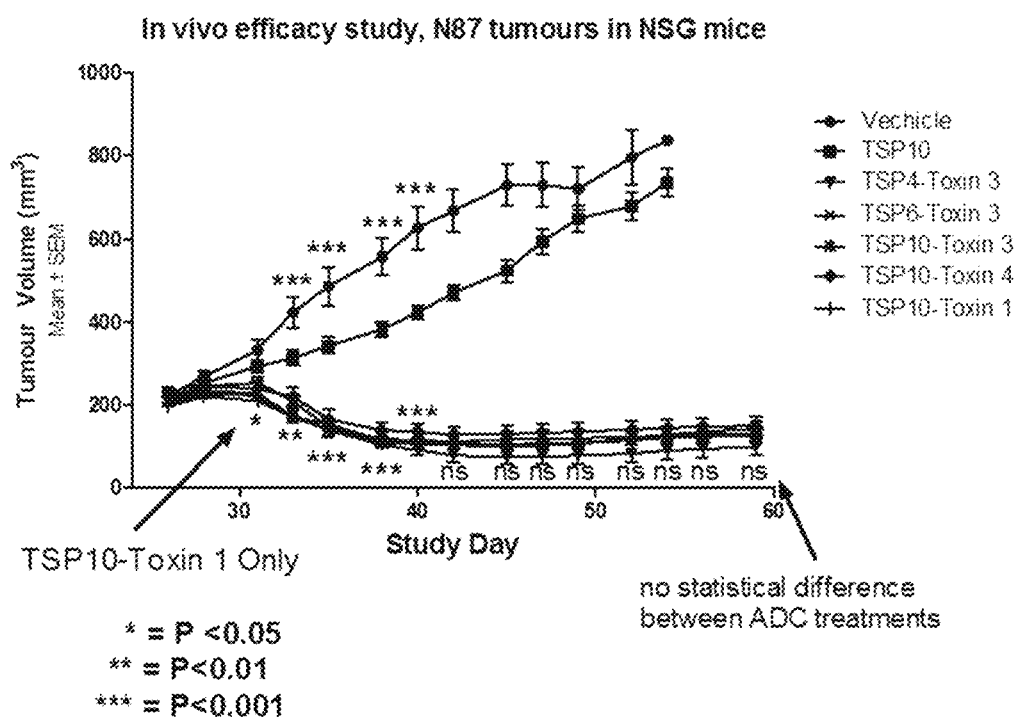
FIG. 8 shows in vivo tumor volume change over time in mice administered antibodies or antibody conjugates according to certain aspects of the present disclosure.

Animals were treated with their respective test articles with a single intravenous injection at the concentrations indicated in Table 6, and tumor measurement continued every Monday, Wednesday, and Friday for up to 60 days or until the tumor size reached 800 mm$^3$. All animals received doses as indicated in an Injection Record. Post Injection Clinical Observation Record (PICOR) forms were used to monitor acute toxicity post injection. No significant body weight loss was observed in any groups and no acute toxicity responses post injection were noted in PICOR files. Results of the in vivo study are shown in FIG. 8.

Example 15

Analysis of Antibody-Drug Conjugates by Hydrophobic Interaction Chromatography (HIC)

HIC analysis of antibody drug conjugates were performed on a HP 1100 Series HPLC with a DAD at 280 nm using a TSKgel Butyl-NPR column (2.5 uM, 4.6 mm×3.5 cm). The method was run at 1 mL/min from a linear gradient of 95% to 5% mobile phase A over 12 minutes with re-equilibration back to 95% A for 3 minutes (A: 1.5M ammonium sulphate and 25 mM sodium phosphate monobasic at pH 4.4; B: 25% IPA in 25 mM sodium phosphate at pH 4.73). Chemstation software was used for data collection, analysis and peak area quantification. Results are shown in FIGS. 20-41.

Example 16

Analysis of Antibodies and Antibody-Drug Conjugates by Native Size Exclusion Chromatography Non-denaturing SEC analysis of recombinant antibodies and antibody drug conjugates were carried out on a HP1100 Series HPLC with DAD at 280 nm using an Acquity UPLC BEH 200 SEC column (1.7 uM, 4.6 mm×150 cm). The analysis was performed using an isocratic elution over 20 minutes at 0.2 mL/min with 25 mM sodium phosphate and 150 mM sodium chloride buffer at pH 6.8. Chemstation software was used for data collection, analysis and peak area quantification.

Individual aliquots of 1 mg/mL solutions of TSp10, TSp10-Toxin 3, TSp10-Toxin 1, TSp10-Toxin 4, TSp6-Toxin 3, TSp4-Toxin 3 in PBS, pH 7, were prepared. Non-denaturing SEC-UV analysis (described previously) was performed at an injection volume of 10 µL at time zero prior to incubation at 37° C. Aliquots of each sample were analyzed by non-denaturing SEC-UV after 191 hours of incubation, and after 330 hours of incubation. Percent monomer peak area of each species was adjusted against their respective zero time point measurement.

For trastuzumab control, 99.36% of the protein sample was in the monomeric state, while one different aggregate species was present at 0.63%. For T-VLCys1, 98.39% of the protein sample was in the monomeric state, while other aggregate species were present at 1.16%, 0.266% and 0.175%. For T-SP2, 96.5% of the protein sample was in the monomeric state, while two different aggregate species were present at 0.3%, 1.5% and 1.8%. For T-SP3, 98.5% of the protein sample was in the monomeric state, while two different aggregate species were present at 1.17% and 0.35%. For T-SP4, 98% of the protein sample was in the monomeric state, while other different aggregate species were present at 1.4%, 0.39% and 0.22%. For T-SP5, 94% of the protein sample was in the monomeric state, while two different aggregate species were present at 2.1% and 3.2%. For T-SP6, 89% of the protein sample was in the monomeric state, while other different aggregate species were present at 1.5% and 8.8%. For T-SP7, 95.95% of the protein sample was in the monomeric state, while other different aggregate species were present at 3%, 0.51% and 0.50%. For T-SP9, 94.5% of the protein sample was in the monomeric state, while other different aggregate species were present at 0.6%, 3.8% and 1%. For T-SP10, 97.3% of the protein sample was in the monomeric state, while other different aggregate species were present at 2.2%, 0.27% and 0.22%. For T-SP-11, 77.7% of the protein sample was in the monomeric state, while other different aggregate species were present at 6.3%, 8.6%, 2.7% and 4.5%. For T-SP12, 87.5% of the protein sample was in the monomeric state, while other different aggregate species were present at 2.2%, 1.6%, 8.6% and 4.5%.

Example 17

Analysis of Antibodies and Antibody-Drug Conjugates by Size Exclusion Chromatography-Intact Mass Denaturing SEC-high resolution mass spectrometry (HRMS) for intact mass analysis of recombinant antibodies and antibody drug conjugates was performed on a Waters Acquity H Class UPLC with PDA detection at 280 nm utilizing an Acquity UPLC BEH 200 SEC column (1.7 uM, 4.6 mm×150 cm). High resolution mass spectrometry detection was achieved using a MicroMass Q-TOF Premier with a scan range from 250-4900 m/z. The analysis was performed using an isocratic elution at 0.25 ml/min over 11 minutes with 70/30 H20/ACN with 0.1% TFA and 0.1% FA. Data collection and analysis was done with MassLynx 4.1 with spectra deconvolved with MaxEnt1.

Figure 9A:
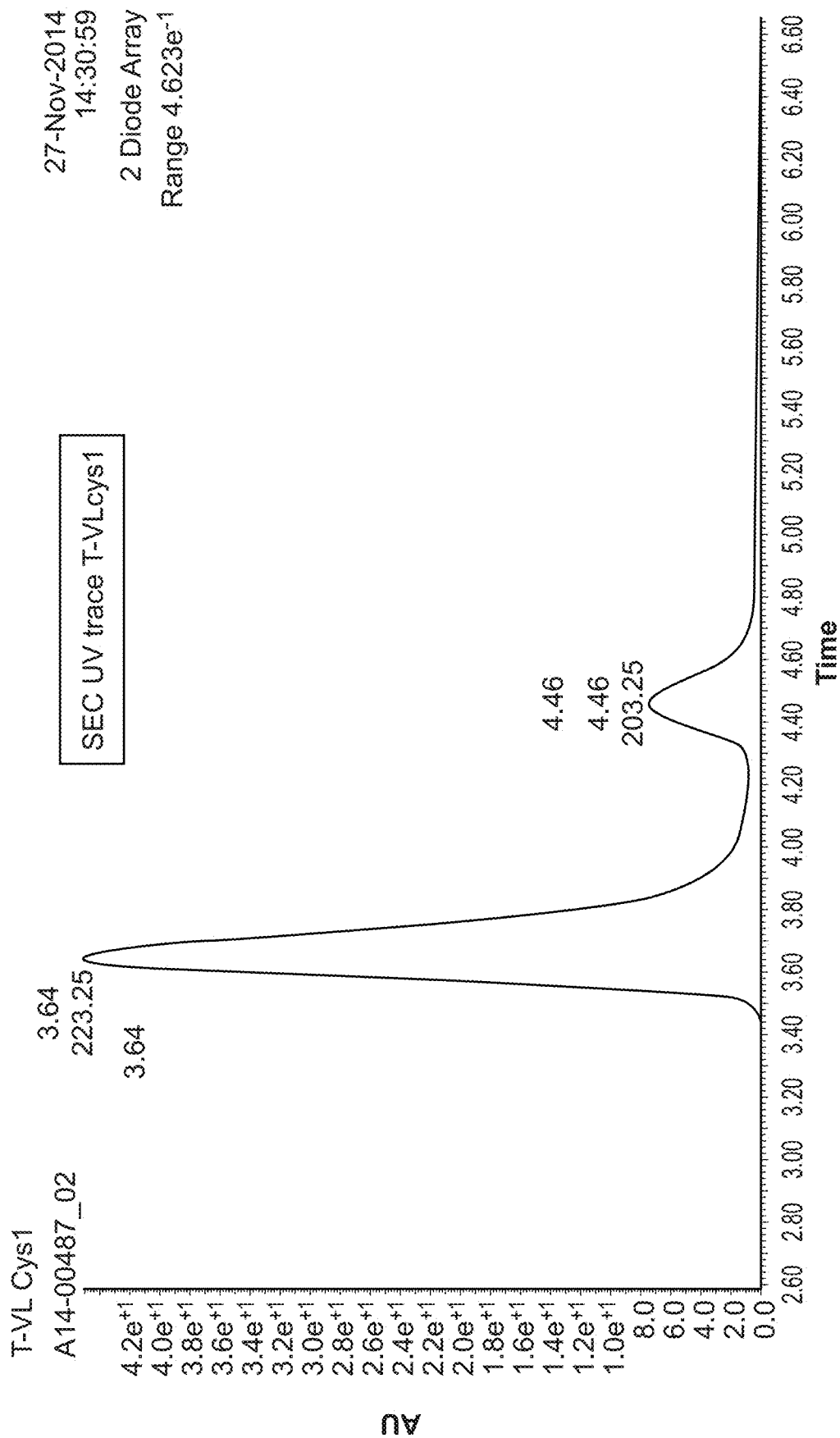
FIG. 9, Panels A-C provide size exclusion chromatography-mass spectrometry (SEC-MS) data for an antibody (T-VLcys1) having a C-terminal light chain extension according to an embodiment of the present disclosure.
Figures 9B, 9C:
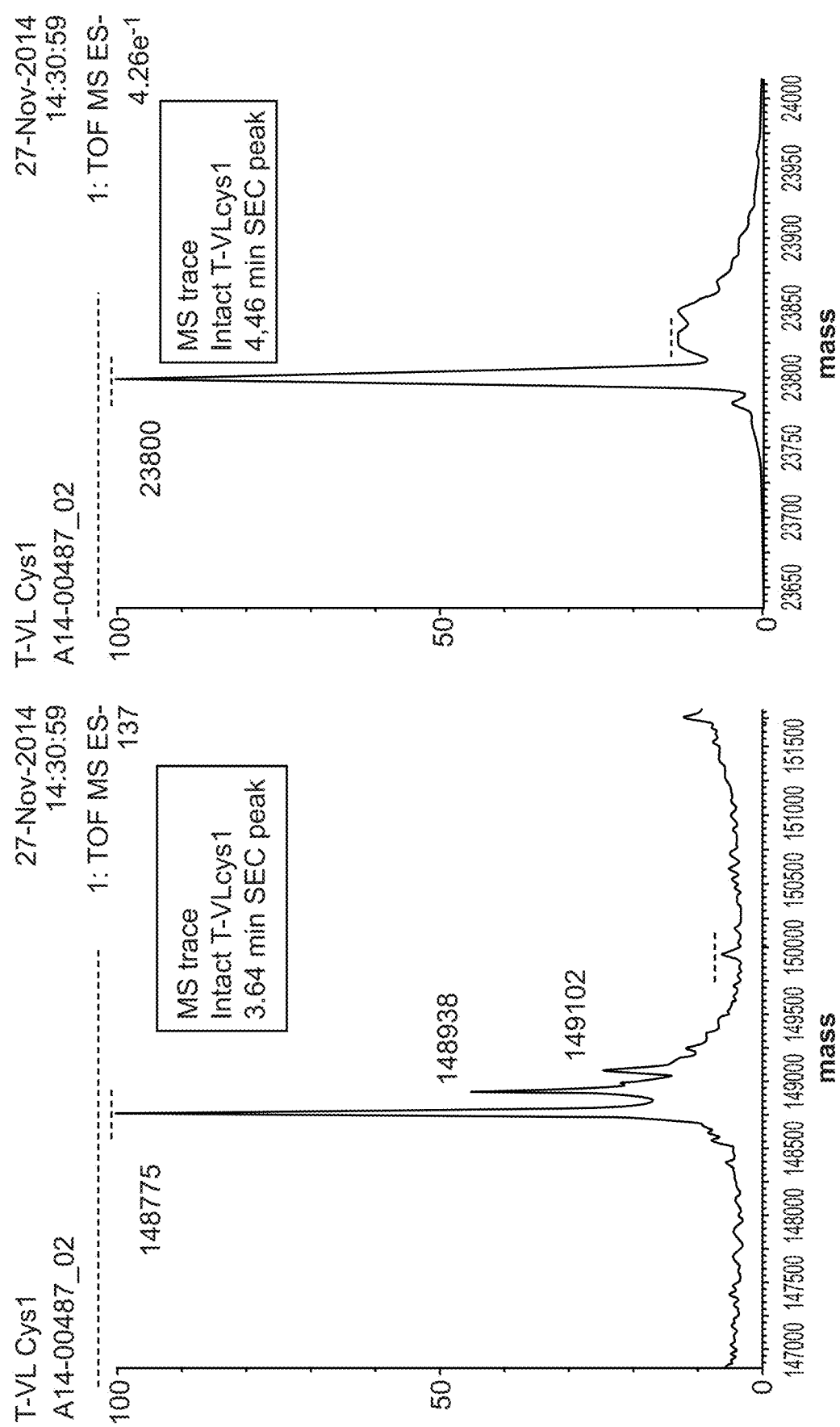
Figure 10A:
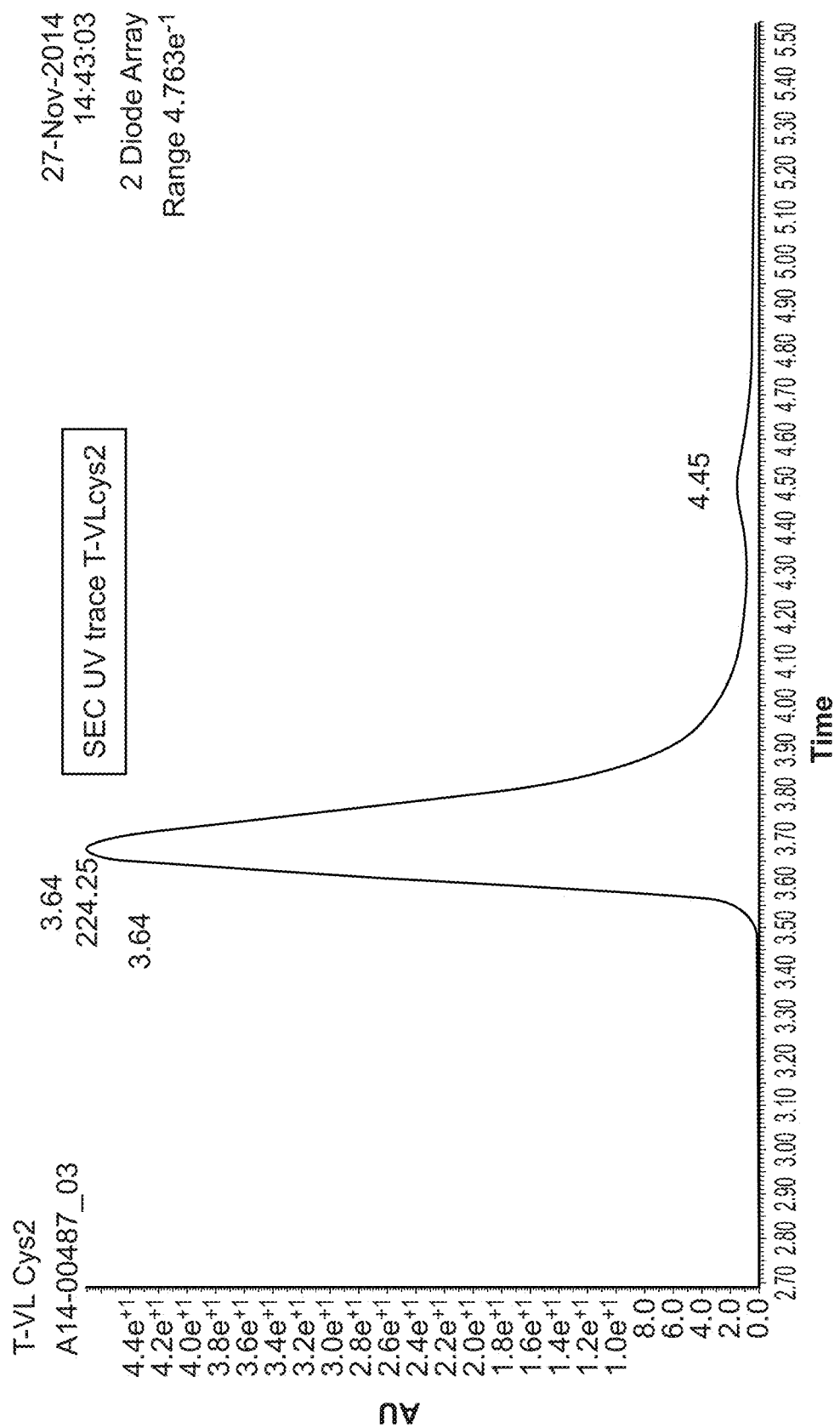
FIG. 10, Panels A-C provide SEC-MS data for an antibody (T-VLcys2) having a C-terminal light chain extension according to an embodiment of the present disclosure.
Figures 10B, 10C:
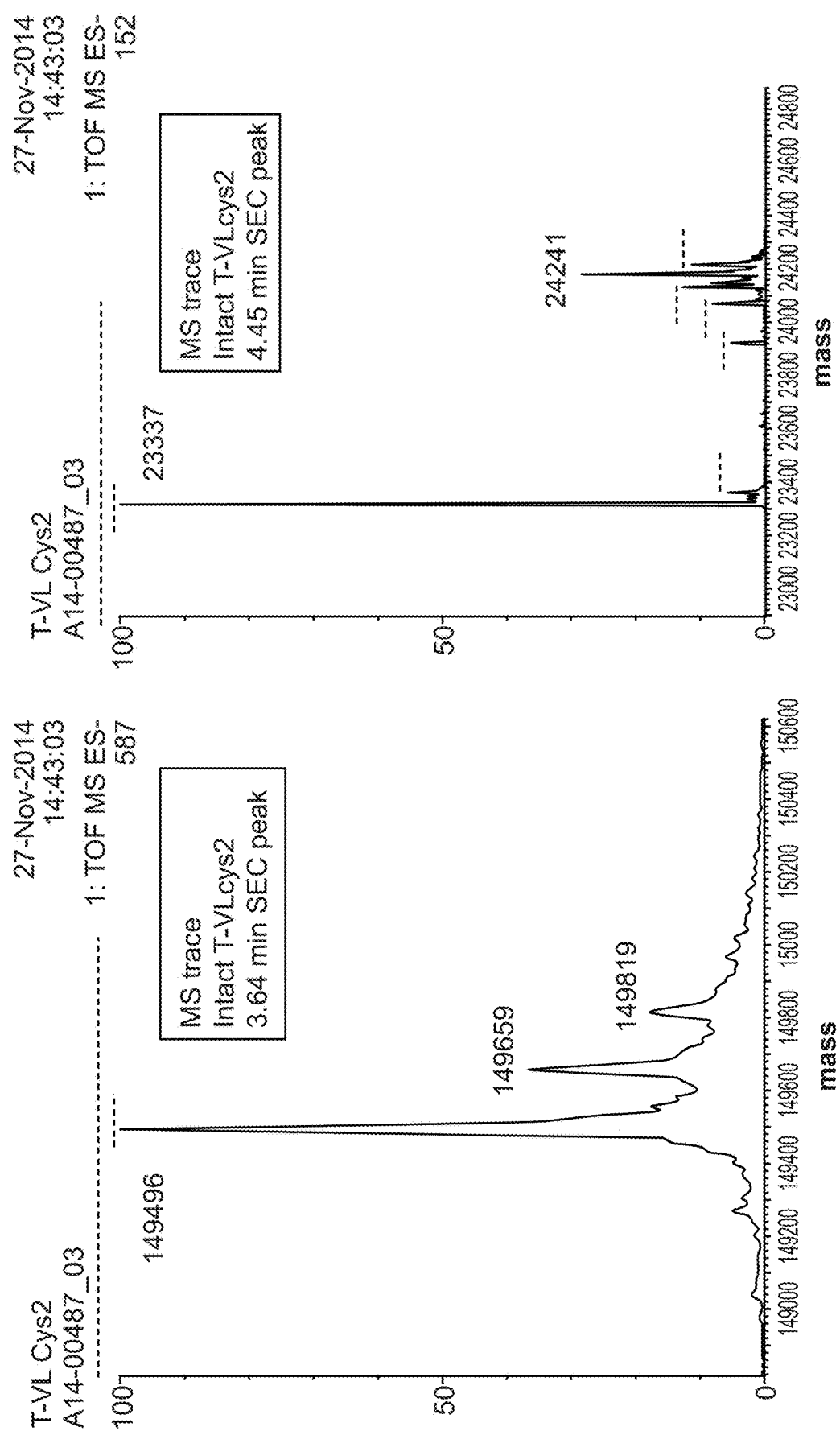
Figure 11A:
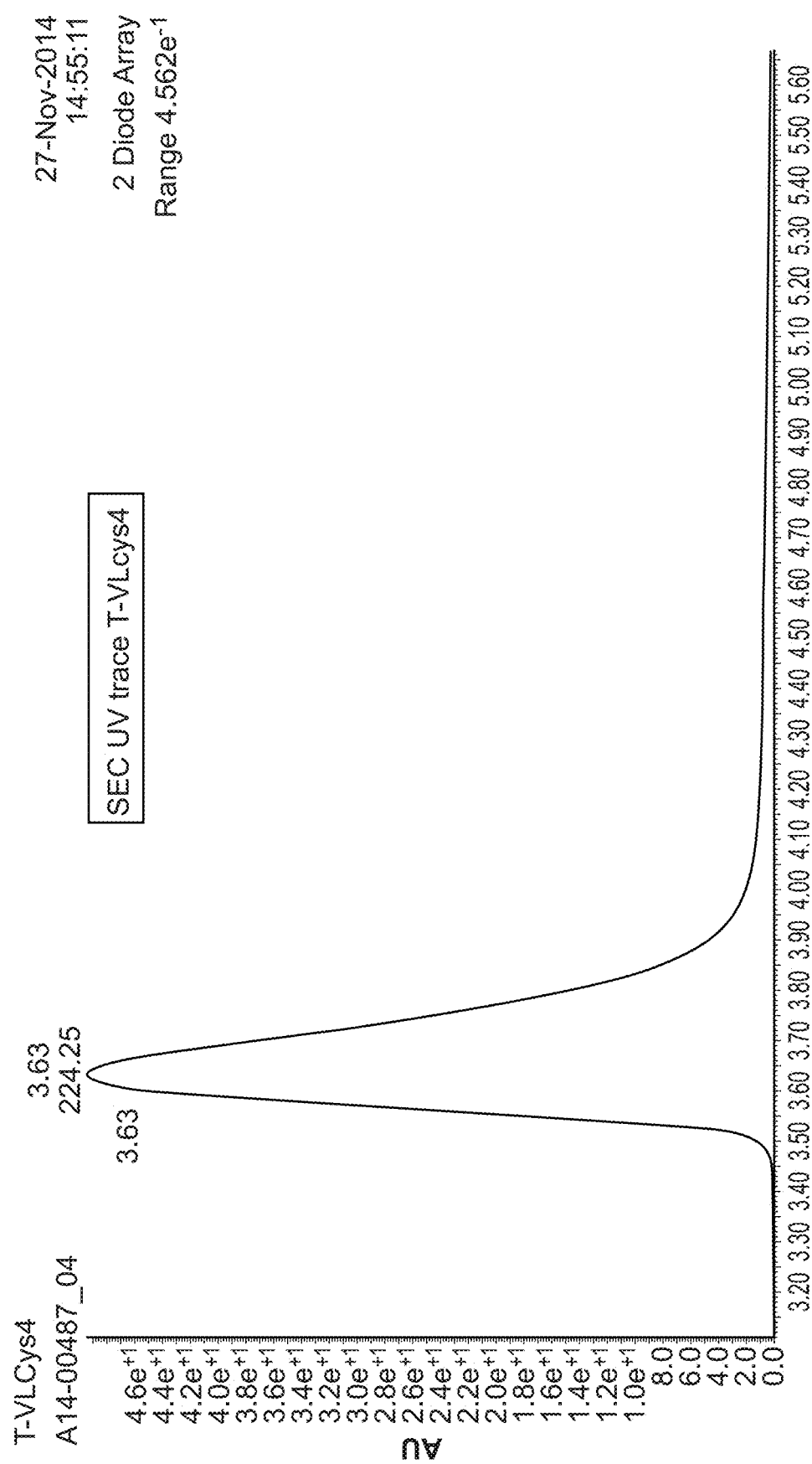
FIG. 11, Panels A and B provide SEC-MS data for an antibody (T-VLcys4) having a C-terminal light chain extension according to an embodiment of the present disclosure.
Figure 11B:
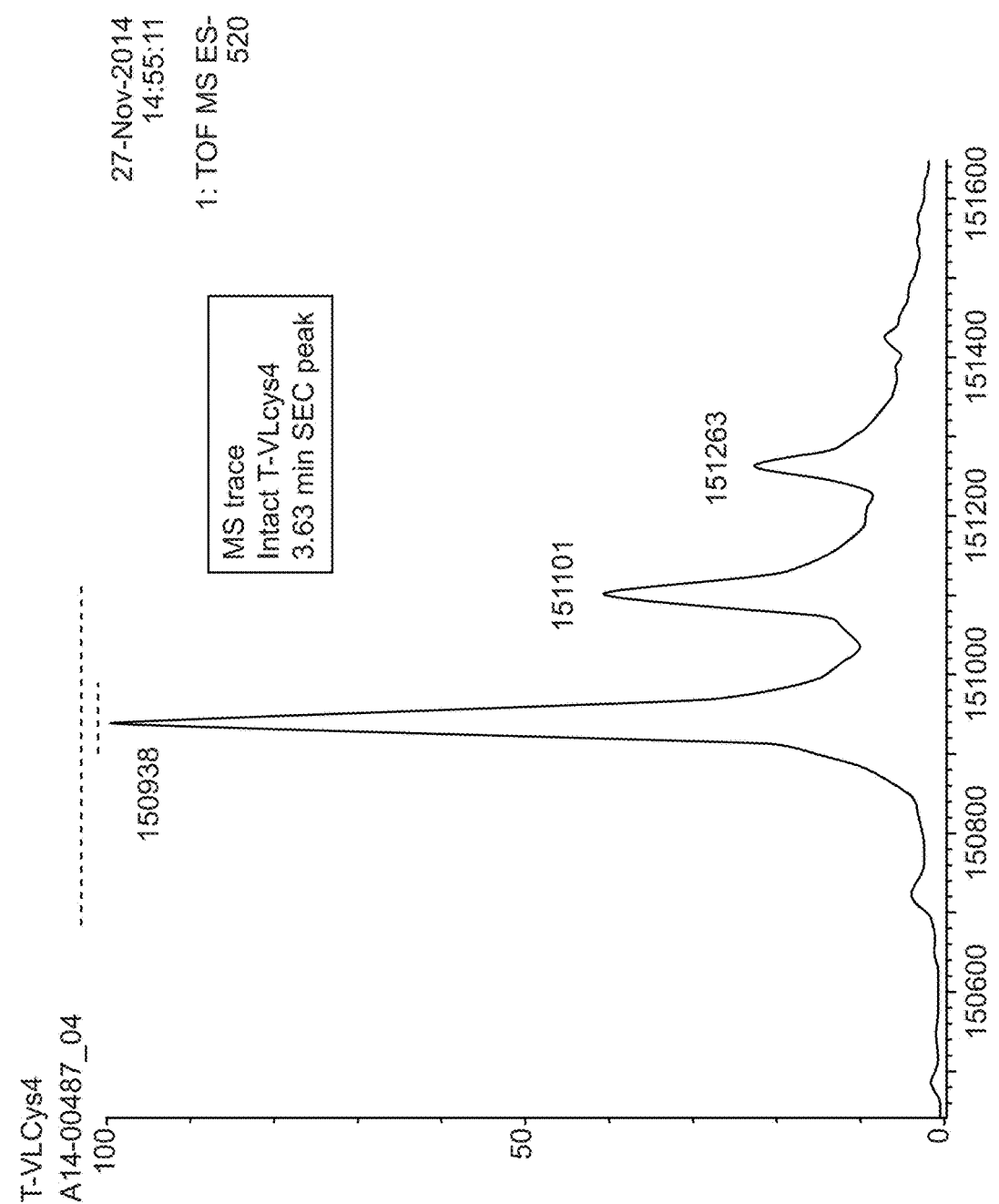
Figure 12A:
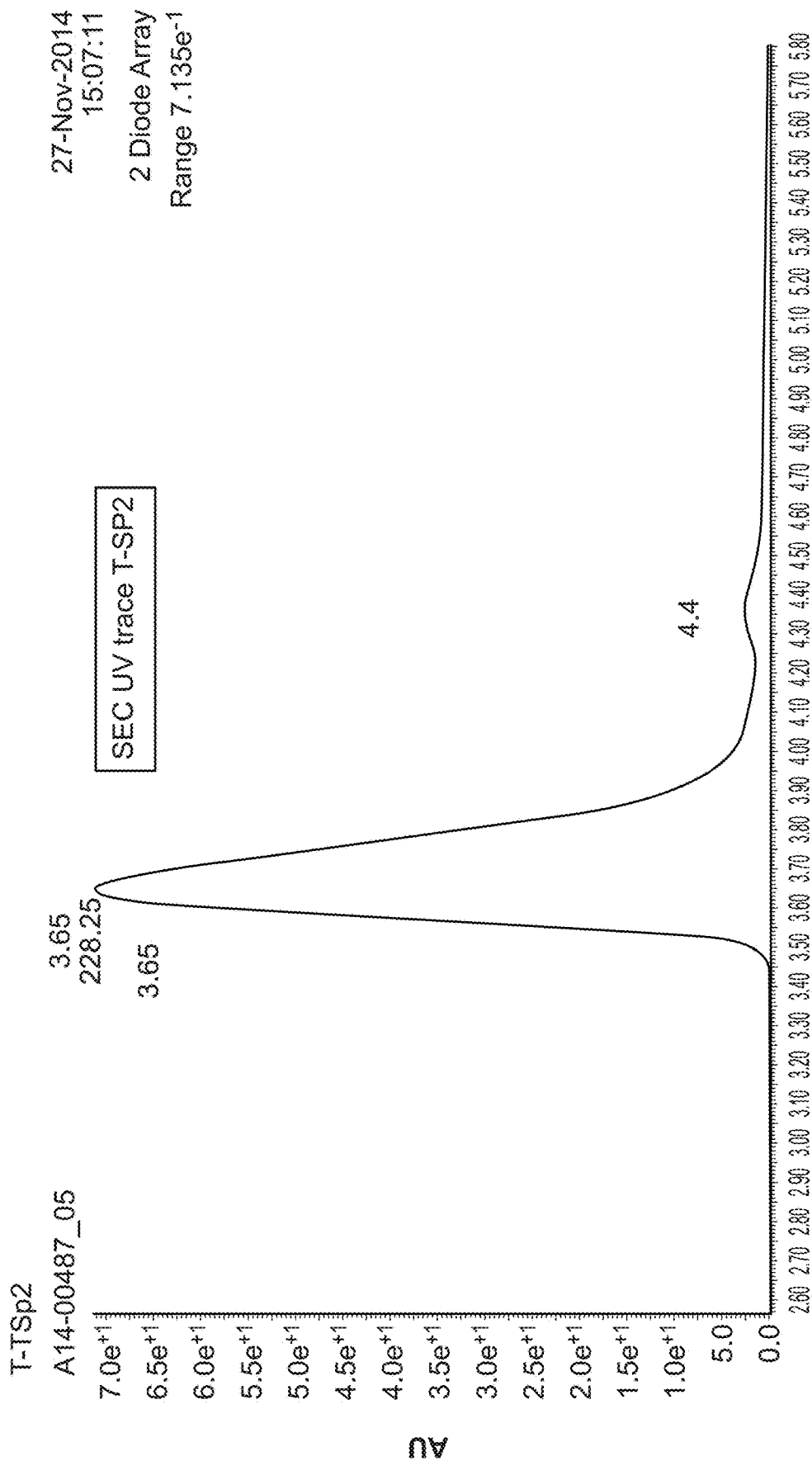
FIG. 12, Panels A and B provide SEC-MS data for an antibody (T-SP2) having a C-terminal light chain extension according to an embodiment of the present disclosure.
Figure 12B:
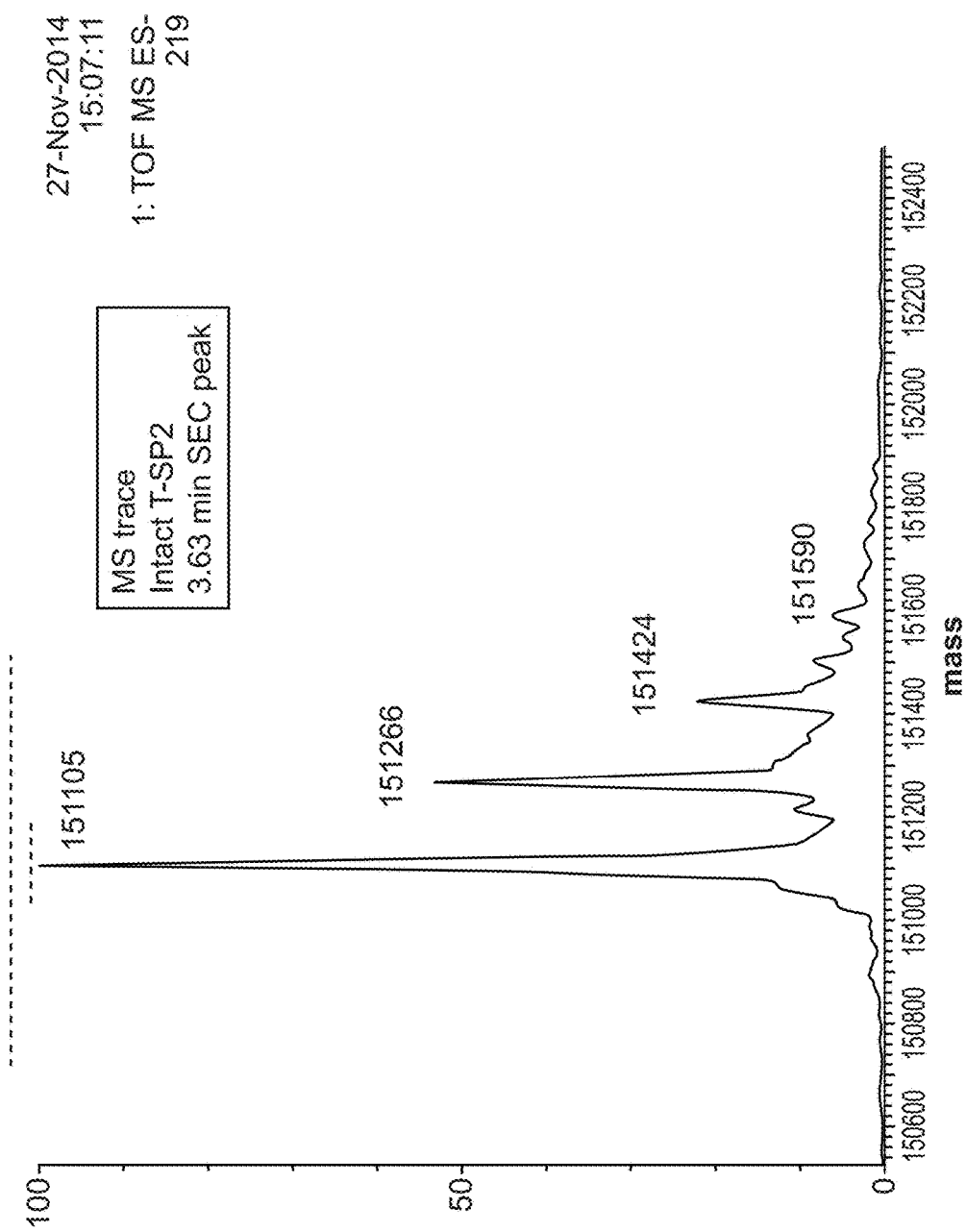
Figure 13A:
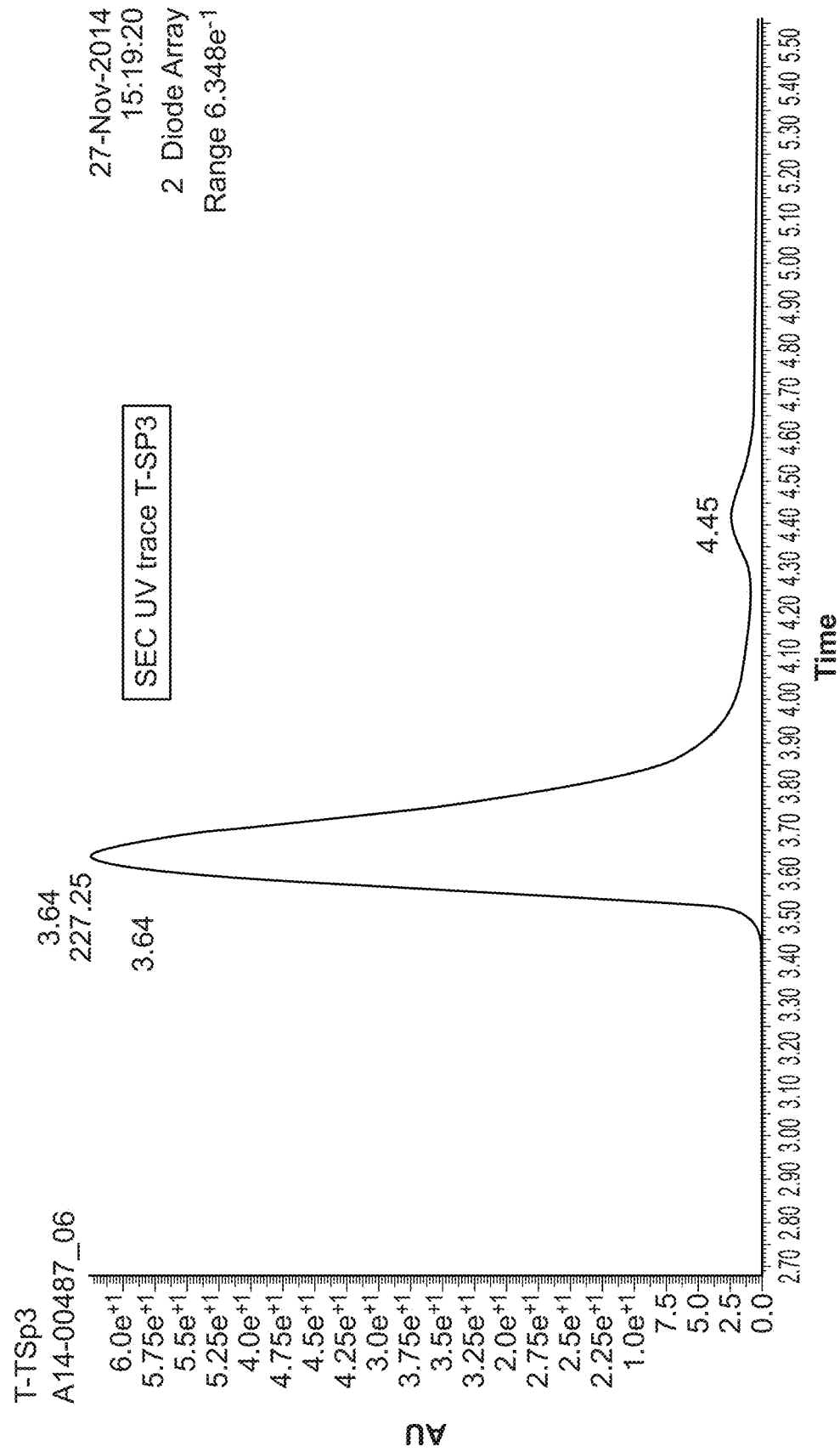
FIG. 13, Panels A-C provide SEC-MS data for an antibody (T-SP3) having a C-terminal light chain extension according to an embodiment of the present disclosure.
Figures 13B, 13C:
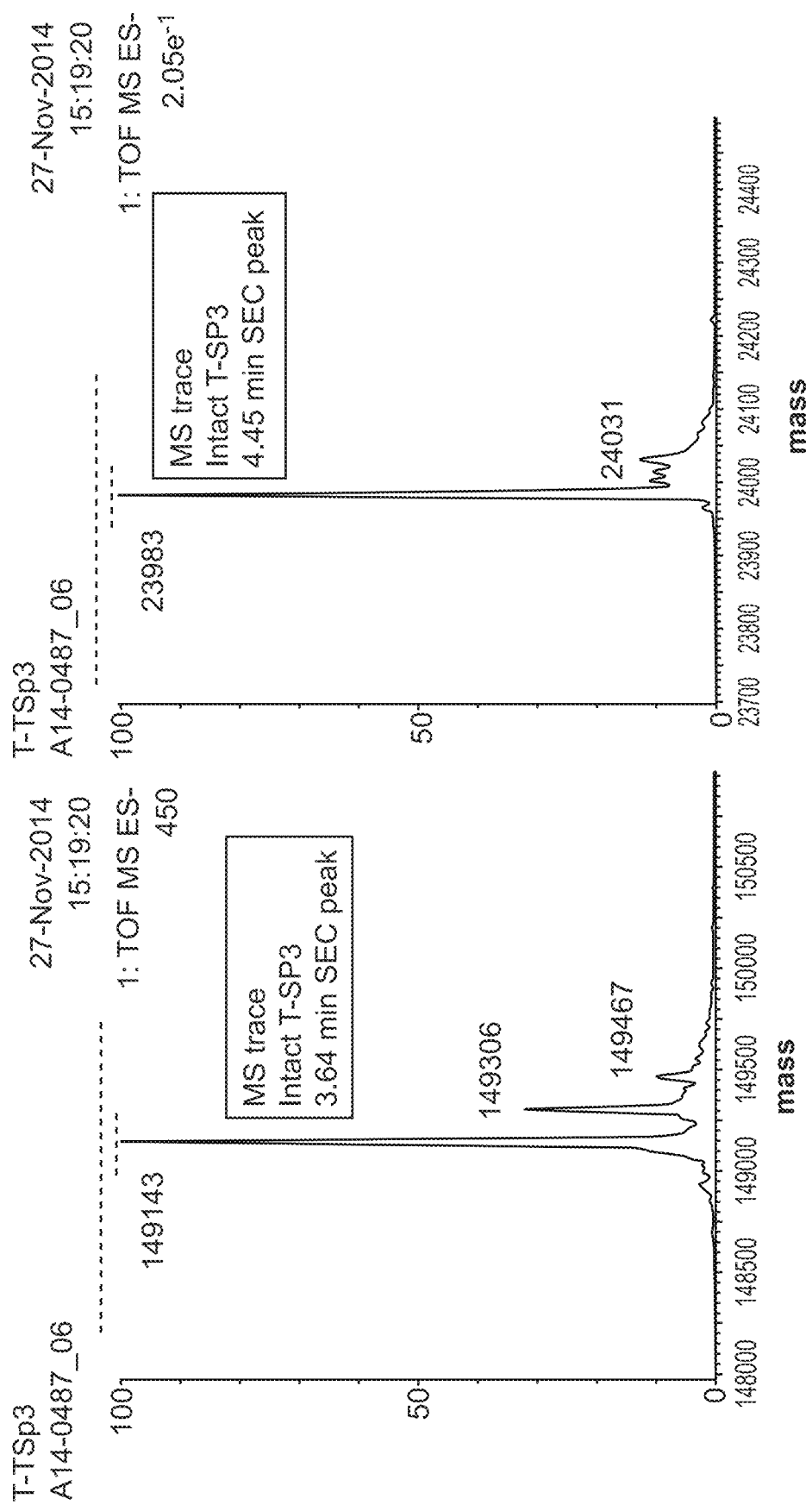
Figure 14A:
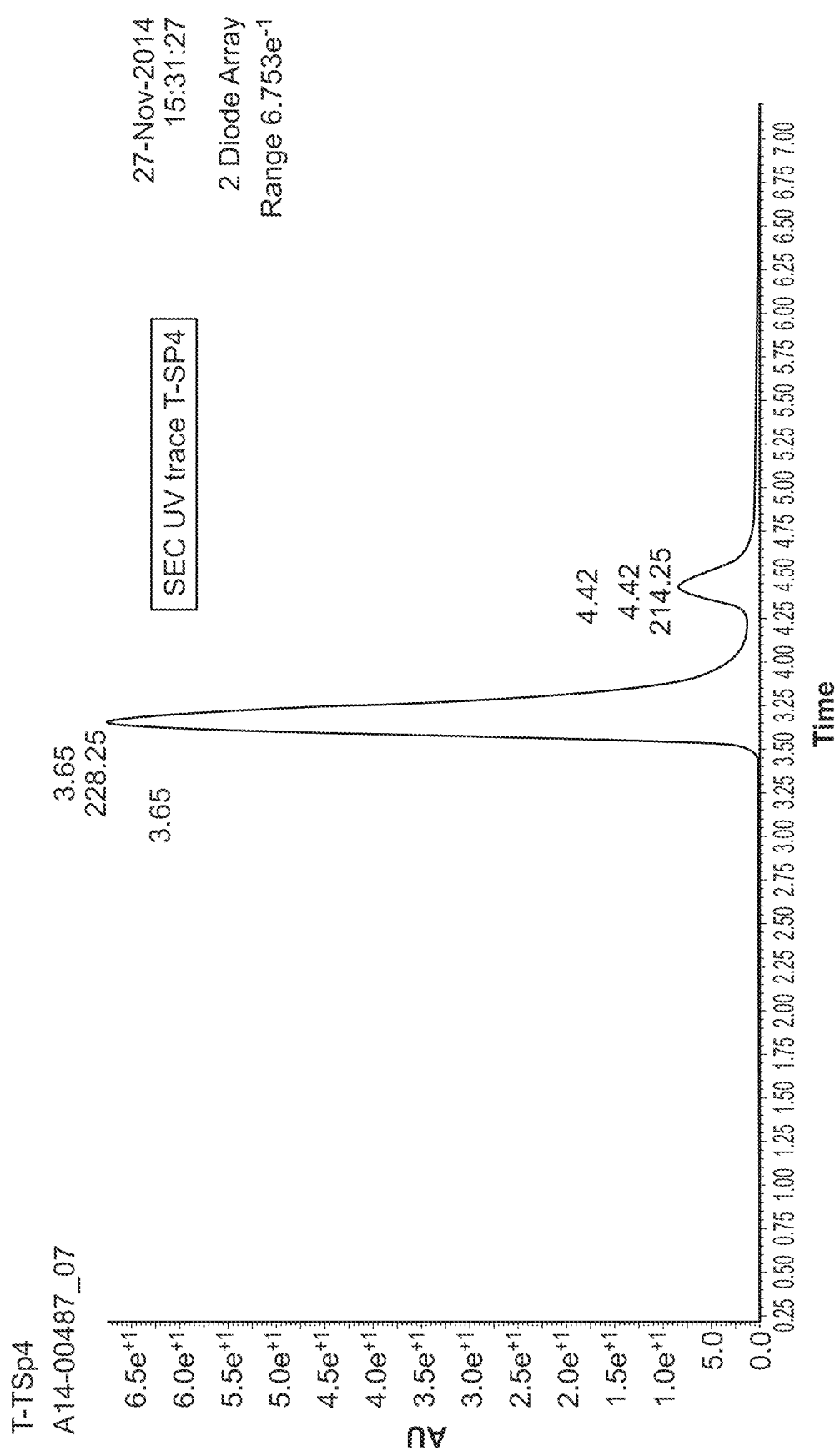
FIG. 14, Panels A-C provide SEC-MS data for an antibody (T-SP4) having a C-terminal light chain extension according to an embodiment of the present disclosure.
Figures 14B, 14C:
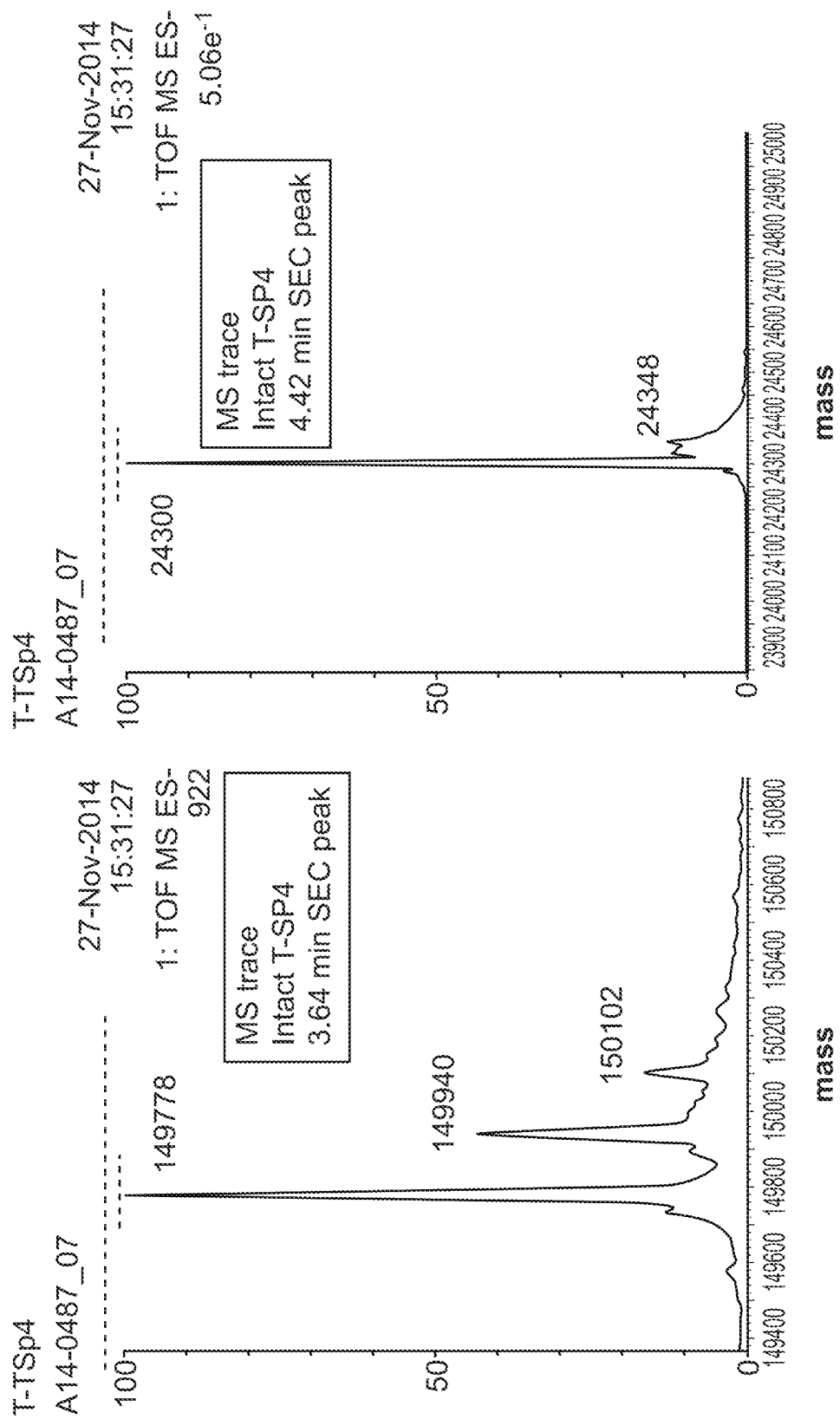
Figure 15A:
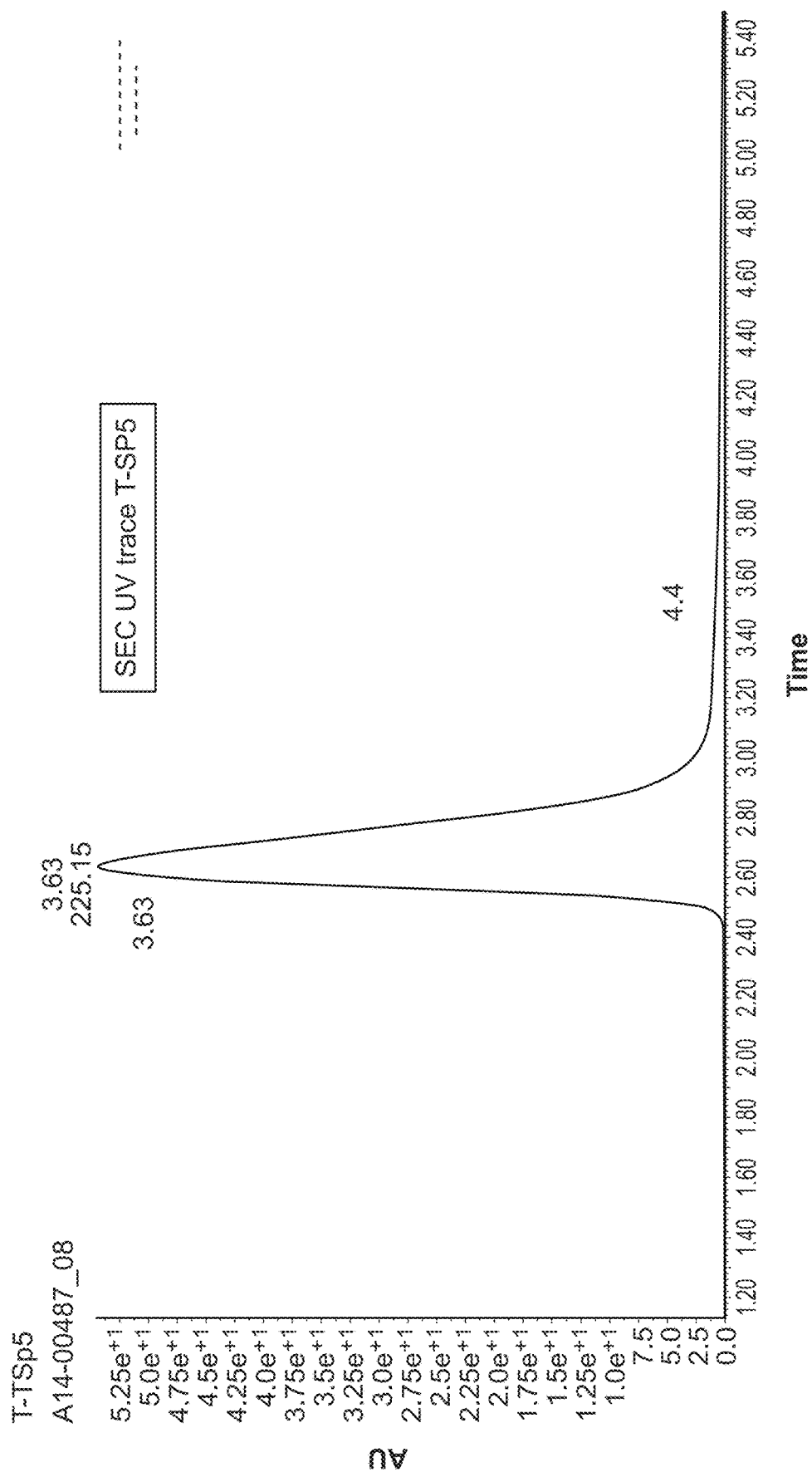
FIG. 15, Panels A and B provide SEC-MS data for an antibody (T-SP5) having a C-terminal light chain extension according to an embodiment of the present disclosure.
Figure 15B:
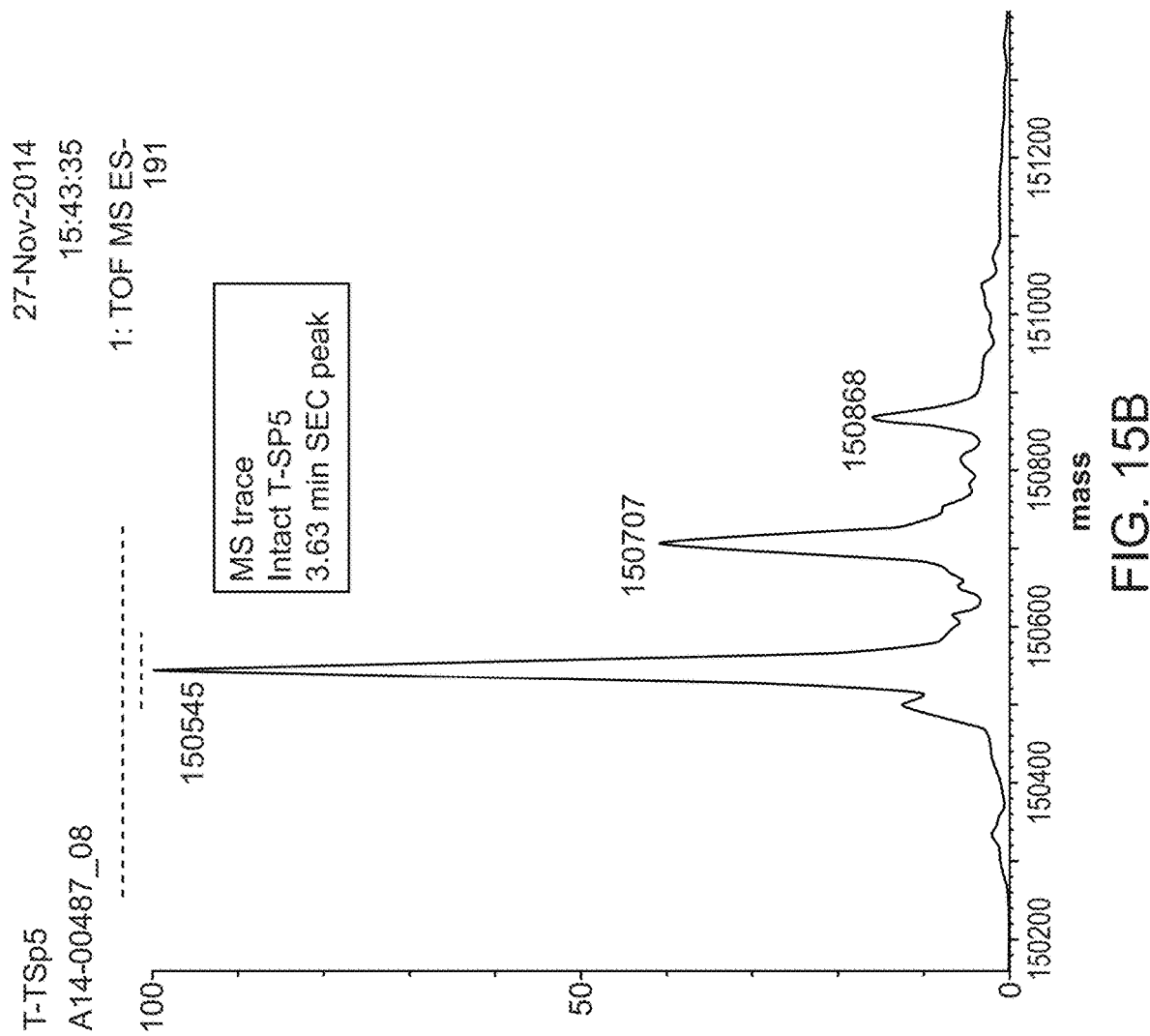
Figure 16A:
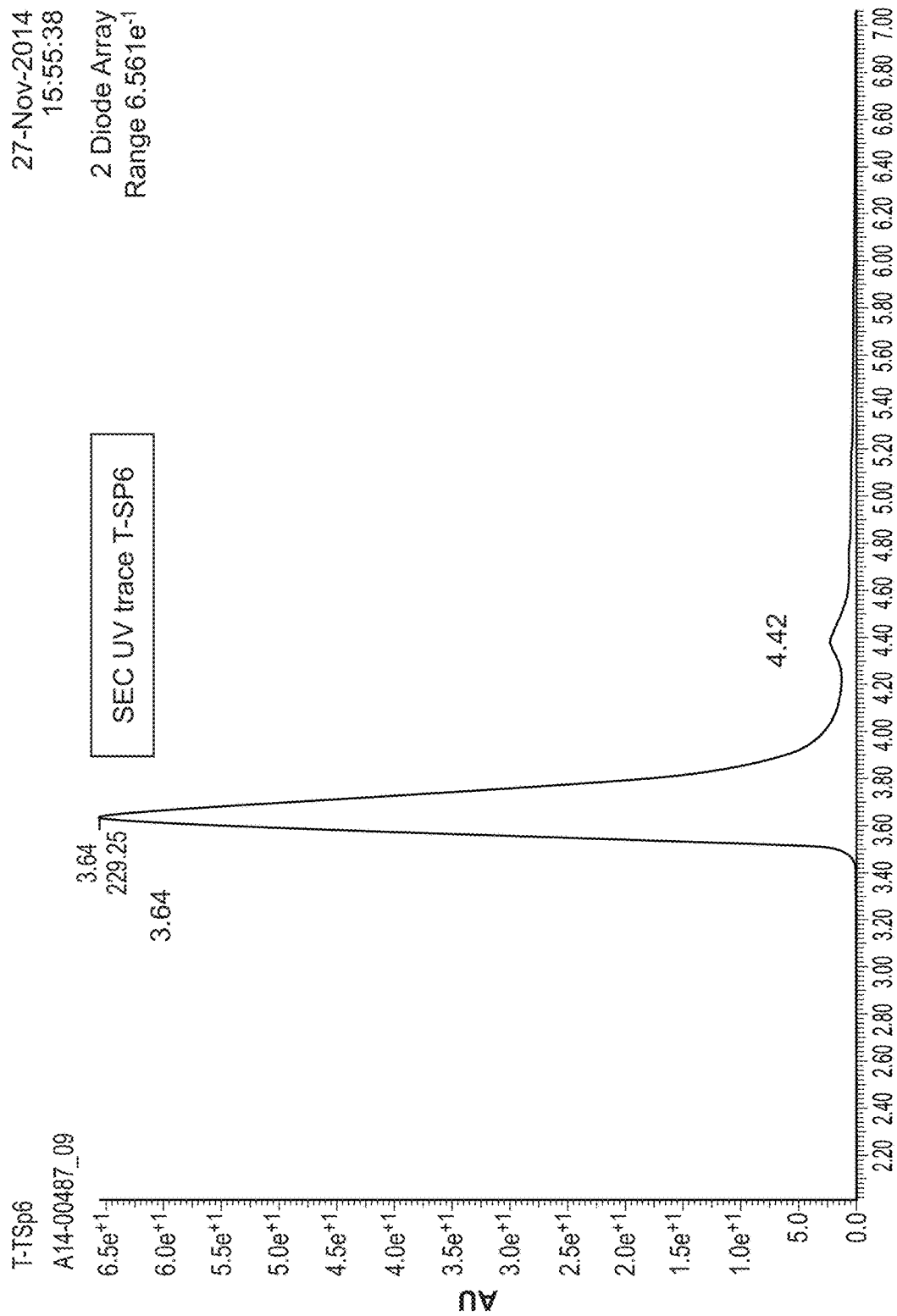
FIG. 16, Panels A-C provide SEC-MS data for an antibody (T-SP6) having a C-terminal light chain extension according to an embodiment of the present disclosure.
Figures 16B, 16C:
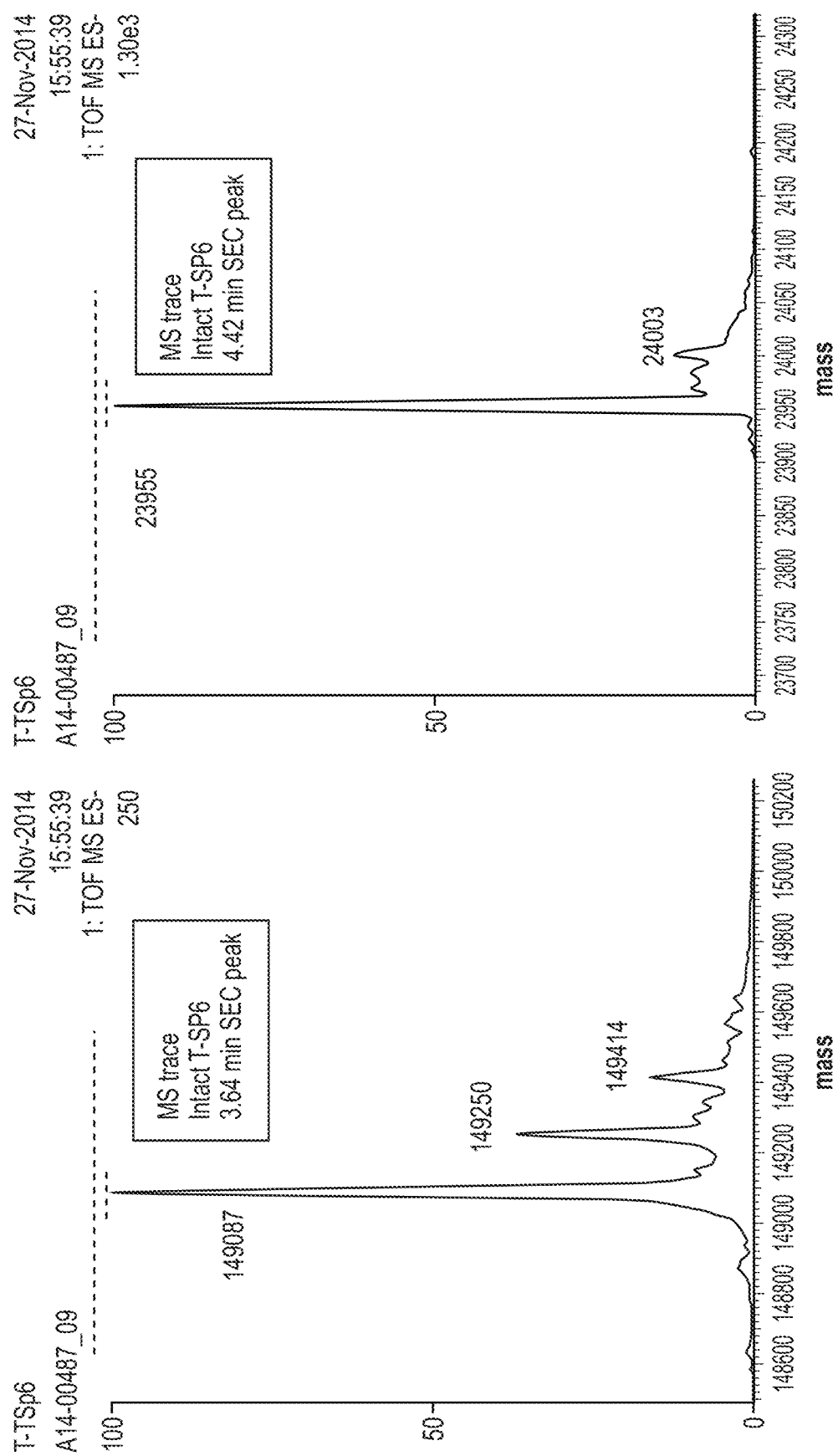
Figure 17A:
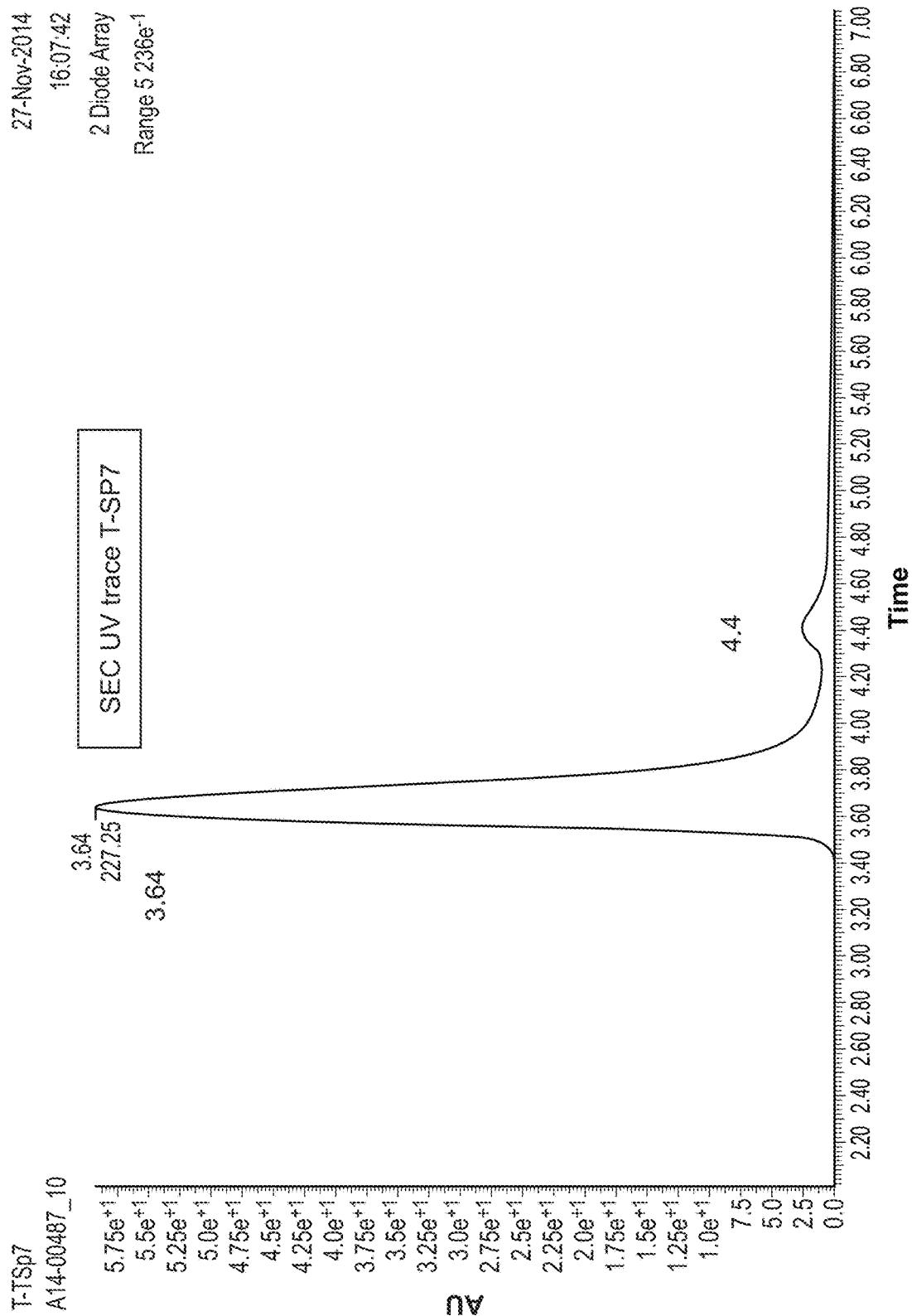
FIG. 17, Panels A-C provide SEC-MS data for an antibody (T-SP7) having a C-terminal light chain extension according to an embodiment of the present disclosure.
Figures 17B, 17C:
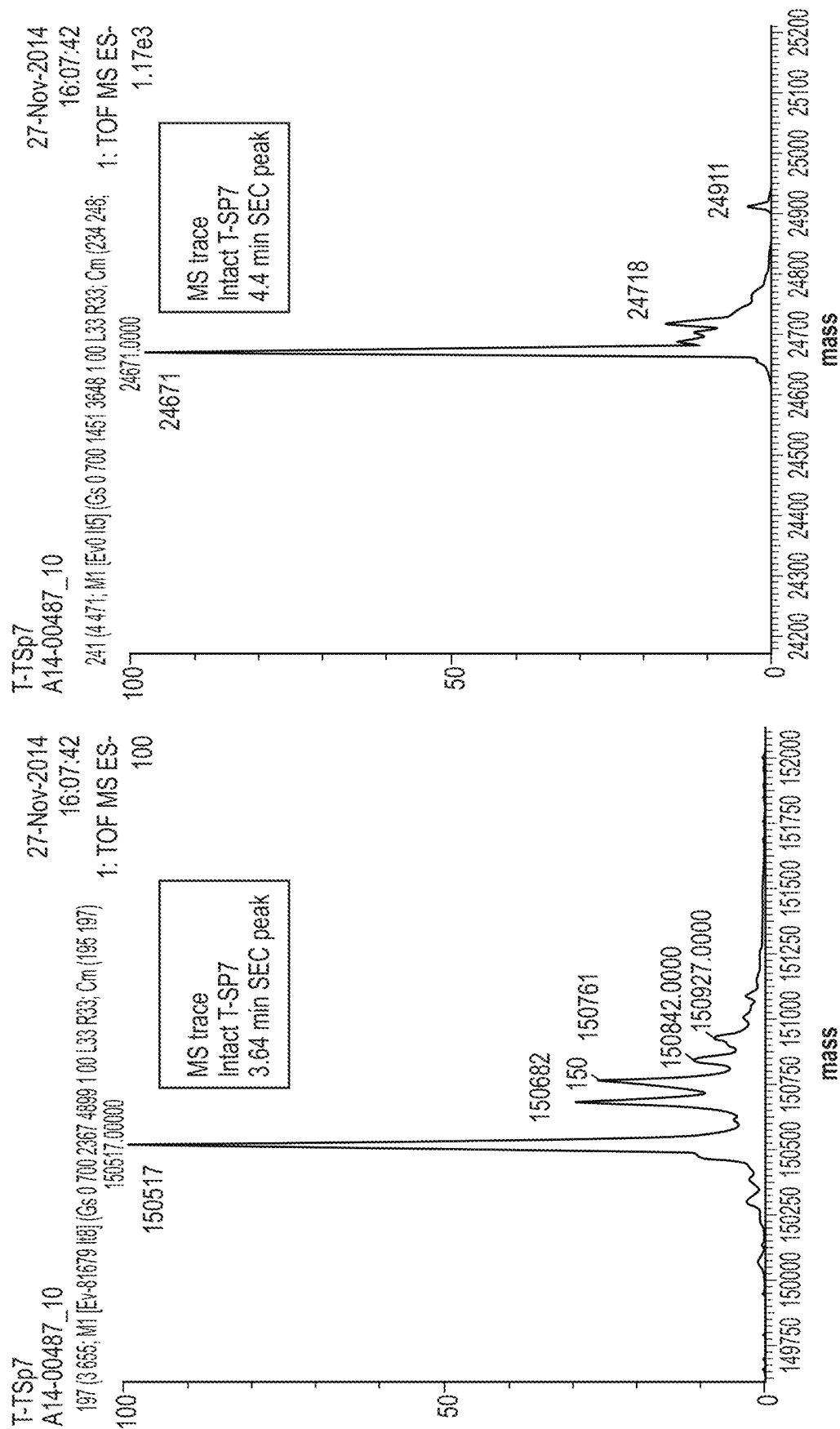
Figure 18A:
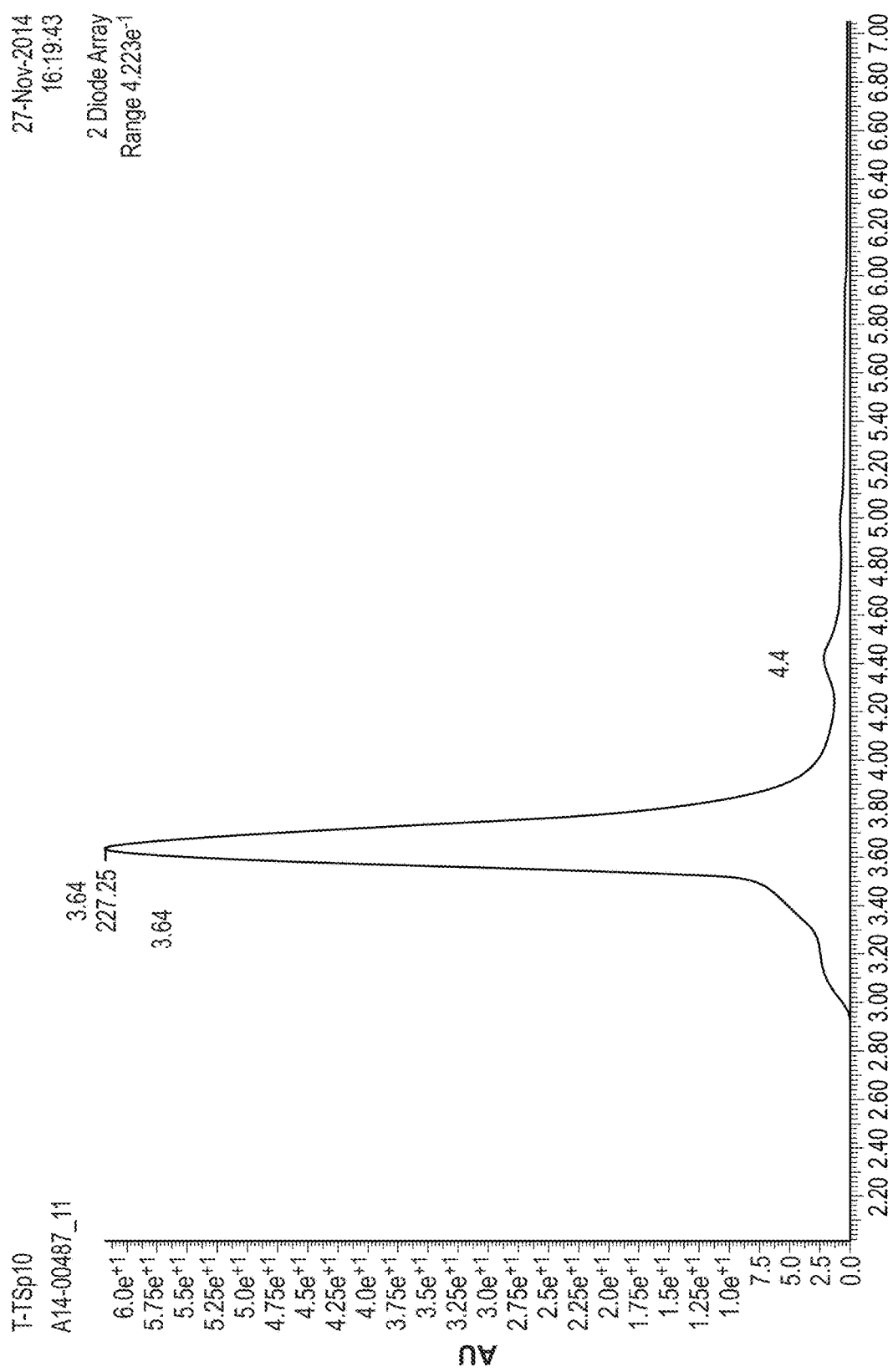
FIG. 18, Panels A-C provide SEC-MS data for an antibody (T-SP10) having a C-terminal light chain extension according to an embodiment of the present disclosure.
Figures 18B, 18C:
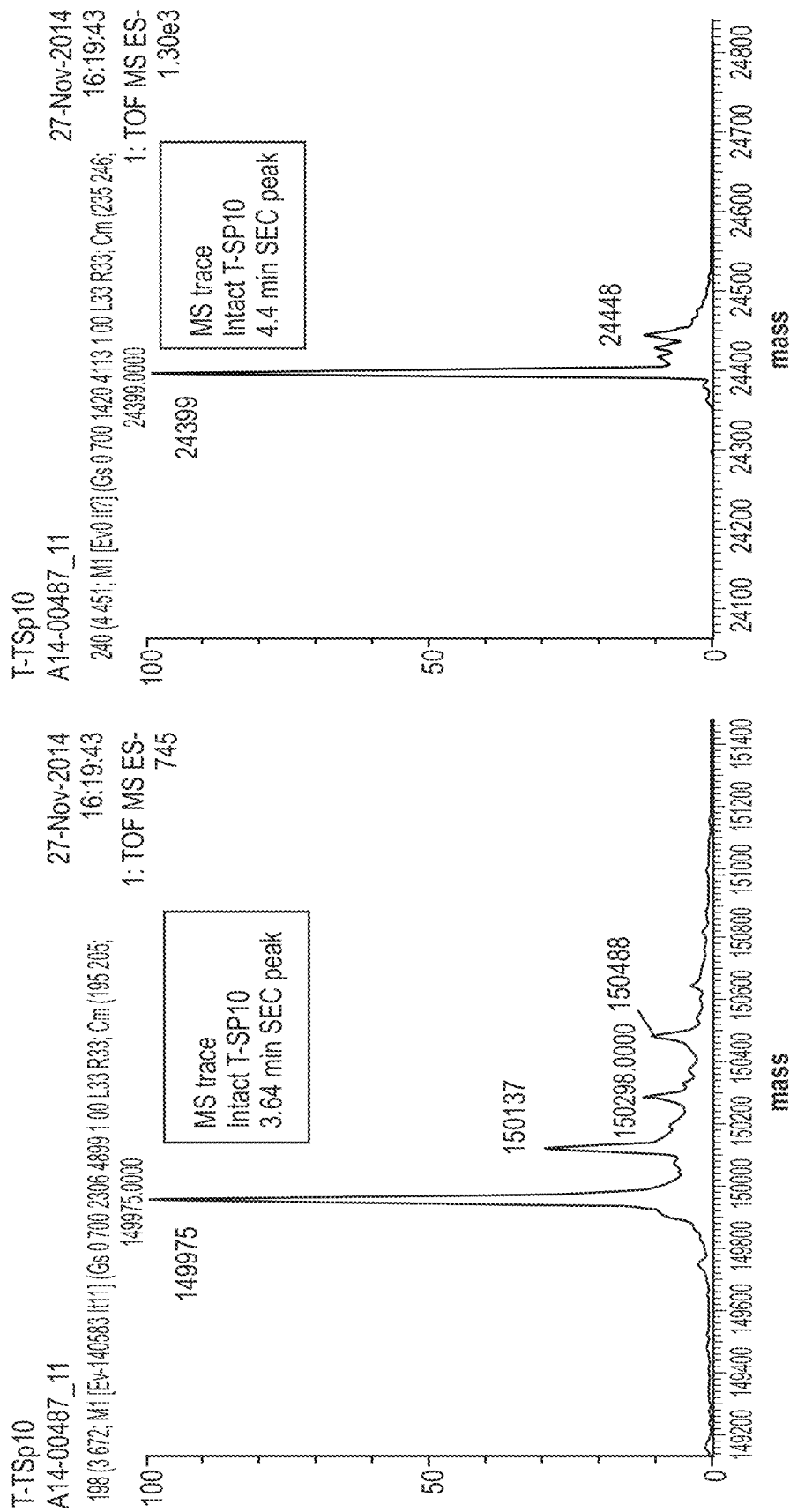
Figure 19A:
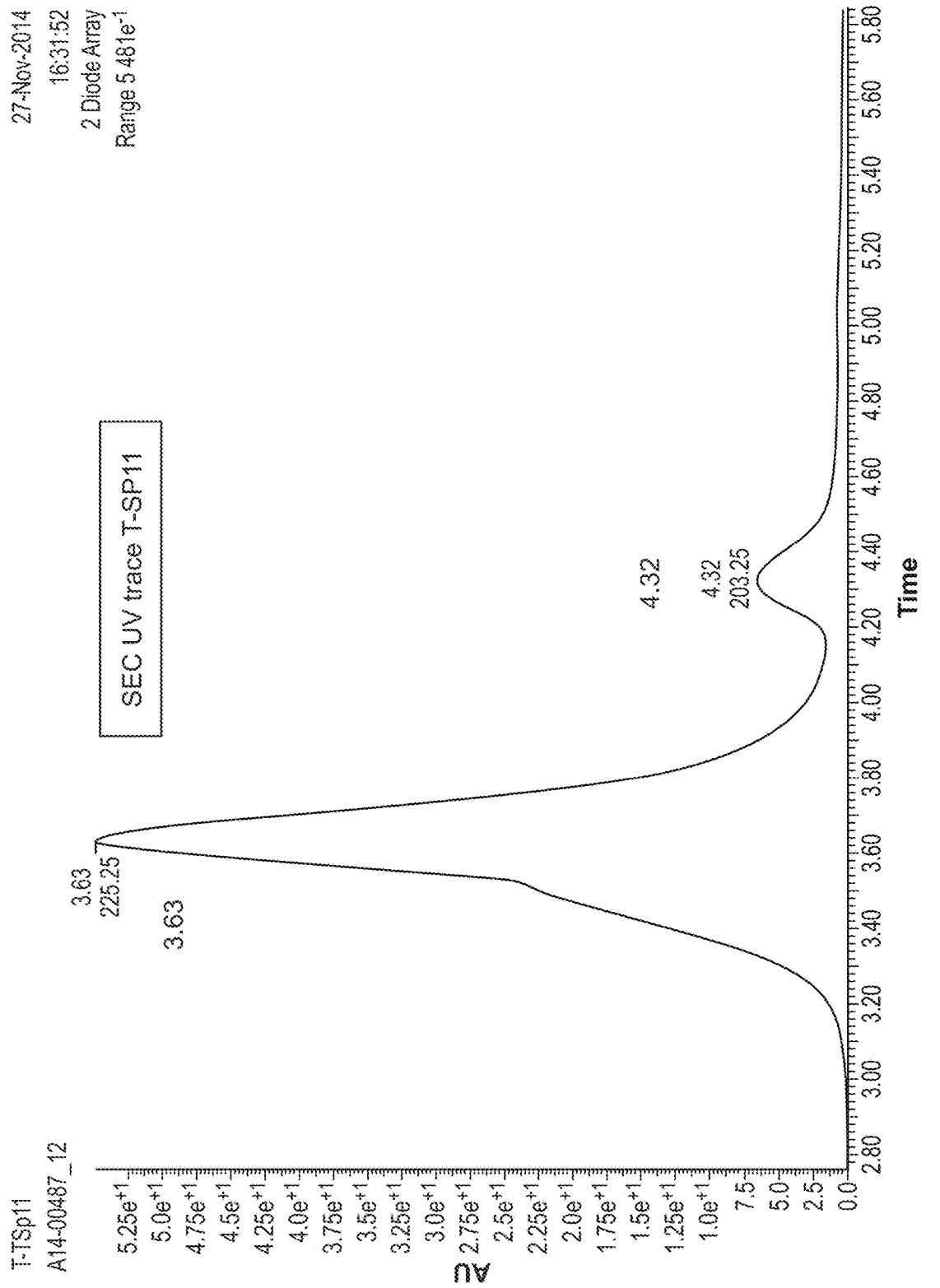
FIG. 19, Panels A-C provide SEC-MS data for an antibody (T-SP11) having a C-terminal light chain extension according to an embodiment of the present disclosure.
Figures 19B, 19C:
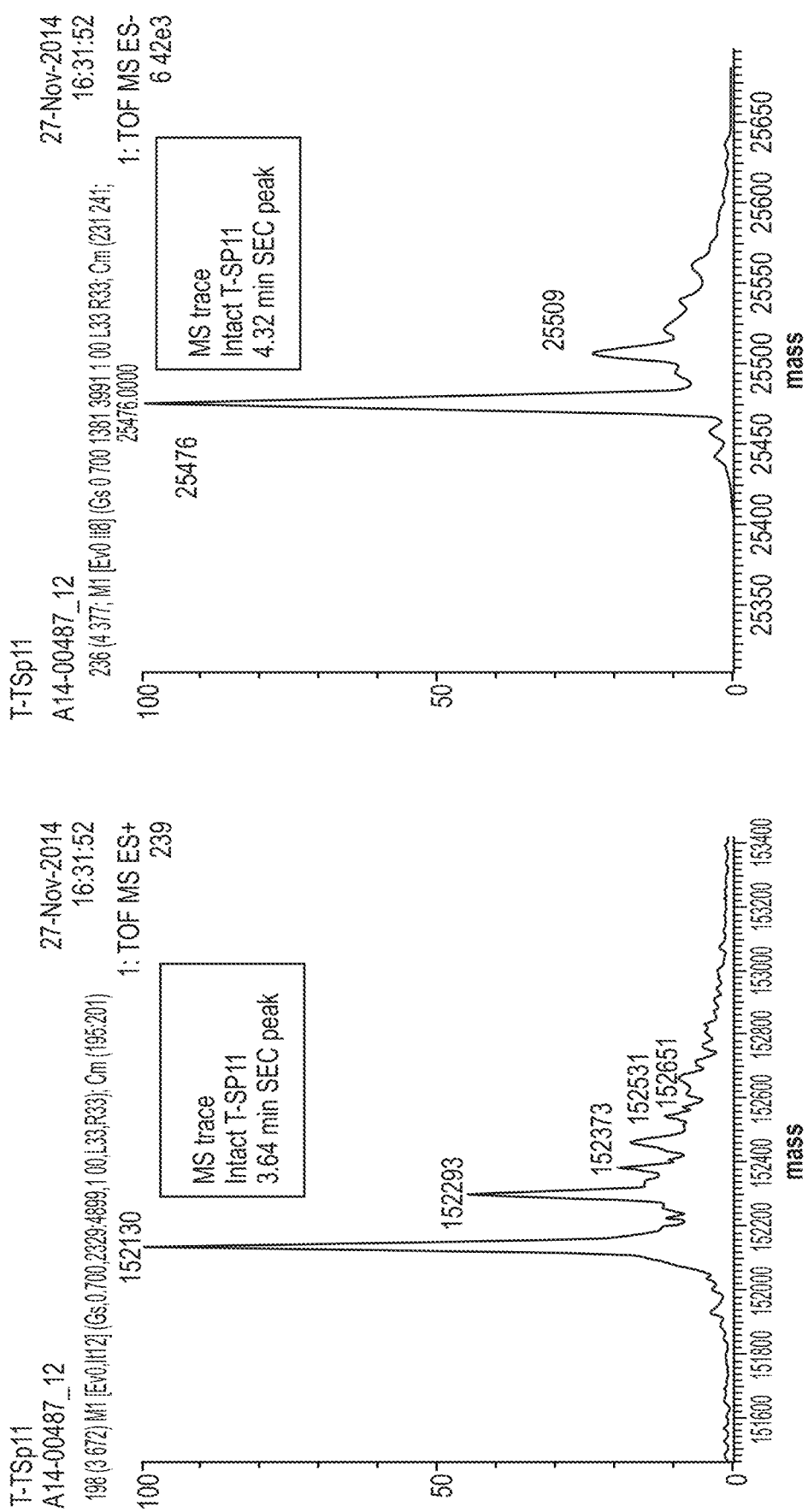
Figure 20:
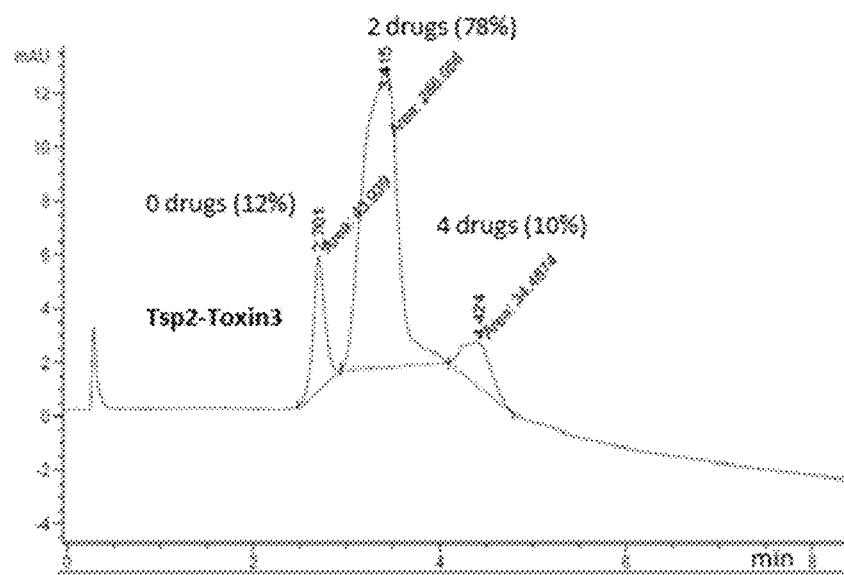
FIG. 20 shows an HIC chromatograph of conjugation reaction products for Tsp2-Toxin 3. The average drug loading value was 1.92.
Figure 21:
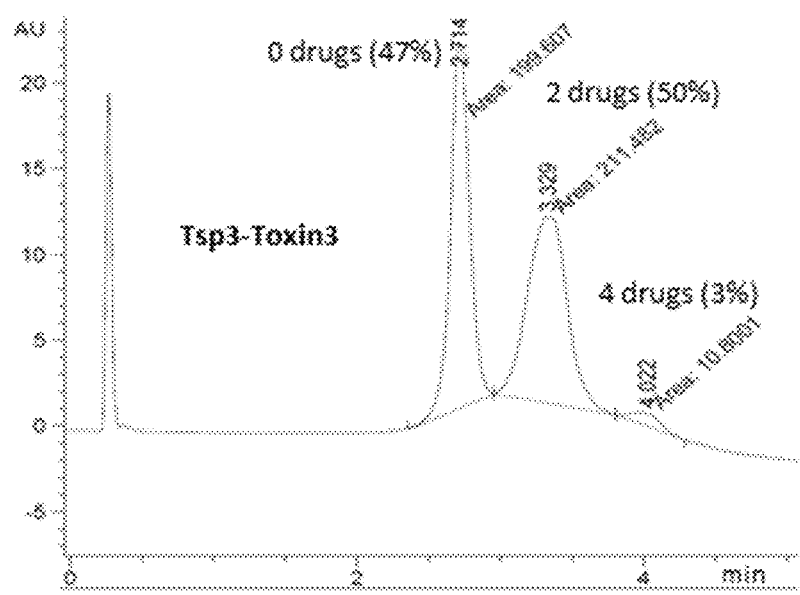
FIG. 21 shows an HIC chromatograph of conjugation reaction products for Tsp3-Toxin 3. The average drug loading value was 1.12.
Figure 22:
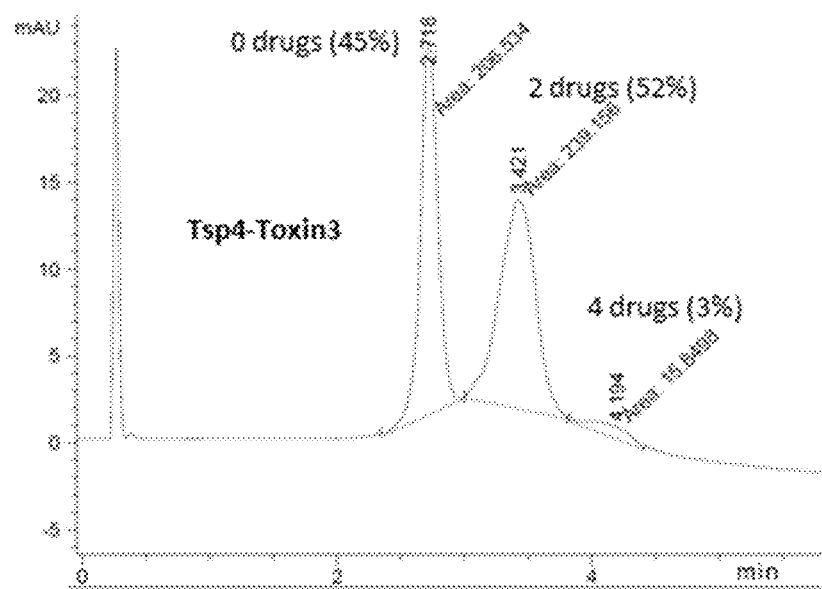
FIG. 22 shows an HIC chromatograph of conjugation reaction products for Tsp4-Toxin 3. The average drug loading value was 1.16.
Figure 23:
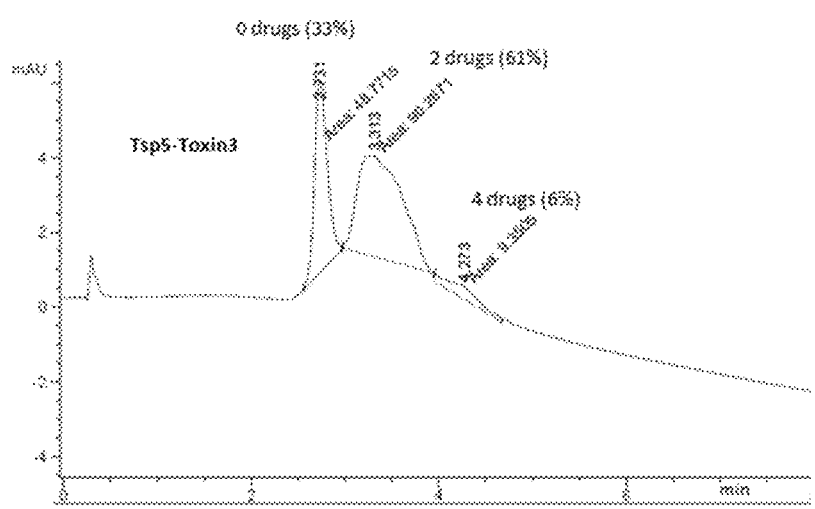
FIG. 23 shows an HIC chromatograph of conjugation reaction products for Tsp5-Toxin 3. The average drug loading value was 1.46.
Figure 24:
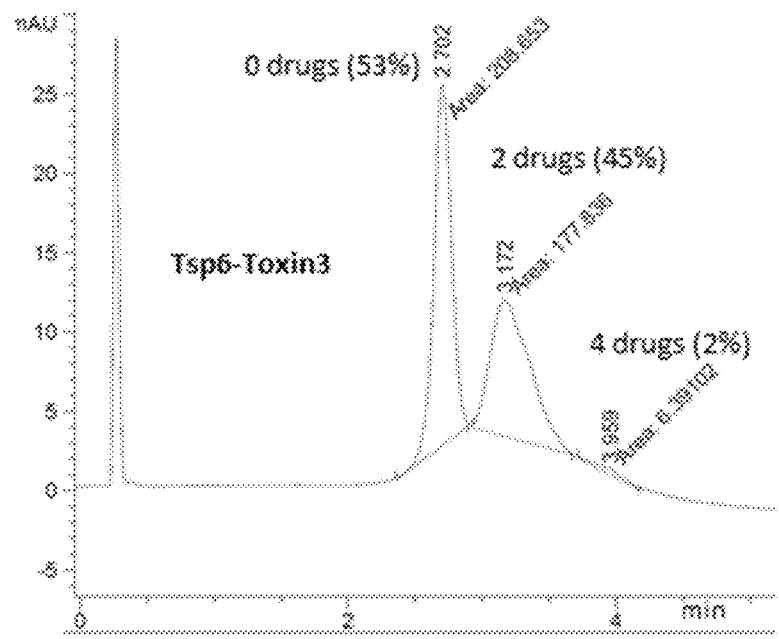
FIG. 24 shows an HIC chromatograph of conjugation reaction products for Tsp6-Toxin 3. The average drug loading value was 0.98.
Figure 25:
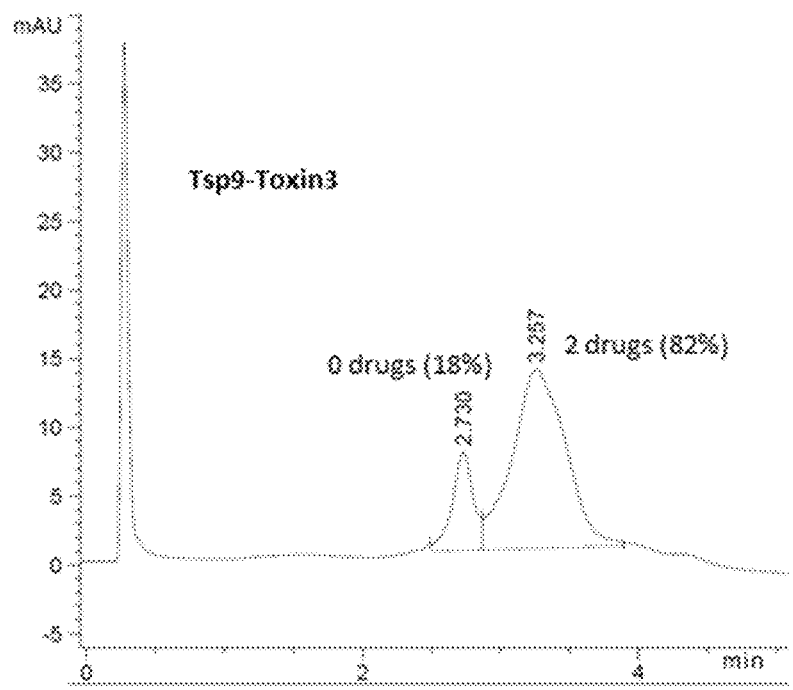
FIG. 25 shows an HIC chromatograph of conjugation reaction products for Tsp9-Toxin 3. The average drug loading value was 1.64.
Figure 26:
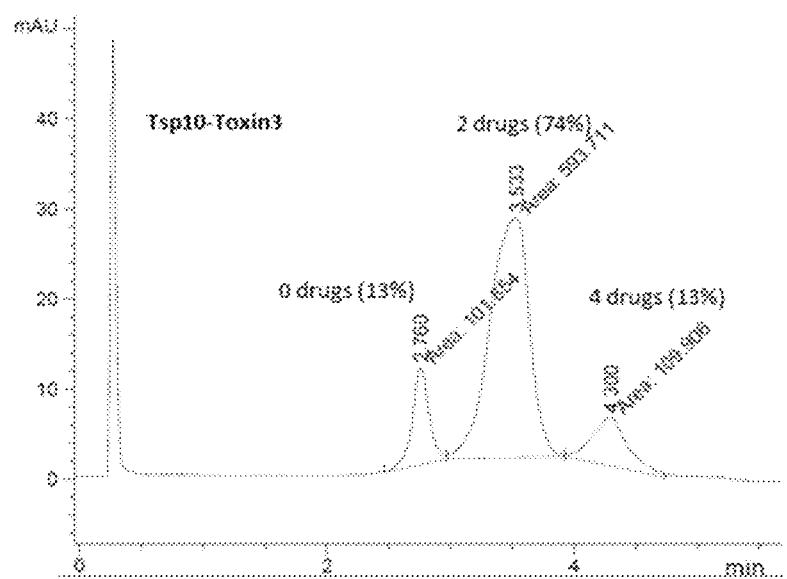
FIG. 26 shows an HIC chromatograph of conjugation reaction products for Tsp10-Toxin 3 (larger scale). The average drug loading value was 2.0.
Figure 27:
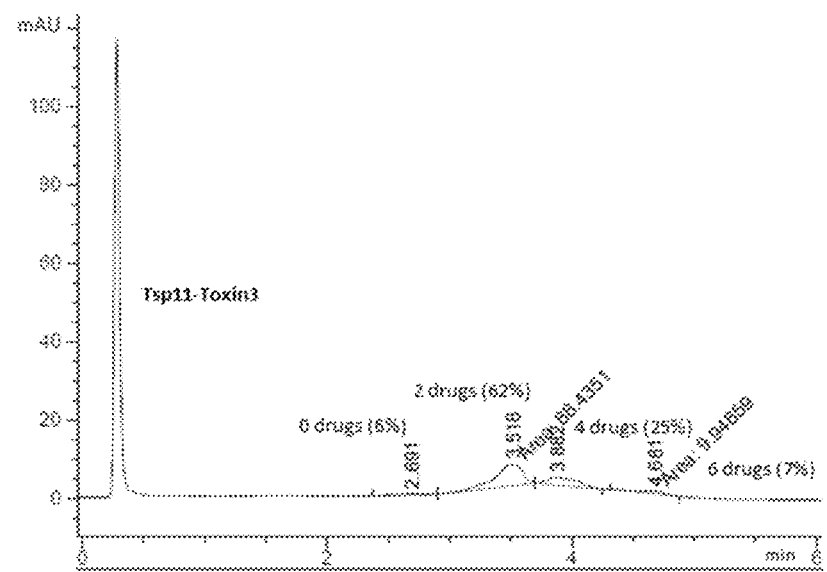
FIG. 27 shows an HIC chromatograph of conjugation reaction products for Tsp11-Toxin 3. The average drug loading value was 2.66.
Figure 28:
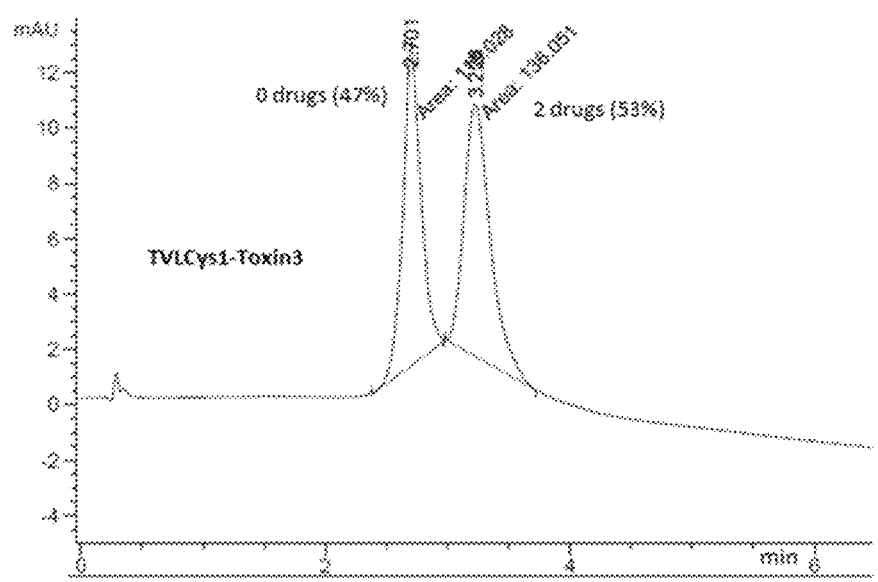
FIG. 28 shows an HIC chromatograph of conjugation reaction products for TVLCys1-Toxin3. The average drug loading value was 2.66.
Figure 29:
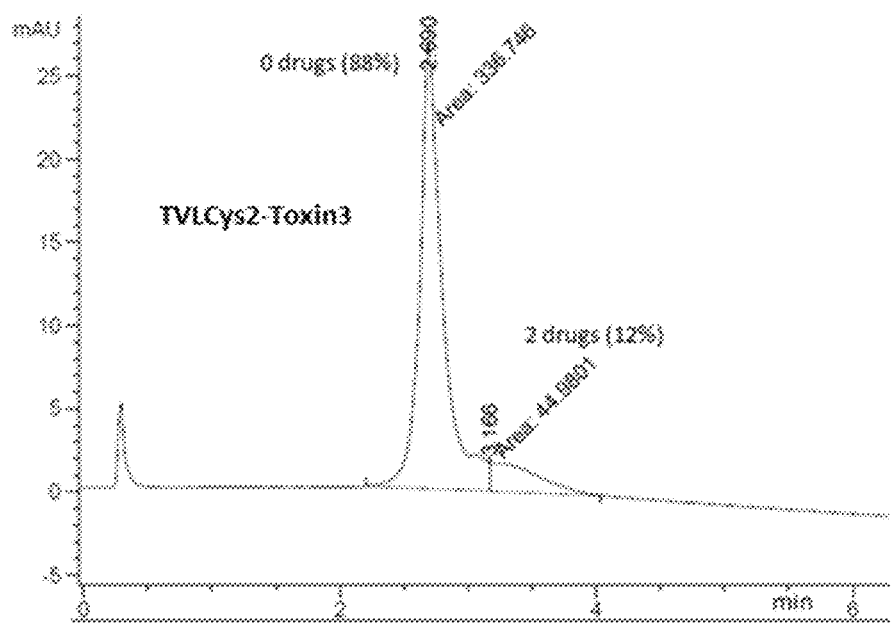
FIG. 29 shows an HIC chromatograph of conjugation reaction products for TVLCys2-Toxin3. The average drug loading value was 0.22.
Figure 32:
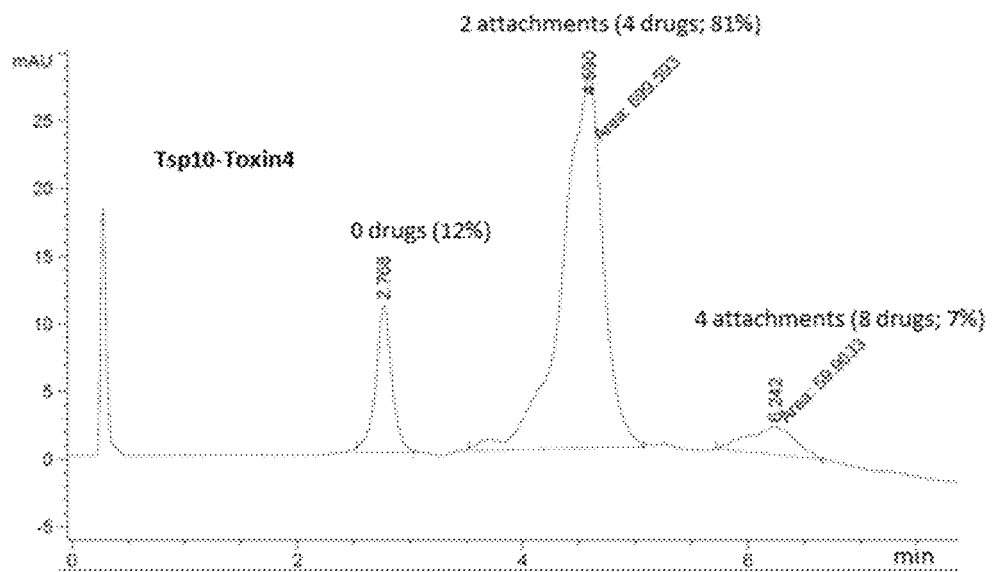
FIG. 32 shows an HIC chromatograph of conjugation reaction products for Tsp10-Toxin 4 (larger scale). The average drug loading value was 3.76, where average attachments was 1.88.
Figure 33:
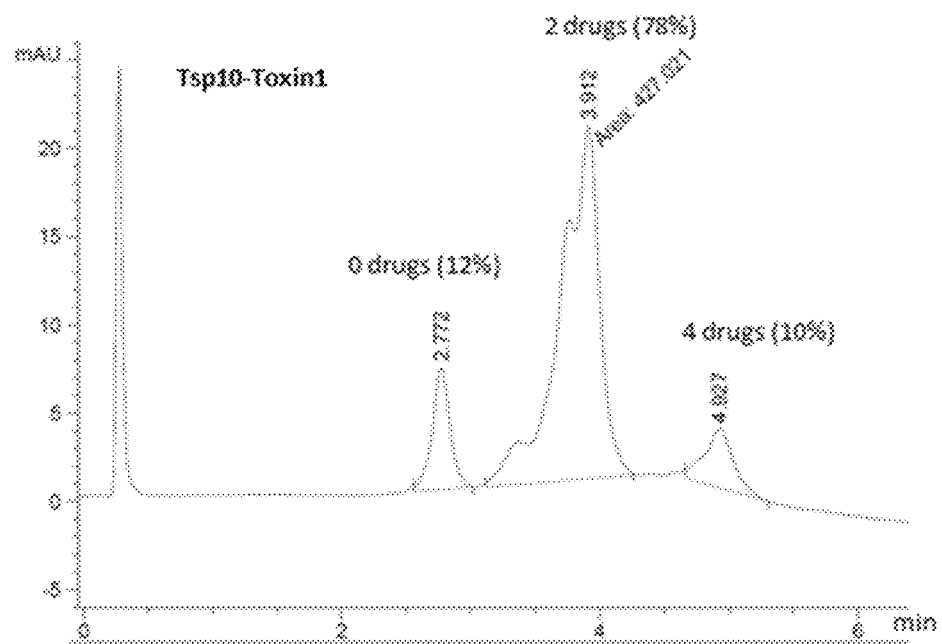
FIG. 33 shows an HIC chromatograph of conjugation reaction products for Tsp10-Toxin 1 (larger scale). The average drug loading value was 1.94.
Figure 34:
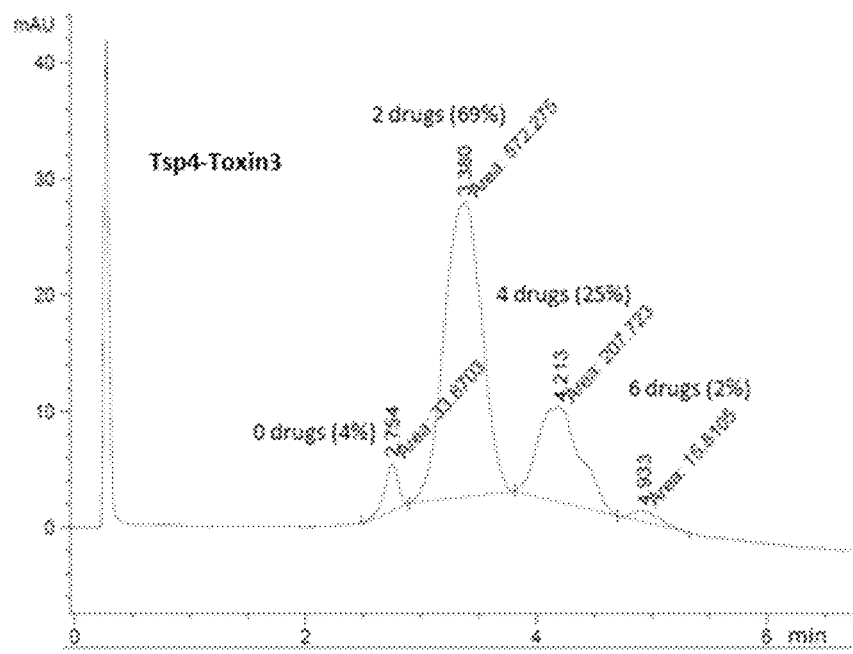
FIG. 34 shows an HIC chromatograph of conjugation reaction products for Tsp4-Toxin 3 (larger scale). The average drug loading value was 2.46.
Figure 35:
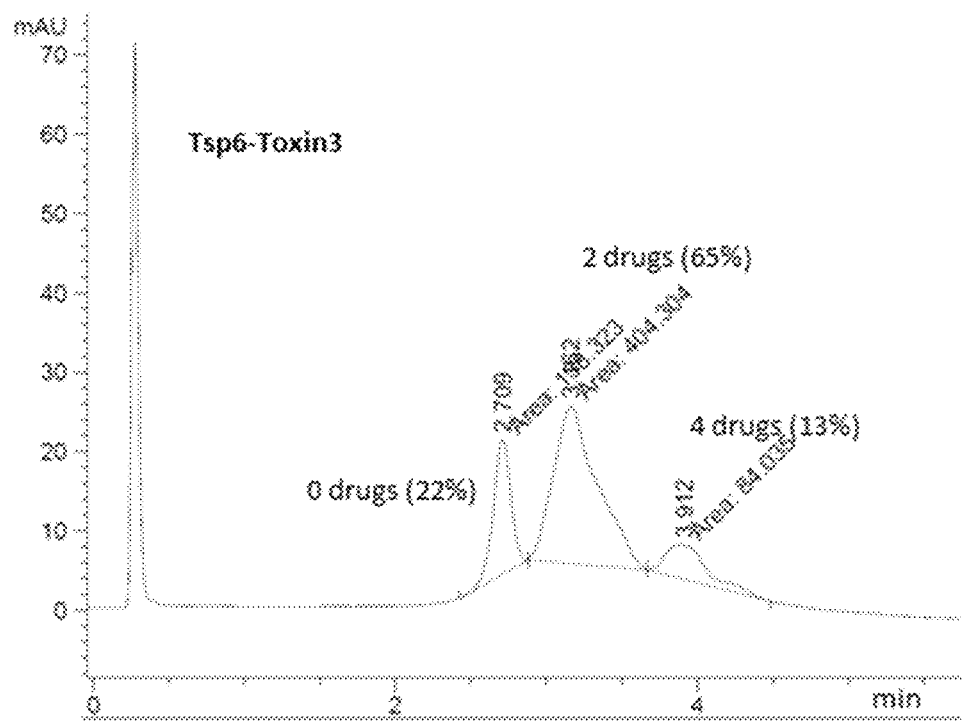
FIG. 35 shows an HIC chromatograph of conjugation reaction products for Tsp6-Toxin 3 (larger scale). The average drug loading value was 1.82.
Figure 36:
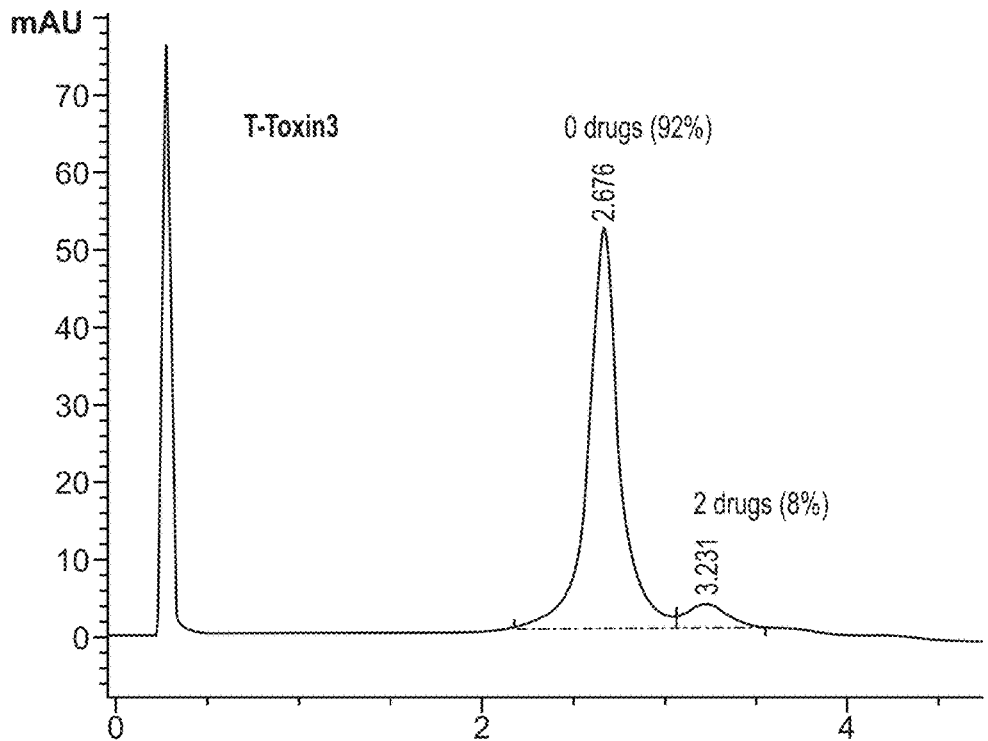
FIG. 36 shows an HIC chromatograph of conjugation reaction products for T-Toxin 3. The average drug loading value was 0.16.
Figure 37:
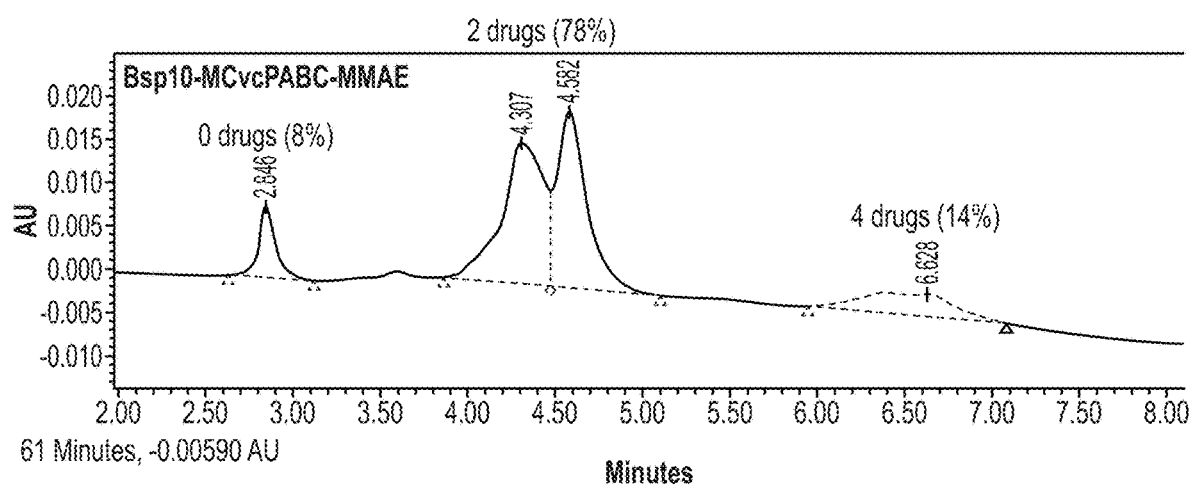
FIG. 37 shows an HIC chromatograph of conjugation reaction products for Bsp10-MCvcPABC-MMAE, where "B" is an abbreviation for Brentuximab anti-CD30 antibody. The average drug loading value was 2.12.
Figure 38:
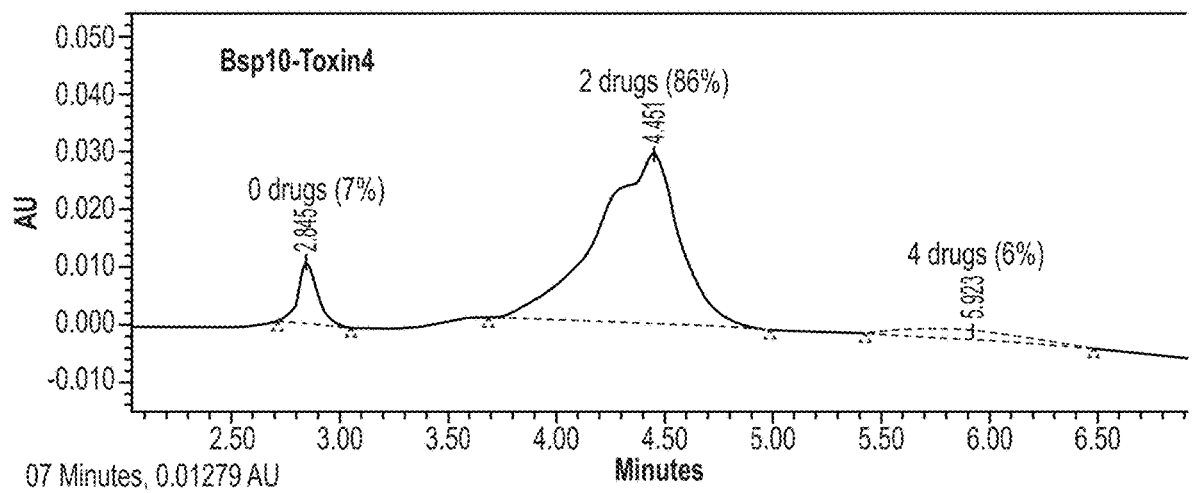
FIG. 38 shows an HIC chromatograph of conjugation reaction products for Bsp10-Toxin 4. The average drug loading value was 1.96.
Figure 39:
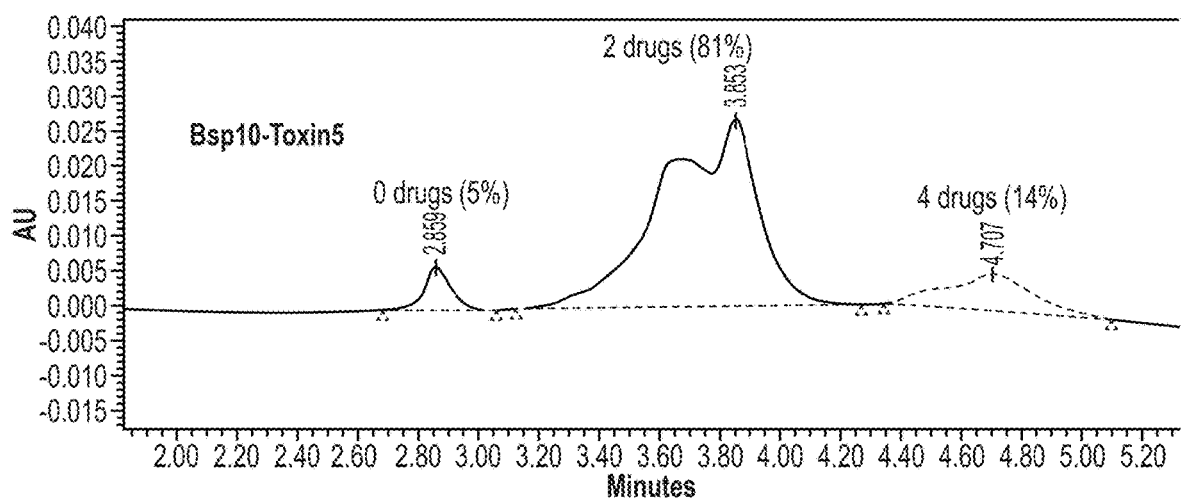
FIG. 39 shows an HIC chromatograph of conjugation reaction products for Bsp10-Toxin 5. The average drug loading value was 2.18.
Figure 40:
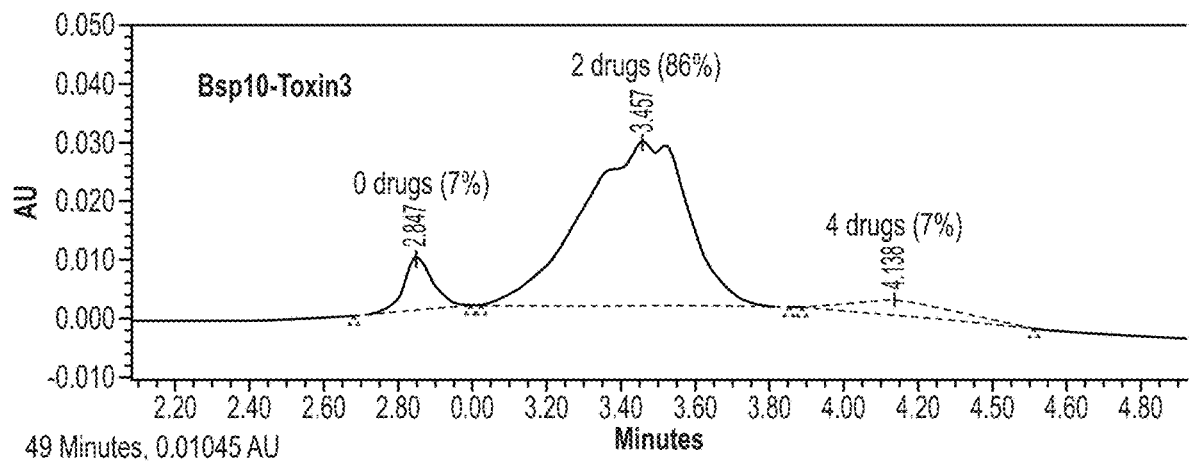
FIG. 40 shows an HIC chromatograph of conjugation reaction products for Bsp10-Toxin 3. The average drug loading value was 1.98.
Figure 41:
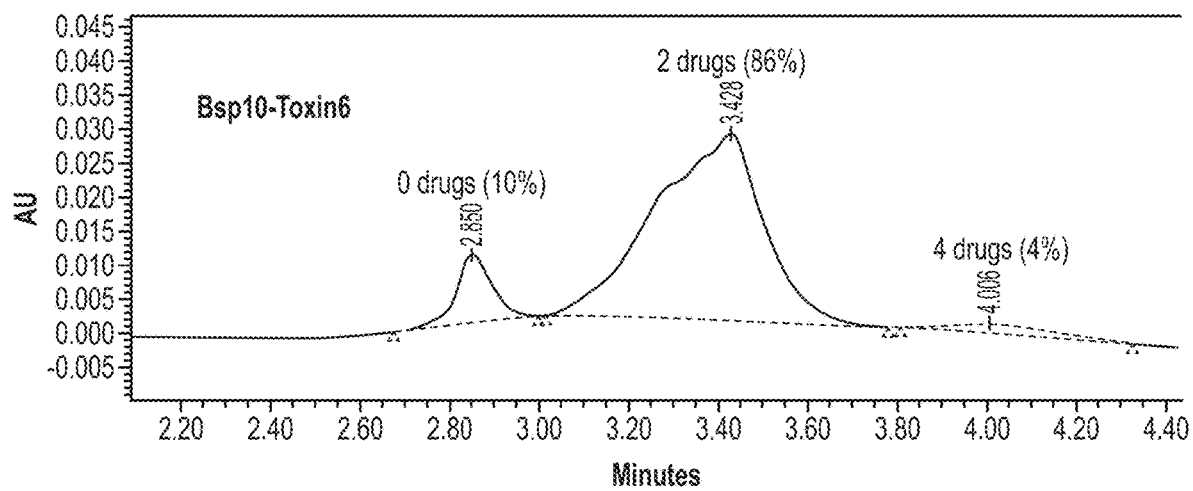
FIG. 41 shows an HIC chromatograph of conjugation reaction products for Bsp10-Toxin 6. The average drug loading value was 1.87.
Figure 42:
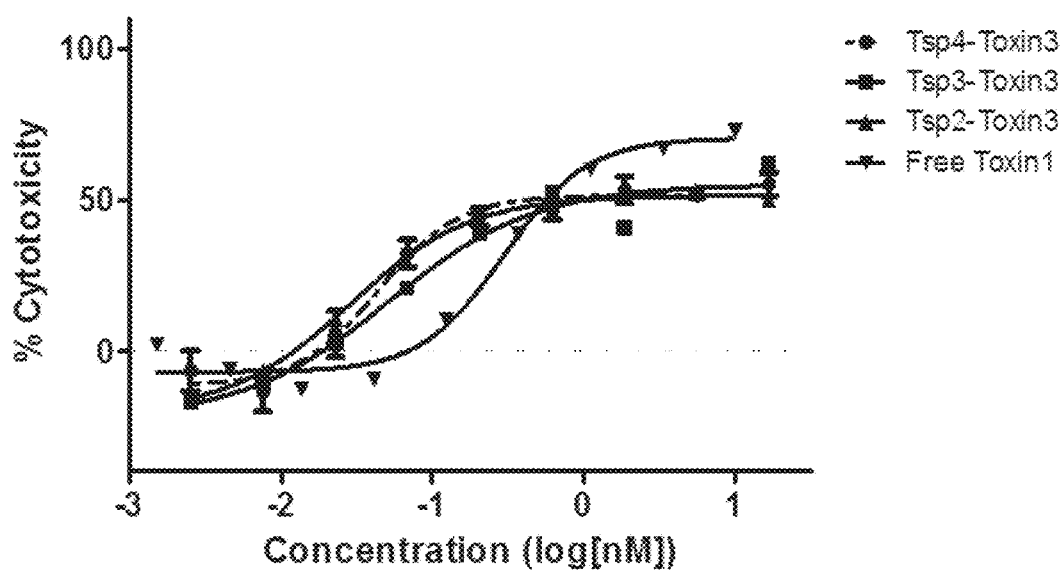
FIG. 42 shows a plot of in vitro cell proliferation assay results with Her2 expressing HCC1954 cells treated with Tsp4-Toxin3, Tsp3-Toxin3, Tsp2-Toxin3, and Free Toxin1.
Figure 43:
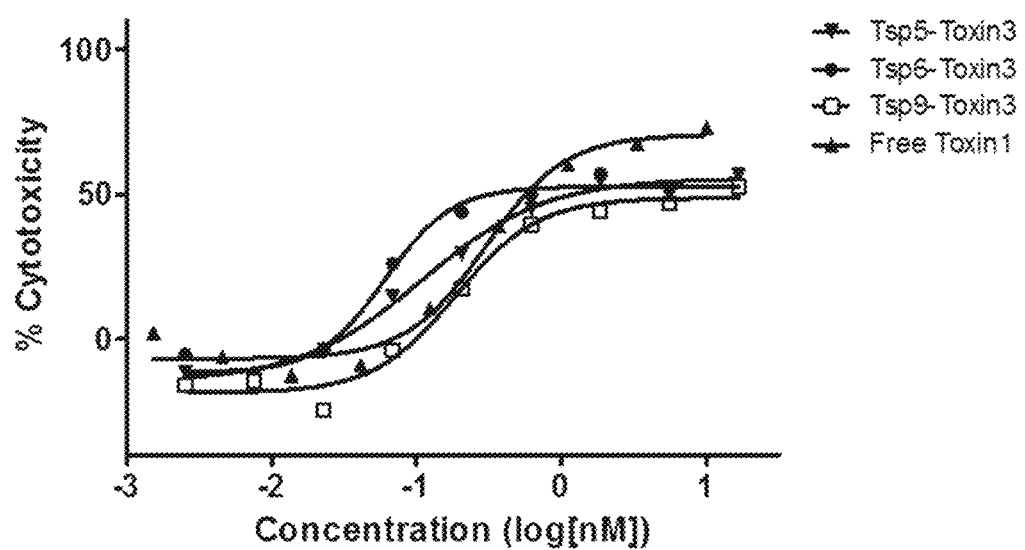
FIG. 43 shows a plot of in vitro cell proliferation assay results with Her2 expressing HCC1954 cells treated with Tsp5-Toxin3, Tsp6-Toxin3, Tsp9-Toxin3, and Free Toxin1.
Figure 44:
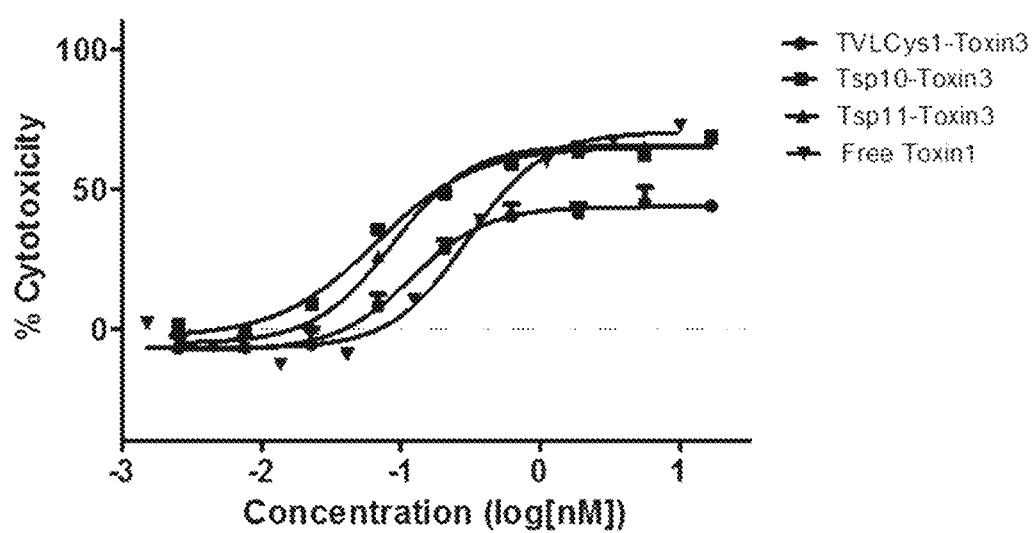
FIG. 44 shows a plot of in vitro cell proliferation assay results with Her2 expressing HCC1954 cells treated with Tsp10-Toxin3, Tsp11-Toxin3, TVLCys1-Toxin3, and Free Toxin1.
Figure 45:
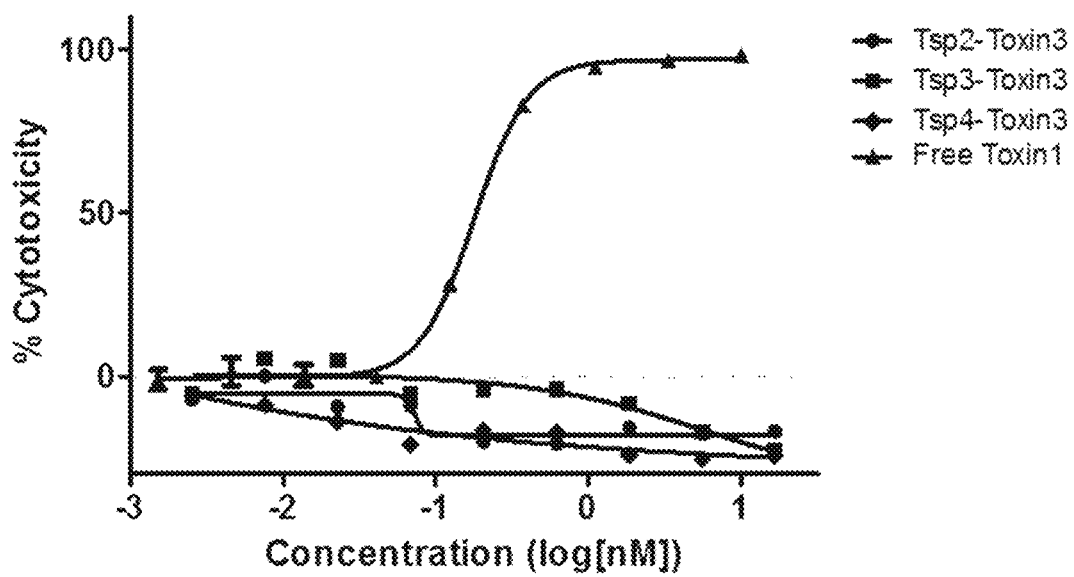
FIG. 45 shows a plot of in vitro cell proliferation assay results with HER2 antigen negative Jurkat cells treated with Tsp4-Toxin3, Tsp3-Toxin3, Tsp2-Toxin3, and Free Toxin1.
Figure 46:
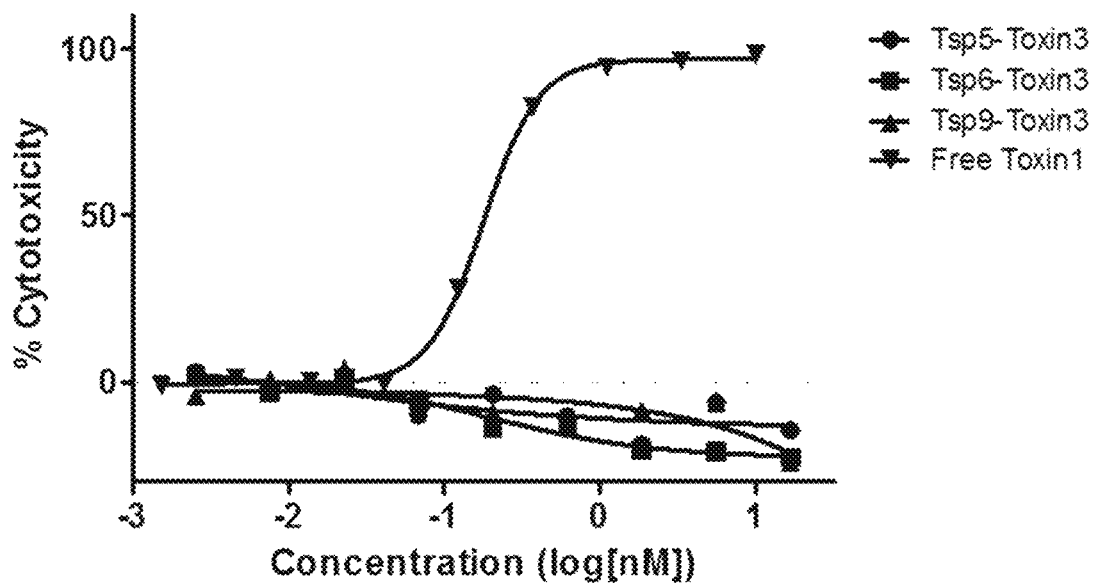
FIG. 46 shows a plot of in vitro cell proliferation assay results with HER2 antigen negative Jurkat cells treated with Tsp5-Toxin3, Tsp6-Toxin3, Tsp9-Toxin3, and Free Toxin1.
Figure 47:
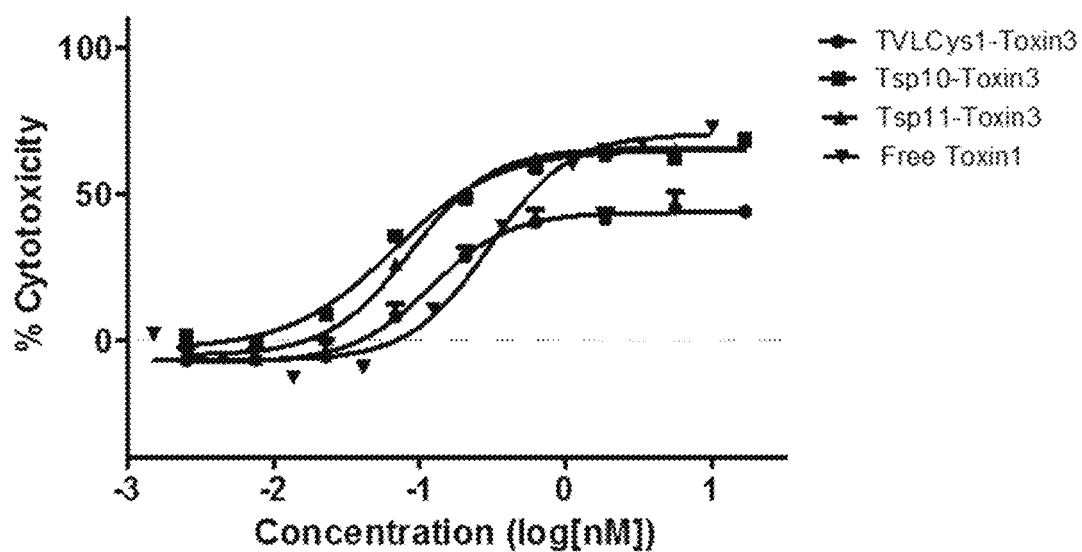
FIG. 47 shows a plot of in vitro cell proliferation assay results with HER2 antigen positive HCC1954 cells treated with Tsp10-Toxin3, Tsp11-Toxin3, TVLCys1-Toxin3, and Free Toxin1.
Figure 48:
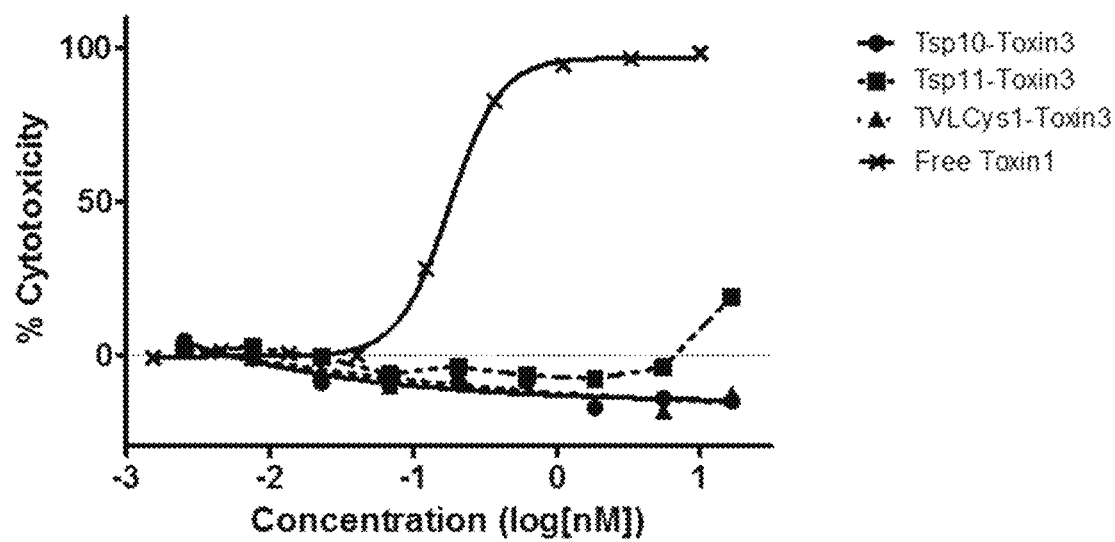
FIG. 48 shows a plot of in vitro cell proliferation assay results with HER2 antigen negative Jurkat cells treated with Tsp10-Toxin3, Tsp11-Toxin3, TVLCys1-Toxin3, and Free Toxin1.
Figure 49:
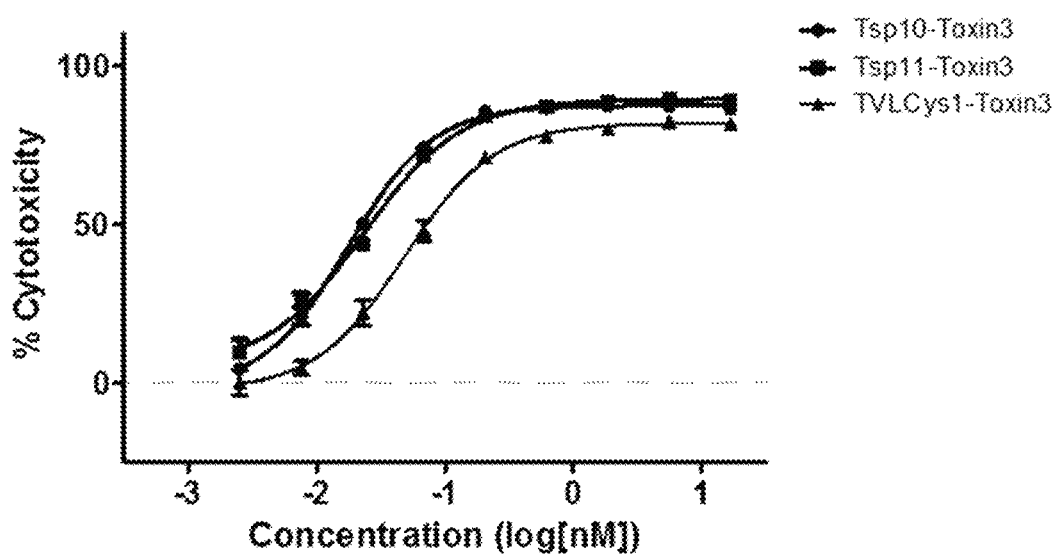
FIG. 49 shows a plot of in vitro cell proliferation assay results with HER2 antigen positive N87 cells treated with Tsp10-Toxin3, Tsp11-Toxin3, and TVLCys1-Toxin3.
Figure 50:
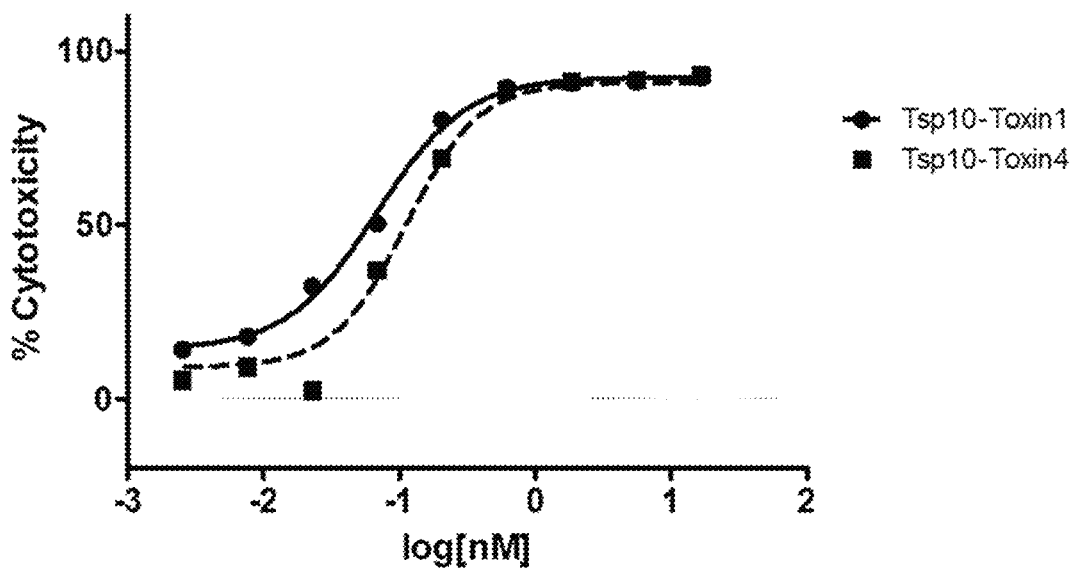
FIG. 50 shows a plot of in vitro cell proliferation assay results with HER2 antigen positive N87 cells treated with Tsp10-Toxin1 and Tsp10-Toxin4.
Figure 51:
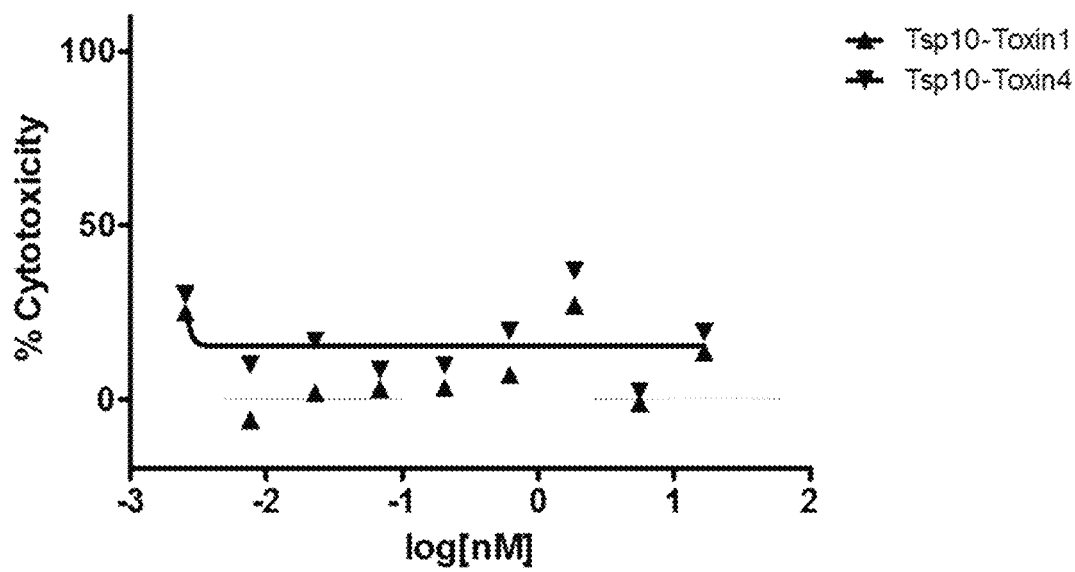
FIG. 51 shows a plot of in vitro cell proliferation assay results with HER2 antigen negative Jurkat cells treated with Tsp10-Toxin1, and Tsp10-Toxin4.
Figure 52:
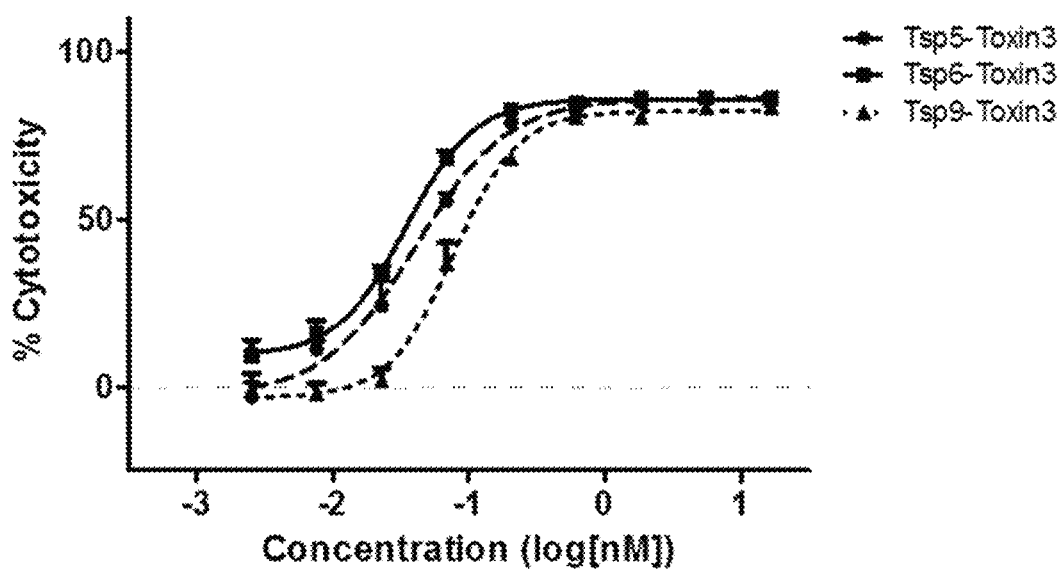
FIG. 52 shows a plot of in vitro cell proliferation assay results with HER2 antigen positive N87 cells treated with Tsp5-Toxin3, Tsp6-Toxin3, and Tsp9-Toxin3.
Figure 53:
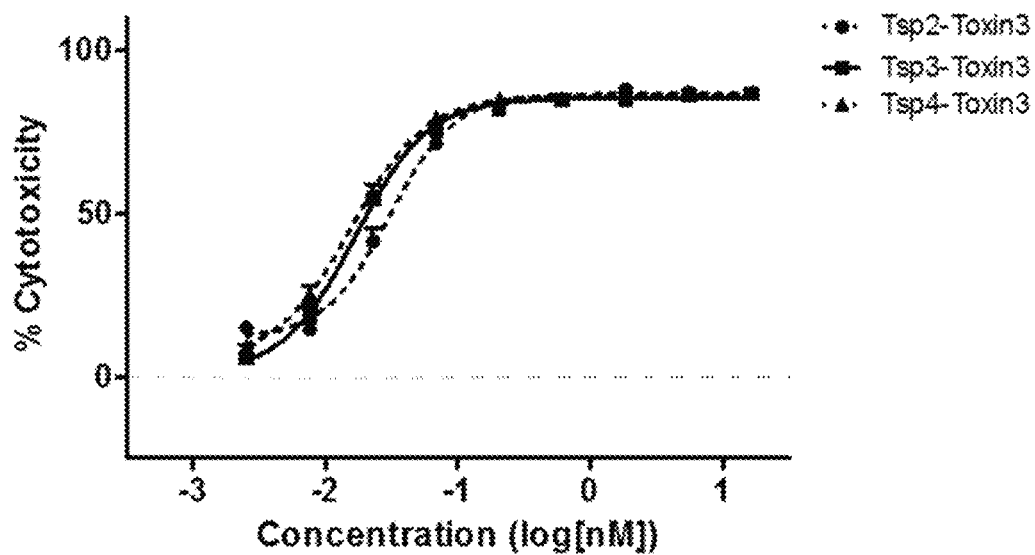
FIG. 53 shows a plot of in vitro cell proliferation assay results with HER2 antigen positive N87 cells treated with Tsp2-Toxin3, Tsp3-Toxin3, and Tsp4-Toxin3.
Figure 54:
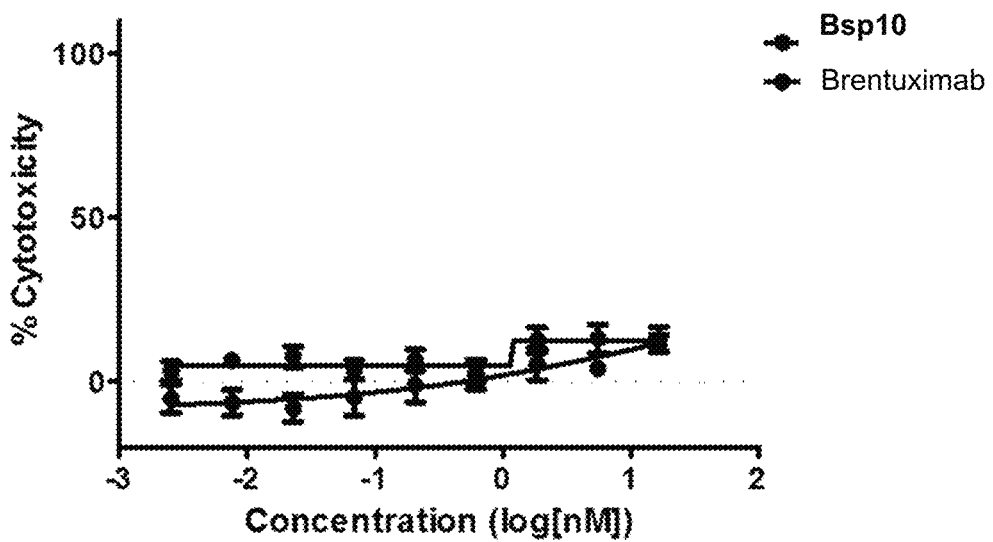
FIG. 54 shows a plot of in vitro cell proliferation assay results with CD30 antigen positive Karpas 299 cells treated with Brentuximab, and Bsp10.
Figure 55:
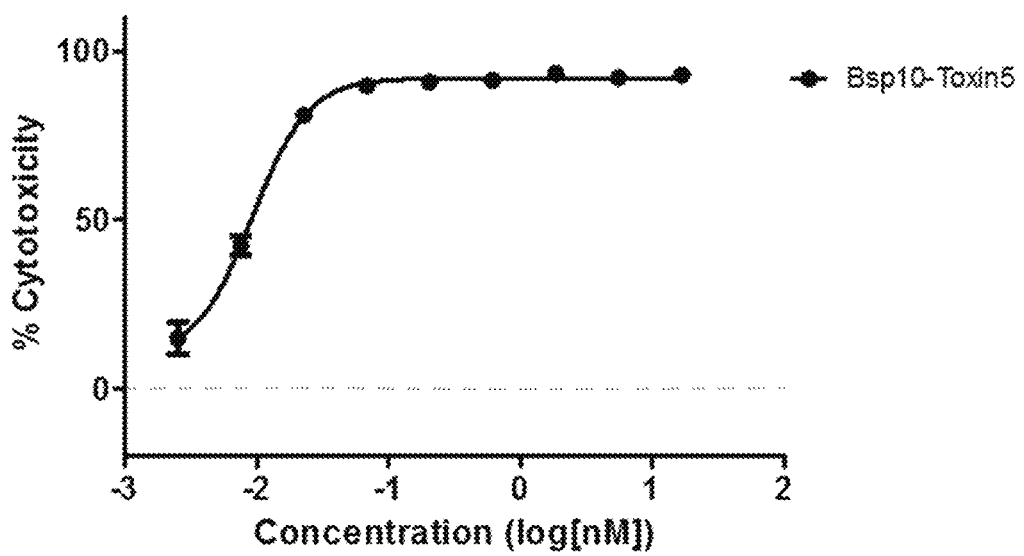
FIG. 55 shows a plot of in vitro cell proliferation assay results with CD30 antigen positive Karpas 299 cells treated with Bsp10-Toxin5.
Figure 56:
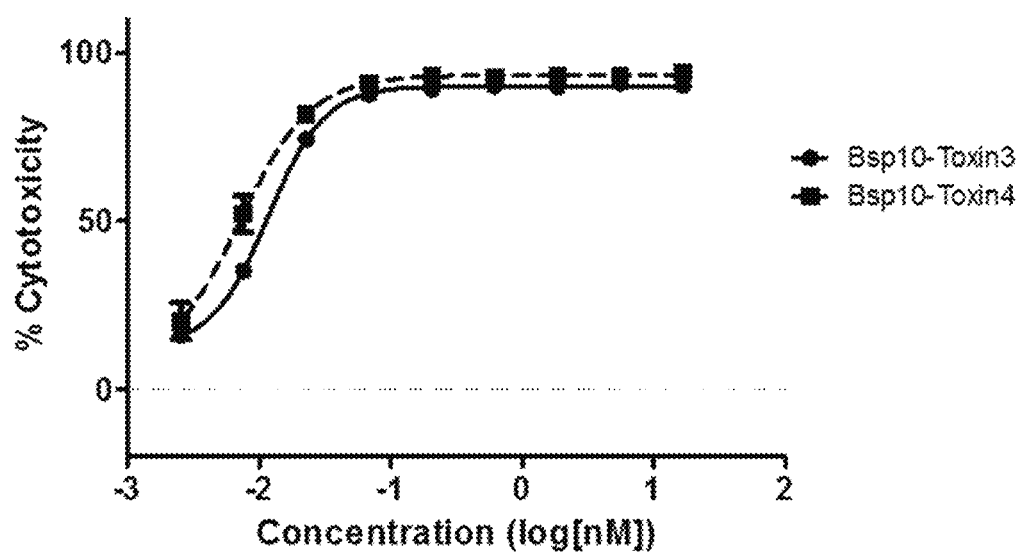
FIG. 56 shows a plot of in vitro cell proliferation assay results with CD30 antigen positive Karpas 299 cells treated with Bsp10-Toxin3 and Bsp10-Toxin4.
Figure 57:
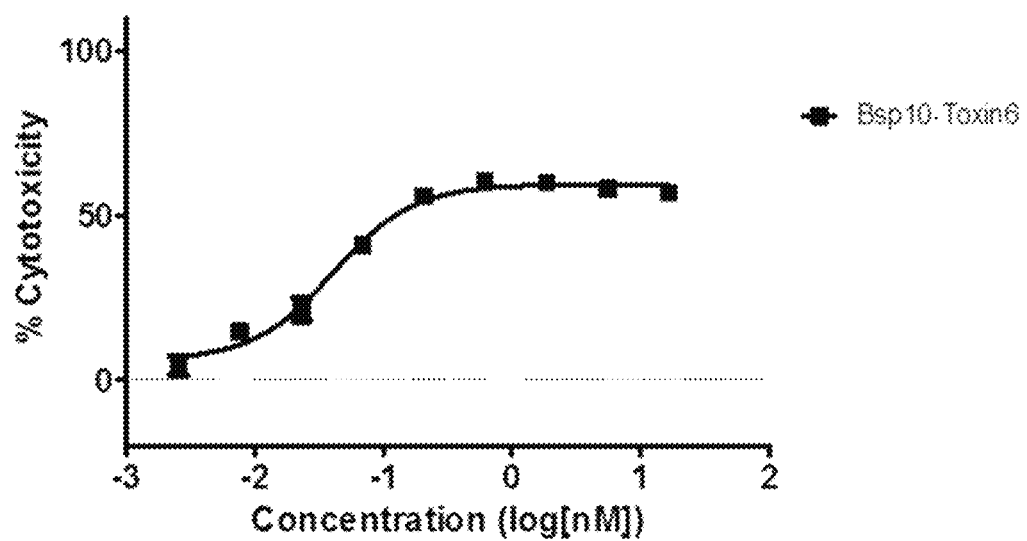
FIG. 57 shows a plot of in vitro cell proliferation assay results with CD30 antigen positive Karpas 299 cells treated with Bsp10-Toxin6.
Figure 58:
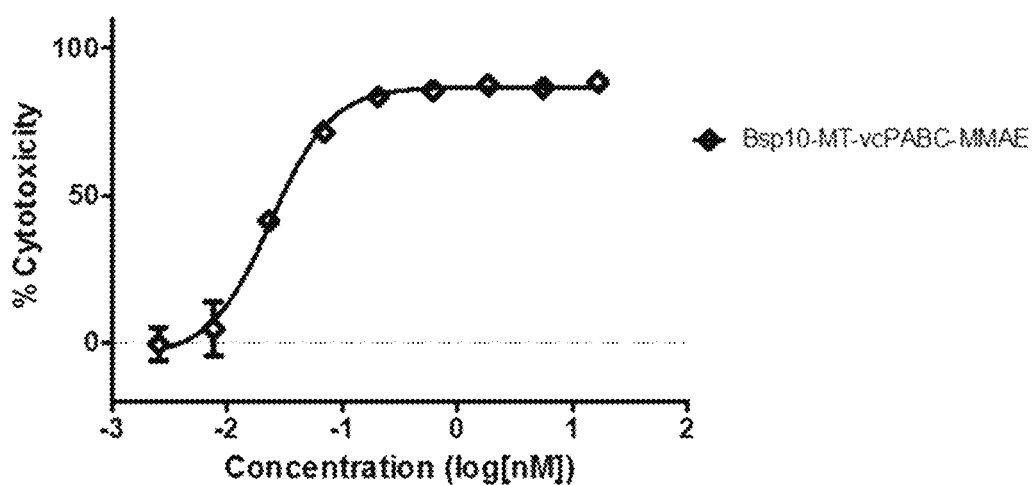
FIG. 58 shows a plot of in vitro cell proliferation assay results with CD30 antigen positive Karpas 299 cells treated with Bsp10-MCvcPABC-MMAE.
Figure 59:
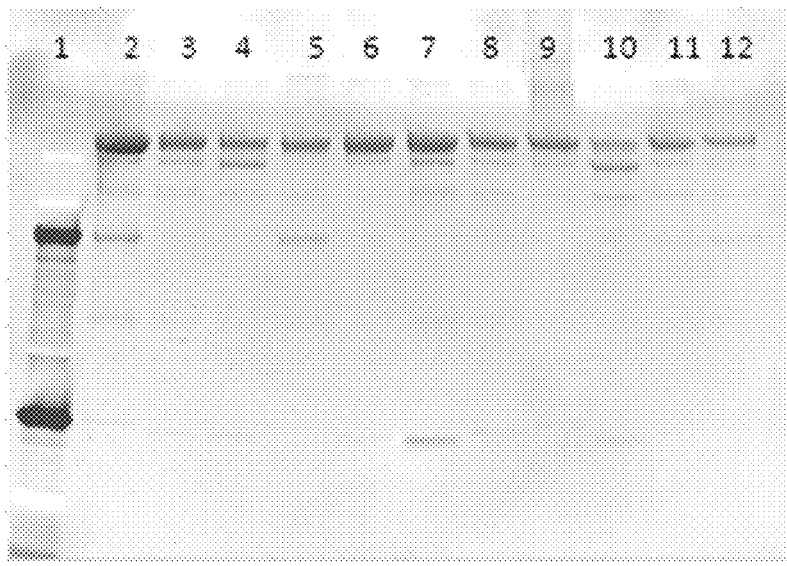
FIG. 59 is a gel image showing non-reducing denaturing polyacrylamide gel electrophoresis (PAGE) of trastuzumab light chain extension variants after purification on immobilized protein A. Left to right, lanes 1-12: molecular size marker; TSp2; TSp3; TSp4; TSp5; TSp6; TSp9; TSp10; TSp11; TVLCys1; TVLCys2; TVLCys4. The size marker ladder in lane 1 indicates the intact proteins are about 150 kDa.
Figure 60:
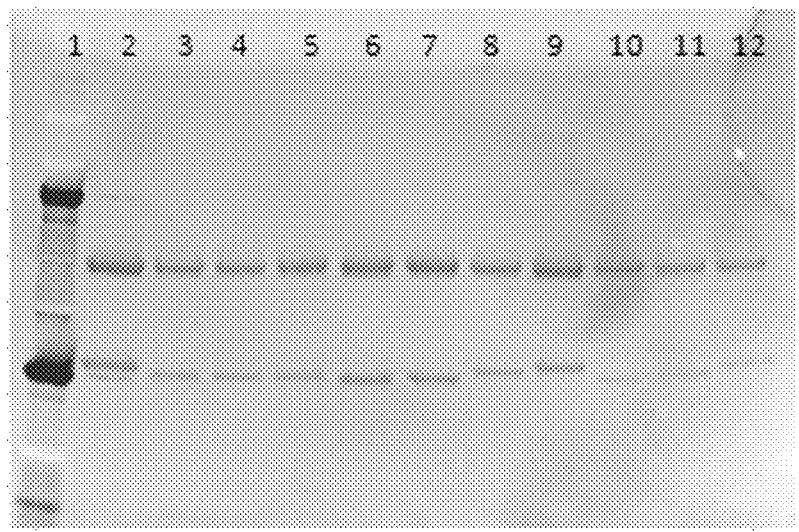
FIG. 60 is a gel image showing reducing (+DTT) denaturing PAGE of trastuzumab light chain extension variants. Left to right, lanes 1-12: molecular size marker; TSp2; TSp3; TSp4; TSp5; TSp6; TSp9; TSp10; TSp11; TVLCys1; TVLCys2; TVLCys4. The size marker ladder in lane 1 indicates the reduced proteins contain heavy chain fragments of about 50 kDa, and light chain fragments of about 25 kDa.
Figure 61:
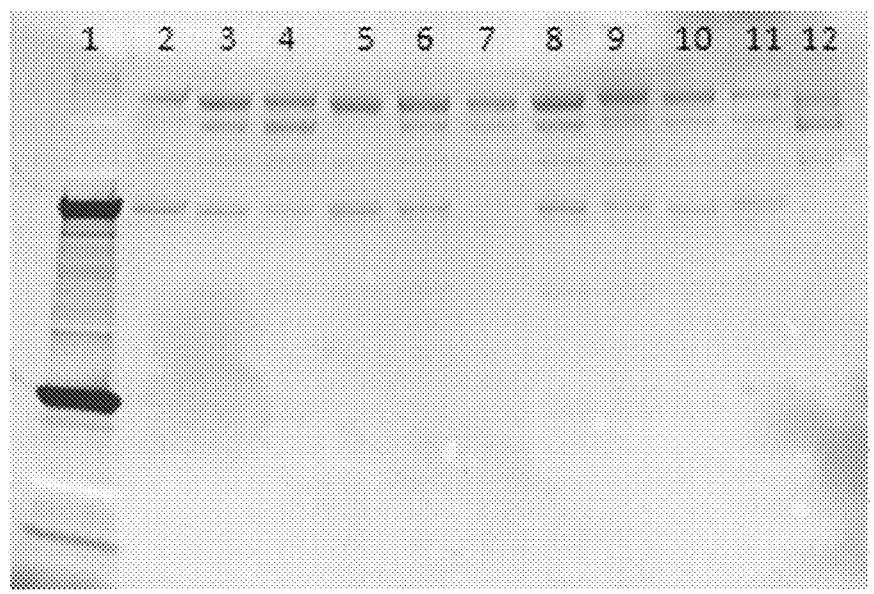
FIG. 61 is a gel image showing non-reducing denaturing PAGE of trastuzumab light chain extension antibody drug conjugates. Left to right, lanes 1-12: molecular size marker; Tsp2-Toxin3 (DAR 1.92); Tsp3-Toxin3 (DAR 1.88); Tsp4-Toxin3 (DAR 2.06); Tsp5-Toxin3 (DAR 1.46); Tsp6-Toxin3 (DAR 1.80); Tsp9-Toxin3 (DAR 1.32); Tsp10-Toxin3 (DAR 2.12); Tsp10-Toxin4 (DAR 1.66); Tsp10-Toxin 1 (DAR 2.04); Tsp11-Toxin3 (DAR 2.02); TVLCys1-Toxin3 (DAR 1.06).
Figure 62:
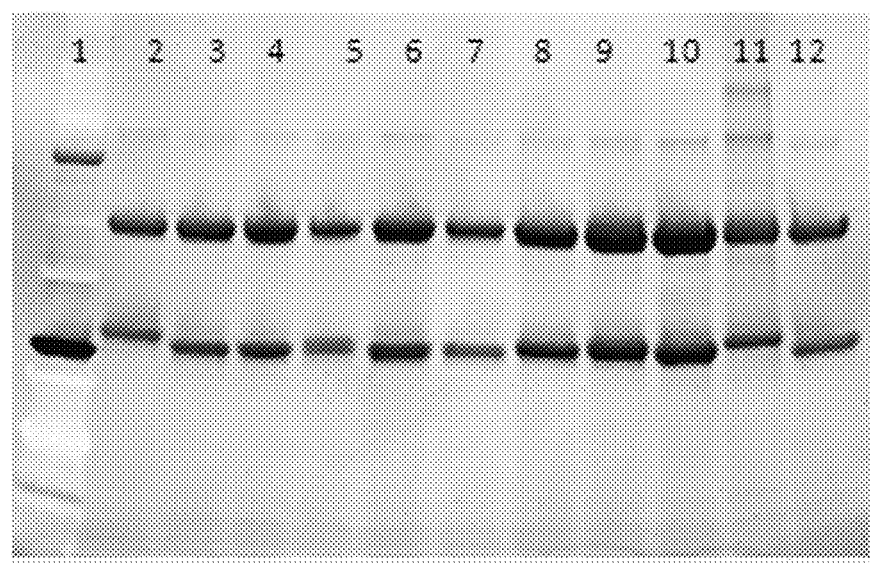
FIG. 62 is a gel image showing reducing (+DTT) denaturing PAGE of trastuzumab light chain extension antibody drug conjugates. Left to right, lanes 1-12: molecular size marker; Tsp2-Toxin3 (DAR 1.92); Tsp3-Toxin3 (DAR 1.88); Tsp4-Toxin3 (DAR 2.06); Tsp5-Toxin3 (DAR 1.46); Tsp6-Toxin3 (DAR 1.80); Tsp9-Toxin3 (DAR 1.32); Tsp10-Toxin3 (DAR 2.12); Tsp10-MP-Toxin4 (DAR 1.66); Tsp10-Toxin 1 (DAR 2.04); Tsp11-Toxin3 (DAR 2.02); TVLCys1-Toxin3 (DAR 1.06).

Results for an antibody (T-VLcys1) having the extension of SEQ ID NO:60 are shown in FIG. 9, Panels A-C. Results for an antibody (T-VLcys2) having the extension of SEQ ID NO:63 are shown in FIG. 10, Panels A-C. Results for an antibody (T-VLcys4) having the extension of SEQ ID NO:64 are shown in FIG. 11, Panels A and B. Results for an antibody having the light chain of SEQ ID NO:105 are shown in FIG. 12, Panels A and B. Results for an antibody having the light chain of SEQ ID NO:106 are shown in FIG. 13, Panels A-C. Results for an antibody having the light chain of SEQ ID NO:107 are shown in FIG. 14, Panels A-C. Results for an antibody having the light chain of SEQ ID NO:108 are shown in FIG. 15, Panels A and B. Results for an antibody having the light chain of SEQ ID NO:109 are shown in FIG. 16, Panels A-C. Results for an antibody having the light chain of SEQ ID NO:110 are shown in FIG. 17, Panels A-C. Results for an antibody having the light chain of SEQ ID NO:113 are shown in FIG. 18, Panels A-C. Results for an antibody having the light chain of SEQ ID NO:114 are shown in FIG. 19, Panels A-C.

Example 18

In Vitro Cell Proliferation Assays

In vitro cell proliferation assays were performed using a procedure similar to that described in Example 5 above, by treating HER2 expressing HCC1954 cells, HER2 expressing N87 cells, and HER2 antigen negative Jurkat cells with various trastuzumab ("T")-based ADCs and controls. "Free Toxin 1" is Toxin 3 as defined above in its free form (i.e., not conjugated to an antibody). Results are shown in FIGS. 42-53 and summarized below in Tables 7 and 8.

TABLE 7

In vitro cell proliferation assay results (HCC1954 and Jurkat cells)

| Cell Line | Sample | DAR | EC50 (nM) |
|---|---|---|---|
| HCC1954 | Tsp2-Toxin3 | 1.9 | 0.029 |
| | Tsp3-Toxin3 | 1.9 | 0.051 |

TABLE 7-continued

In vitro cell proliferation assay results (HCC1954 and Jurkat cells)

| Cell Line | Sample | DAR | EC50 (nM) |
|---|---|---|---|
| | Tsp4-Toxin3 | 2.1 | 0.044 |
| | Tsp5-Toxin3 | 1.5 | 0.110 |
| | Tsp6-Toxin3 | 1.8 | 0.061 |
| | Tsp9-Toxin3 | 1.3 | 0.187 |
| | Tsp10-Toxin3 | 2.1 | 0.067 |
| | Tsp11-Toxin3 | 2.7 | 0.087 |
| | TVLCys1-Toxin3 | 1.1 | 0.118 |
| | Tsp10 Trastuzumab | | |
| | Free Toxin1 | | 0.2989 |
| Jurkat | Tsp2-Toxin3 | 1.9 | |
| | Tsp3-Toxin3 | 1.9 | |
| | Tsp4-Toxin3 | 2.1 | |
| | Tsp5-Toxin3 | 1.5 | |
| | Tsp6-Toxin3 | 1.8 | |
| | Tsp9-Toxin3 | 1.3 | |
| | Tsp10-Toxin3 | 2.1 | |
| | Tsp11-Toxin3 | 2.7 | |
| | TVLCys1-Toxin3 | 1.1 | |
| | Tsp10 Trastuzumab | | |
| | Free Toxin1 | | 0.1787 |

TABLE 8

In vitro cell proliferation assay results (N87 cells)

| Cell Line | Sample | DAR | EC50 (nM) |
|---|---|---|---|
| N87 | Tsp2-Toxin3 | 1.9 | 0.031 |
| | Tsp3-Toxin3 | 1.9 | 0.017 |
| | Tsp4-Toxin3 | 2.1 | 0.016 |
| | Tsp5-Toxin3 | 1.5 | 0.040 |
| | Tsp6-Toxin3 | 1.8 | 0.035 |
| | Tsp9-Toxin3 | 1.3 | 0.078 |
| | Tsp10-Toxin3 | 2.1 | 0.018 |
| | Tsp11-Toxin3 | 2.7 | 0.023 |
| | TVLCys1-Toxin3 | 1.1 | 0.048 |
| | Tsp10-Toxin1 | 1.9 | 0.068 |
| | Tsp10-Toxin4 | 1.9 | 0.1032 |

In vitro cell proliferation assays were also performed by treating CD30 antigen positive Karpas 299 cells with various Brentuximab ("B")-based ADCs and controls. Results are shown in FIGS. 54-58 and summarized below in Table 9.

TABLE 9

In vitro cell proliferation assay results (Karpas 299 cells)

| Cell Line | Sample | DAR | EC50 (nM) |
|---|---|---|---|
| Karpas 299 | Bsp10 | N/A | |
| | Bsp10-Toxin5 | 2.2 | 0.009 |
| | Bsp10-Toxin6 | 1.9 | 0.041 |
| | Bsp10-Toxin3 | 2.0 | 0.012 |
| | Bsp10-Toxin4 | 2.0 | 0.007 |
| | Bsp10-MCvcPABC-MMAE | 2.1 | 0.024 |
| | B-MCvcPABC-MMAE | 3.5 | 0.008 |
| | B (Brentuximab) | N/A | |

Example 19

Denaturing Page of Trastuzumab C-Terminal Light Chain Extension Variants

Trastuzumab light chain extension variants were purified on immobilized protein A and subjected to non-reducing denaturing or reducing (+DTT) denaturing polyacrylamide gel electrophoresis (PAGE). Results are shown in FIGS. 59-62.

Example 20

Conjugate Stability

ADC stability was assessed using a thermal stability assay. Individual aliquots of 1 mg/mL solutions of TSp10, TSp10-Toxin 3, TSp10-Toxin 1, TSp10-Toxin 4, TSp6-Toxin 3, TSp9-Toxin 3 in PBS, pH 7, were prepared. Non-denaturing SEC-UV analysis (described previously) was performed at an injection volume of 10 μL at time zero prior to incubation at 37° C. Aliquots of each sample were analyzed by non-denaturing SEC-UV after 191 hours of incubation, and after 330 hours of incubation. Percent monomer peak area of each species was adjusted against their respective zero time point measurement. Results are shown in FIG. 63, Panels A and B.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

---

What is claimed is:

1. An antibody, or an antigen-binding fragment thereof, comprising two heavy chains and two light chains, wherein each of the light chain polypeptides comprises a C-terminal amino acid extension comprising one or more cysteine residues,
wherein the C-terminal amino acid extension is from 6 to 50 amino acids or less in length, and comprises the amino acid sequence that is selected from the group consisting of ESSCDVKLVEKSFET (SEQ ID NO: 32), DCGFTS (SEQ ID NO: 33), DVITMDPKDNCSKDAN (SEQ ID NO: 34), DHVKPKETENTKQPSKSCHKPK (SEQ ID NO: 35), DVITMDPKDNC (SEQ ID NO: 98), ESSCDVKLV (SEQ ID NO: 101), and DHVKPKETENTKQPSKSC (SEQ ID NO: 102);
wherein the antibody or antigen-binding fragment is an IgG or antigen-binding fragment thereof, and
wherein the C-terminal amino acid extension does not specifically bind antigen.

2. The antibody or antigen-binding fragment of claim 1, wherein the C-terminal amino acid extension comprises one or more amino acid spacers that do not comprise a cysteine residue.

3. The antibody or antigen-binding fragment of claim 2, wherein the spacer comprises from 1 to 30 amino acids, or from 3 to 20 amino acids, or from 4 to 17 amino acids.

4. The antibody or antigen-binding fragment of claim 2, wherein the spacer comprises one or more glycine (G) residues and one or more serine (S) residues.

5. The antibody or antigen-binding fragment of claim 4, wherein the spacer comprises the sequence GGGS (SEQ ID NO: 1).

6. The antibody or antigen-binding fragment of claim 2, wherein the C-terminal amino acid extension comprises from 2 to 10 spacers and wherein (a) the spacers have the same amino acid sequence, or (b) have different amino acid sequences.

7. The antibody or antigen-binding fragment of claim 1, wherein the cysteine residue of the C-terminal amino acid is conjugated to a therapeutic agent or a labeling agent.

8. The antibody or antigen-binding fragment of claim 7, wherein the C-terminal amino acid extension comprises two or more cysteine residues, and wherein at least two of the two or more cysteine residues are conjugated to an agent independently selected from the group consisting of a therapeutic agent and a labeling agent.

9. The antibody or antigen-binding fragment of claim 1, wherein the antigen-binding fragment is selected from the group consisting of: a Fab, a F(ab')2, a Fab', an Fv, and an scFv.

10. A conjugate, comprising:
the antibody or antigen-binding fragment of claim 1; and
an agent conjugated to the antibody or antigen-binding fragment via a cysteine residue of the C-terminal amino acid extension.

11. The conjugate of claim 10, wherein the agent is conjugated to the cysteine residue via a linker.

12. The conjugate of claim 10, wherein the C-terminal amino acid extension comprises one or more amino acid spacers that do not comprise a cysteine residue.

13. The conjugate of claim 12, wherein the spacer comprises from 1 to 30 amino acids, or from 3 to 20 amino acids, or from 4 to 17 amino acids.

14. The conjugate of claim 12, wherein the spacer comprises one or more glycine (G) residues and one or more serine (S) residues.

15. The conjugate of claim 14, wherein the spacer comprises the sequence GGGS (SEQ ID NO: 1).

16. The conjugate of claim 12, wherein the C-terminal amino acid extension comprises from 2 to 10 spacers and wherein (a) the spacers have the same amino acid sequence, or (b) at least two of the spacers have different amino acid sequences.

17. The conjugate of claim 10, wherein the agent is a therapeutic agent or a labeling agent.

18. The conjugate of claim 10, wherein the agent is a cytotoxic agent.

19. The conjugate of claim 10, wherein the agent is an in vivo imaging agent.

20. The conjugate of claim 10, wherein the agent is conjugated to a cysteine residue of the C-terminal amino acid extension.

21. The conjugate of claim 10, wherein the C-terminal amino acid extension comprises two or more cysteine residues, and wherein at least two of the two or more cysteine residues are conjugated to an agent independently selected from a therapeutic agent and a labeling agent.

22. The conjugate of claim 10, wherein the antigen-binding fragment is selected from the group consisting of: a Fab, a F(ab')2, a Fab', an Fv, and an scFv.

23. A pharmaceutical composition comprising: the conjugate of claim 10; and
a pharmaceutically acceptable excipient.

24. A method comprising administering to a patient in need thereof a therapeutically effective amount of the conjugate of claim 10.

25. A method of making an antibody conjugate, comprising: conjugating an agent to the antibody or antigen-binding fragment of claim 1, wherein the agent is conjugated to a cysteine residue of the C-terminal amino acid extension.

26. The method of claim 25, wherein the method further comprises reducing the sulfhydryl group of the cysteine residue in the C-terminal amino acid extension prior to conjugating the agent to the antibody or antigen-binding fragment.

27. The method of claim 26, wherein the reducing comprises (a) reducing one or more cysteine residues in the C-terminal amino acid extension over a cysteine residue not in the C-terminal amino acid extension, or (b) reducing one or more cysteine residues in the C-terminal amino acid extension and not reducing any cysteine residues not in the C-terminal amino acid extension.

28. The method of claim 25, wherein the agent is a therapeutic agent or a labeling agent.

29. The antibody or antigen-binding fragment of claim 2, wherein the C-terminal amino acid extension comprises from 2 to 10 spacers and wherein at least two of the spacers comprise the sequence GGGS (SEQ ID NO:1).

30. The conjugate of claim 12, wherein the C-terminal amino acid extension comprises from 2 to 10 spacers and wherein at least two of the spacers comprise the sequence GGGS (SEQ ID NO:1).

31. The conjugate of claim 18, wherein the cytotoxic agent is an auristatin or analog thereof, or a hemiasterlin or analog thereof.

32. The antibody or antigen-binding fragment of claim 1, wherein the C-terminal amino acid extension is 25 amino acids or less in length.

33. The antibody or antigen-binding fragment of claim 1, wherein the antibody or antigen-binding fragment thereof is bispecific.

34. The conjugate of claim 10, wherein the C-terminal amino acid extension is 25 amino acids or less in length.

35. The conjugate of claim 10, wherein the antibody or antigen-binding fragment thereof is bispecific.

36. The antibody or antigen-binding fragment of claim 1, wherein the human amino acid sequence is an amino acid sequence of a human TCR hinge region, or a portion thereof.

37. The antibody or antigen-binding fragment of claim 1, wherein the IgG is a human IgG1, IgG2 or IgG4.

38. The antibody or antigen-binding fragment of claim 1, wherein the human TCR hinge region is a human TCR α, δ or γ hinge region.

39. The antibody or antigen-binding fragment of claim 36, wherein the human TCR hinge region is a human TCR α, δ or γ hinge region.

* * * * *

SEQUENCE LISTING

```
<160> NUMBER OF SEQ ID NOS: 132

<210> SEQ ID NO 1
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 1

Gly Gly Gly Ser
1

<210> SEQ ID NO 2
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 2

Ala Lys Thr Thr Pro Lys Leu Glu Glu Gly Glu Phe Ser Glu Ala Arg
1               5                   10                  15

<210> SEQ ID NO 3
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 3

Ala Lys Thr Thr Pro Lys Leu Glu Glu Gly Glu Phe Ser Glu Ala Arg
1               5                   10                  15

Val
```

<210> SEQ ID NO 4
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 4

Ala Lys Thr Thr Pro Lys Leu Gly Gly
1               5

<210> SEQ ID NO 5
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 5

Ser Ala Lys Thr Thr Pro Lys Leu Gly Gly
1               5                   10

<210> SEQ ID NO 6
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 6

Ala Lys Thr Thr Pro Lys Leu Glu Glu Gly Glu Phe Ser Glu Ala Arg
1               5                   10                  15

Val

<210> SEQ ID NO 7
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 7

Ser Ala Lys Thr Thr Pro
1               5

<210> SEQ ID NO 8
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 8

Ser Ala Lys Thr Thr Pro Lys Leu Gly Gly
1               5                   10

<210> SEQ ID NO 9
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 9

Arg Ala Asp Ala Ala Pro

```
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 10

Arg Ala Asp Ala Ala Pro Thr Val Ser
1               5

<210> SEQ ID NO 11
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 11

Arg Ala Asp Ala Ala Ala Ala Gly Gly Pro Gly Ser
1               5                   10

<210> SEQ ID NO 12
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 12

Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 13
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 13

Ser Ala Lys Thr Thr Pro
1               5

<210> SEQ ID NO 14
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 14

Ser Ala Lys Thr Thr Pro Lys Leu Gly Gly
1               5                   10

<210> SEQ ID NO 15
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 15
```

```
Ser Ala Lys Thr Thr Pro Lys Leu Glu Glu Gly Glu Phe Ser Glu Ala
1               5                   10                  15

Arg Val

<210> SEQ ID NO 16
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 16

Ala Asp Ala Ala Pro
1               5

<210> SEQ ID NO 17
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 17

Ala Asp Ala Ala Pro Thr Val Ser Ile Phe Pro Pro
1               5                   10

<210> SEQ ID NO 18
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 18

Thr Val Ala Ala Pro
1               5

<210> SEQ ID NO 19
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 19

Thr Val Ala Ala Pro Ser Val Phe Ile Phe Pro Pro
1               5                   10

<210> SEQ ID NO 20
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 20

Gln Pro Lys Ala Ala Pro
1               5

<210> SEQ ID NO 21
<211> LENGTH: 13
<212> TYPE: PRT
<213> ORGANISM: Artificial sequence
<220> FEATURE:
<223> OTHER INFORMATION: Synthetic polypeptide
```

```
<400> SEQUENCE: 21

Gln Pro Lys Ala Ala Pro Ser Val Thr Leu Phe Pro Pro
1               5                   10

<210> SEQ ID NO 22
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 22

Ala Lys Thr Thr Pro Pro
1               5

<210> SEQ ID NO 23
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 23

Ala Lys Thr Thr Pro Pro Ser Val Thr Pro Leu Ala Pro
1               5                   10

<210> SEQ ID NO 24
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 24

Ala Lys Thr Thr Ala Pro
1               5

<210> SEQ ID NO 25
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 25

Ala Lys Thr Thr Ala Pro Ser Val Tyr Pro Leu Ala Pro
1               5                   10

<210> SEQ ID NO 26
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 26

Ala Ser Thr Lys Gly Pro
1               5

<210> SEQ ID NO 27
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 27
```

```
Ala Ser Thr Lys Gly Pro Ser Val Phe Pro Leu Ala Pro
1               5                   10

<210> SEQ ID NO 28
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 29

Gly Glu Asn Lys Val Glu Tyr Ala Pro Ala Leu Met Ala Leu Ser
1               5                   10                  15

<210> SEQ ID NO 30
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 30

Gly Pro Ala Lys Glu Leu Thr Pro Leu Lys Glu Ala Lys Val Ser
1               5                   10                  15

<210> SEQ ID NO 31
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 31

Gly His Glu Ala Ala Ala Val Met Gln Val Gln Tyr Pro Ala Ser
1               5                   10                  15

<210> SEQ ID NO 32
<211> LENGTH: 15
<212> TYPE: PRT
<213> ORGANISM: Homo sapiens

<400> SEQUENCE: 32

Glu Ser Ser Cys Asp Val Lys Leu Val Glu Lys Ser Phe Glu Thr
1               5                   10                  15

<210> SEQ ID NO 33
<211> LENGTH: 6
<212> TYPE: PRT
<213> ORGANISM: Homo sapiens

<400> SEQUENCE: 33

Asp Cys Gly Phe Thr Ser
1               5
```

<210> SEQ ID NO 34
<211> LENGTH: 16
<212> TYPE: PRT
<213> ORGANISM: Homo sapiens

<400> SEQUENCE: 34

Asp Val Ile Thr Met Asp Pro Lys Asp Asn Cys Ser Lys Asp Ala Asn
1               5                   10                  15

<210> SEQ ID NO 35
<211> LENGTH: 22
<212> TYPE: PRT
<213> ORGANISM: Homo sapiens

<400> SEQUENCE: 35

Asp His Val Lys Pro Lys Glu Thr Glu Asn Thr Lys Gln Pro Ser Lys
1               5                   10                  15

Ser Cys His Lys Pro Lys
            20

<210> SEQ ID NO 36
<211> LENGTH: 15
<212> TYPE: PRT
<213> ORGANISM: Homo sapiens

<400> SEQUENCE: 36

Glu Pro Lys Ser Cys Asp Lys Thr His Thr Cys Pro Pro Cys Pro
1               5                   10                  15

<210> SEQ ID NO 37
<211> LENGTH: 12
<212> TYPE: PRT
<213> ORGANISM: Homo sapiens

<400> SEQUENCE: 37

Glu Arg Lys Cys Cys Val Glu Cys Pro Pro Cys Pro
1               5                   10

<210> SEQ ID NO 38
<211> LENGTH: 17
<212> TYPE: PRT
<213> ORGANISM: Homo sapiens

<400> SEQUENCE: 38

Glu Leu Lys Thr Pro Leu Gly Asp Thr Thr His Thr Cys Pro Arg Cys
1               5                   10                  15

Pro

<210> SEQ ID NO 39
<211> LENGTH: 15
<212> TYPE: PRT
<213> ORGANISM: Homo sapiens

<400> SEQUENCE: 39

Glu Pro Lys Ser Cys Asp Thr Pro Pro Pro Cys Pro Arg Cys Pro
1               5                   10                  15

<210> SEQ ID NO 40
<211> LENGTH: 12
<212> TYPE: PRT
<213> ORGANISM: Homo sapiens

<400> SEQUENCE: 40

Glu Ser Lys Tyr Gly Pro Pro Cys Pro Ser Cys Pro

<210> SEQ ID NO 41
<211> LENGTH: 6
<212> TYPE: PRT
<213> ORGANISM: Homo sapiens

<400> SEQUENCE: 41

Val Pro Pro Pro Pro Pro
1               5

<210> SEQ ID NO 42
<211> LENGTH: 58
<212> TYPE: PRT
<213> ORGANISM: Artificial sequence
<220> FEATURE:
<223> OTHER INFORMATION: Synthetic polypeptide

<400> SEQUENCE: 42

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro
    50                  55

<210> SEQ ID NO 43
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 43

Glu Ser Ser
1

<210> SEQ ID NO 44
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 44

Asp Val Lys Leu Val Glu Lys Ser Phe Glu Thr
1               5                   10

<210> SEQ ID NO 45
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 45

Gly Phe Thr Ser
1

<210> SEQ ID NO 46
<211> LENGTH: 10
<212> TYPE: PRT
<213> ORGANISM: Artificial sequence

```
<220> FEATURE:
<223> OTHER INFORMATION: Synthetic polypeptide

<400> SEQUENCE: 46

Asp Val Ile Thr Met Asp Pro Lys Asp Asn
1               5                   10

<210> SEQ ID NO 47
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 47

Ser Lys Asp Ala Asn
1               5

<210> SEQ ID NO 48
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 48

Asp His Val Lys Pro Lys Glu Thr Glu Asn Thr Lys Gln Pro Ser Lys
1               5                   10                  15

Ser

<210> SEQ ID NO 49
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 49

His Lys Pro Lys
1

<210> SEQ ID NO 50
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 50

Glu Pro Lys Ser
1

<210> SEQ ID NO 51
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 51

Asp Lys Thr His Thr
1               5

<210> SEQ ID NO 52
<211> LENGTH: 3
<212> TYPE: PRT
```

```
<213> ORGANISM: Artificial sequence
<220> FEATURE:
<223> OTHER INFORMATION: Synthetic polypeptide

<400> SEQUENCE: 52

Glu Arg Lys
1

<210> SEQ ID NO 53
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 53

Glu Leu Lys Thr Pro Leu Gly Asp Thr Thr His Thr
1               5                   10

<210> SEQ ID NO 54
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 54

Asp Thr Pro Pro Pro
1               5

<210> SEQ ID NO 55
<211> LENGTH: 2
<212> TYPE: PRT
<213> ORGANISM: Artificial sequence
<220> FEATURE:
<223> OTHER INFORMATION: Synthetic polypeptide

<400> SEQUENCE: 55

Val Glu
1

<210> SEQ ID NO 56
<211> LENGTH: 2
<212> TYPE: PRT
<213> ORGANISM: Artificial sequence
<220> FEATURE:
<223> OTHER INFORMATION: Synthetic polypeptide

<400> SEQUENCE: 56

Pro Arg
1

<210> SEQ ID NO 57
<211> LENGTH: 2
<212> TYPE: PRT
<213> ORGANISM: Artificial sequence
<220> FEATURE:
<223> OTHER INFORMATION: Synthetic polypeptide

<400> SEQUENCE: 57

Pro Pro
1

<210> SEQ ID NO 58
<211> LENGTH: 2
<212> TYPE: PRT
<213> ORGANISM: Artificial sequence
```

```
<220> FEATURE:
<223> OTHER INFORMATION: Synthetic polypeptide

<400> SEQUENCE: 58

Pro Ser
1

<210> SEQ ID NO 59
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 59

Glu Ser Lys Tyr Gly Pro Pro
1               5

<210> SEQ ID NO 60
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 60

Gly Gly Gly Ser Cys
1               5

<210> SEQ ID NO 61
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 61

Gly Gly Gly Ser Cys Cys
1               5

<210> SEQ ID NO 62
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 62

Gly Gly Gly Ser Gly Gly Gly Ser Cys
1               5

<210> SEQ ID NO 63
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)
```

<400> SEQUENCE: 63

Gly Gly Gly Ser Cys Gly Gly Gly Ser Cys
1               5                   10

<210> SEQ ID NO 64
<211> LENGTH: 20
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 64

Gly Gly Gly Ser Cys Gly Gly Gly Ser Cys Gly Gly Gly Ser Cys Gly
1               5                   10                  15

Gly Gly Ser Cys
            20

<210> SEQ ID NO 65
<211> LENGTH: 18
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 65

Gly Gly Gly Ser Cys Gly Gly Gly Ser Gly Gly Gly Ser Gly Gly Gly
1               5                   10                  15

Ser Cys

<210> SEQ ID NO 66
<211> LENGTH: 14
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 66

Gly Gly Gly Ser Gly Gly Gly Ser Cys Gly Gly Gly Ser Cys
1               5                   10

<210> SEQ ID NO 67
<211> LENGTH: 14
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 67

Gly Gly Gly Ser Cys Gly Gly Gly Ser Gly Gly Gly Ser Cys
1               5                   10

<210> SEQ ID NO 68
<211> LENGTH: 17
<212> TYPE: PRT

<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 68

Ala Lys Thr Thr Pro Lys Leu Glu Glu Gly Glu Phe Ser Glu Ala Arg
1               5                   10                  15

Cys

<210> SEQ ID NO 69
<211> LENGTH: 33
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 69

Ala Lys Thr Thr Pro Lys Leu Glu Glu Gly Glu Phe Ser Glu Ala Arg
1               5                   10                  15

Ala Lys Thr Thr Pro Lys Leu Glu Glu Gly Glu Phe Ser Glu Ala Arg
            20                  25                  30

Cys

<210> SEQ ID NO 70
<211> LENGTH: 34
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 70

Ala Lys Thr Thr Pro Lys Leu Glu Glu Gly Glu Phe Ser Glu Ala Arg
1               5                   10                  15

Cys Ala Lys Thr Thr Pro Lys Leu Glu Glu Gly Glu Phe Ser Glu Ala
            20                  25                  30

Arg Cys

<210> SEQ ID NO 71
<211> LENGTH: 68
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 71

Ala Lys Thr Thr Pro Lys Leu Glu Glu Gly Glu Phe Ser Glu Ala Arg
1               5                   10                  15

Cys Ala Lys Thr Thr Pro Lys Leu Glu Glu Gly Glu Phe Ser Glu Ala
            20                  25                  30

Arg Cys Ala Lys Thr Thr Pro Lys Leu Glu Glu Gly Glu Phe Ser Glu
        35                  40                  45

Ala Arg Cys Ala Lys Thr Thr Pro Lys Leu Glu Glu Gly Glu Phe Ser

```
                 50                  55                  60

Glu Ala Arg Cys
 65

<210> SEQ ID NO 72
<211> LENGTH: 66
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 72

Ala Lys Thr Thr Pro Lys Leu Glu Glu Gly Glu Phe Ser Glu Ala Arg
 1               5                  10                  15

Cys Ala Lys Thr Thr Pro Lys Leu Glu Glu Gly Glu Phe Ser Glu Ala
                20                  25                  30

Arg Ala Lys Thr Thr Pro Lys Leu Glu Glu Gly Glu Phe Ser Glu Ala
            35                  40                  45

Arg Ala Lys Thr Thr Pro Lys Leu Glu Glu Gly Glu Phe Ser Glu Ala
        50                  55                  60

Arg Cys
 65

<210> SEQ ID NO 73
<211> LENGTH: 50
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 73

Ala Lys Thr Thr Pro Lys Leu Glu Glu Gly Glu Phe Ser Glu Ala Arg
 1               5                  10                  15

Ala Lys Thr Thr Pro Lys Leu Glu Glu Gly Glu Phe Ser Glu Ala Arg
                20                  25                  30

Cys Ala Lys Thr Thr Pro Lys Leu Glu Glu Gly Glu Phe Ser Glu Ala
            35                  40                  45

Arg Cys
    50

<210> SEQ ID NO 74
<211> LENGTH: 50
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 74

Ala Lys Thr Thr Pro Lys Leu Glu Glu Gly Glu Phe Ser Glu Ala Arg
 1               5                  10                  15

Cys Ala Lys Thr Thr Pro Lys Leu Glu Glu Gly Glu Phe Ser Glu Ala
                20                  25                  30

Arg Ala Lys Thr Thr Pro Lys Leu Glu Glu Gly Glu Phe Ser Glu Ala
            35                  40                  45
```

-continued

Arg Cys
    50

<210> SEQ ID NO 75
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 75
attagctagc accaagggcc catcggtctt c                                    31

<210> SEQ ID NO 76
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 76
gatatggatc ctcatttacc cggagacagg ga                                   32

<210> SEQ ID NO 77
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 77
tatgctagcg tcgtacggtg gctgcaccat ctgtcttcat c                         41

<210> SEQ ID NO 78
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 78
gatggatccc taacactctc ccctgttgaa gc                                   32

<210> SEQ ID NO 79
<211> LENGTH: 147
<212> TYPE: PRT
<213> ORGANISM: Artificial Sequence
<220> FEATURE:
<223> OTHER INFORMATION: Herceptin VH amino acid sequence

<400> SEQUENCE: 79

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

```
Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
            115                 120                 125

Trp Gly Gln Gly Thr Leu Val Thr Val Ser Ser Ala Ser Thr Lys Gly
    130                 135                 140

Pro Ser Val
145

<210> SEQ ID NO 80
<211> LENGTH: 464
<212> TYPE: DNA
<213> ORGANISM: Artificial Sequence
<220> FEATURE:
<223> OTHER INFORMATION: Herceptin VH nucleotide sequence

<400> SEQUENCE: 80
agtcagtcgg aattcgccac catggagttt gggctgagct gggttttcct tgttgctatt      60
ttaaaaggtg tccagtgtga ggtgcagctg gtggagagcg gcggcggcct ggtgcagccc     120
ggcggcagcc tgagactgag ctgcgccgcc agcggcttca acatcaagga cacctacatc     180
cactgggtga cagggcccc tggcaagggc ctggagtggg tggccagaat ctaccccacc      240
aacggctaca ccagatacgc cgacagcgtg aagggcagat tcaccatcag cgccgacacc     300
agcaagaaca ccgcctacct gcagatgaac agcctgagag ccgaggacac cgccgtgtac     360
tactgcagca gatggggcgg cgacggcttc tacgccatgg actactgggg ccagggcacc     420
ctggtgaccg tgagcagcgc tagcaccaag ggcccatcgg tctt                      464

<210> SEQ ID NO 81
<211> LENGTH: 137
<212> TYPE: PRT
<213> ORGANISM: Artificial Sequence
<220> FEATURE:
<223> OTHER INFORMATION: Herceptin Vk amino acid sequence

<400> SEQUENCE: 81

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
    50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Arg Thr Val Ala Ala Pro Ser Val
    130                 135

<210> SEQ ID NO 82
<211> LENGTH: 433
```

```
<212> TYPE: DNA
<213> ORGANISM: Artificial Sequence
<220> FEATURE:
<223> OTHER INFORMATION: Herceptin Vk nucleotide sequence

<400> SEQUENCE: 82
agtcagtcgg aattcgctac catggacatg agggtccccg ctcagctcct ggggctcctg      60
ctactctggc tccgaggtgc cagatgtgac atccagatga cccagagccc agcagcctg     120 agcgccagcg tgggcgacag agtgaccatc acctgcagag ccagccagga cgtgaacacc    180
gccgtggcct ggtaccagca gaagcccggc aaggctccca agctgctgat ctacagcgcc    240
agcttcctgt acagcggcgt gcccagcaga ttcagcggca gcagaagcgg caccgacttc    300
accctgacca tcagcagcct gcagcccgag gacttcgcca catactactg ccagcagcac    360
tacaccaccc ctcccacctt cggccagggc accaaggtgg agatcaagcg tacggtggct    420
gcaccatctg tct                                                      433

<210> SEQ ID NO 83
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 83
acgtggatcc tcaacagctt ccccctccac actctcccct gttgaagc                 48

<210> SEQ ID NO 84
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 84
acgtggatcc tcaacagctt ccccctccgc agcttcctcc tccacactct ccctgttga     60 agc                                                                  63

<210> SEQ ID NO 85
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 85
acgtggatcc tcaacagctt ccccctccgc agcttcctcc tccgcaagat cctcctccac    60
actctcccct gttgaagc                                                  78

<210> SEQ ID NO 86
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 86
acagcttccc cctccgcagc ttcctcctcc gcaagatcct cctccacact ctcccctgtt    60
gaagc                                                                65

<210> SEQ ID NO 87
```

```
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 87
acgtggatcc tcagcagctt cctcctccac agcttccccc tccgcagct          49

<210> SEQ ID NO 88
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 88
tgcgctaaga ttgtcagttt cca                                       23

<210> SEQ ID NO 89
<211> LENGTH: 22
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 89

Gly Gly Gly Ser Cys Ala Lys Thr Thr Pro Lys Leu Glu Glu Gly Glu
1               5                   10                  15

Phe Ser Glu Ala Arg Cys
            20

<210> SEQ ID NO 90
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 90

Gly Gly Gly Ser Cys Ala Lys Thr Thr Pro Lys Leu Glu Glu Gly Glu
1               5                   10                  15

Phe Ser Glu Ala Arg Cys Ala Lys Thr Thr Pro Lys Leu Glu Glu Gly
            20                  25                  30

Glu Phe Ser Glu Ala Arg Cys
        35

<210> SEQ ID NO 91
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 91

Asp Val Lys Leu Val
1               5

<210> SEQ ID NO 92
<211> LENGTH: 11
```

```
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 92

Glu Pro Lys Ser Cys Asp Lys Thr His Thr Cys
1               5                   10

<210> SEQ ID NO 93
<211> LENGTH: 14
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 93

Glu Pro Lys Ser Cys Asp Lys Thr His Thr Cys Pro Pro Cys
1               5                   10

<210> SEQ ID NO 94
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 94

Glu Pro Lys Ser Cys
1               5

<210> SEQ ID NO 95
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 95

Glu Ser Lys Tyr Gly Pro Pro Cys
1               5

<210> SEQ ID NO 96
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 96

Glu Arg Lys Cys Cys Val Glu Cys Pro Pro Cys
1               5                   10

<210> SEQ ID NO 97
```

```
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 97

Glu Arg Lys Cys
1

<210> SEQ ID NO 98
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 98

Asp Val Ile Thr Met Asp Pro Lys Asp Asn Cys
1               5                   10

<210> SEQ ID NO 99
<211> LENGTH: 22
<212> TYPE: PRT
<213> ORGANISM: Homo sapiens
<220> FEATURE:
<221> NAME/KEY: NON_TER
<222> LOCATION: (1)..(1)

<400> SEQUENCE: 99

Asp His Val Lys Pro Lys Glu Thr Glu Asn Thr Lys Gln Pro Ser Lys
1               5                   10                  15

Ser Cys His Lys Pro Lys
            20

<210> SEQ ID NO 100
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 100

Glu Ser Ser Cys
1

<210> SEQ ID NO 101
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 101

Glu Ser Ser Cys Asp Val Lys Leu Val
1               5
```

<210> SEQ ID NO 102
<211> LENGTH: 18
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 102

Asp His Val Lys Pro Lys Glu Thr Glu Asn Thr Lys Gln Pro Ser Lys
1               5                   10                  15

Ser Cys

<210> SEQ ID NO 103
<211> LENGTH: 16
<212> TYPE: PRT
<213> ORGANISM: Homo sapiens
<220> FEATURE:
<221> NAME/KEY: NON_TER
<222> LOCATION: (1)..(1)

<400> SEQUENCE: 103

Asp Val Ile Thr Met Asp Pro Lys Asp Asn Cys Ser Lys Asp Ala Asn
1               5                   10                  15

<210> SEQ ID NO 104
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 104

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Glu Pro Lys Ser Cys
            100                 105                 110

Asp Lys Thr His Thr Cys
        115

<210> SEQ ID NO 105
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 105

Arg Thr Val Ala Ala Pro Ser Val Phe Ile Phe Pro Pro Ser Asp Glu
1               5                   10                  15

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Glu Pro Lys Ser Cys
            100                 105                 110

Asp Lys Thr His Thr Cys Pro Pro Cys
            115                 120

<210> SEQ ID NO 106
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 106

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Glu Pro Lys Ser Cys
            100                 105                 110

<210> SEQ ID NO 107
<211> LENGTH: 115
<212> TYPE: PRT
<213> ORGANISM: Artificial sequence
<220> FEATURE:
<223> OTHER INFORMATION: Synthetic polypeptide

<400> SEQUENCE: 107

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95
```

Pro Val Thr Lys Ser Phe Asn Arg Gly Glu Cys Glu Ser Lys Tyr Gly
                100                 105                 110

Pro Pro Cys
        115

<210> SEQ ID NO 108
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 108

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Glu Arg Lys Cys Cys
                100                 105                 110

Val Glu Cys Pro Pro Cys
            115

<210> SEQ ID NO 109
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 109

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Glu Arg Lys Cys
                100                 105                 110

<210> SEQ ID NO 110
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 110

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Asp Val Ile Thr Met
            100                 105                 110

Asp Pro Lys Asp Asn Cys
        115

<210> SEQ ID NO 111
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 111

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Asp His Val Lys Pro
            100                 105                 110

Lys Glu Thr Glu Asn Thr Lys Gln Pro Ser Lys Ser Cys His Lys Pro
        115                 120                 125

Lys

<210> SEQ ID NO 112
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 112

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

```
Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys Glu Ser Cys
            100                 105                 110
```

<210> SEQ ID NO 113
<211> LENGTH: 116
<212> TYPE: PRT
<213> ORGANISM: Artificial sequence
<220> FEATURE:
<223> OTHER INFORMATION: Synthetic polypeptide

<400> SEQUENCE: 113

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys Glu Ser Ser Cys Asp
            100                 105                 110

Val Lys Leu Val
         115
```

<210> SEQ ID NO 114
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 114

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys Asp His Val Lys Pro
            100                 105                 110
```

Lys Glu Thr Glu Asn Thr Lys Gln Pro Ser Lys Ser Cys
            115                 120                 125

<210> SEQ ID NO 115
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 115

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Asp Val Ile Thr Met
            100                 105                 110

Asp Pro Lys Asp Asn Cys Ser Lys Asp Ala Asn
            115                 120

<210> SEQ ID NO 116
<211> LENGTH: 410
<212> TYPE: DNA
<213> ORGANISM: Artificial Sequence
<220> FEATURE:
<223> OTHER INFORMATION: Herceptin VL and hIgk constant region (Km3
      allotype) + a EPKSCDKTHTC tail (sequence from human IgG1 hinge)

<400> SEQUENCE: 116
ggccagggca ccaaggtgga gatcaagcgt acggtggctg caccatctgt cttcatcttc      60
ccgccatctg atgagcagtt gaaatctgga actgcctctg ttgtgtgcct gctgaataac     120
ttctatccca gagaggccaa agtacagtgg aaggtggata acgccctcca atcgggtaac     180
tcccaggaga gtgtcacaga gcaggacagc aaggacagca cctacagcct cagcagcacc     240
ctgacgctga gcaaagcaga ctacgagaaa cacaaagtct acgcctgcga agtcacccat     300
cagggcctga gctcgcccgt cacaaagagc ttcaacaggg gagagtgtga gccaaaatcc     360
tgtgacaaga ctcacacgtg ttgaggatcc ccgacctcg acctctggct     410

<210> SEQ ID NO 117
<211> LENGTH: 419
<212> TYPE: DNA
<213> ORGANISM: Artificial Sequence
<220> FEATURE:
<223> OTHER INFORMATION: Herceptin VL and hIgk constant region (Km3
      allotype) + a EPKSCDKTHTCPPC tail (sequence from human IgG1 hinge)

<400> SEQUENCE: 117
ggccagggca ccaaggtgga gatcaagcgt acggtggctg caccatctgt cttcatcttc      60
ccgccatctg atgagcagtt gaaatctgga actgcctctg ttgtgtgcct gctgaataac     120
ttctatccca gagaggccaa agtacagtgg aaggtggata acgccctcca atcgggtaac     180

```
tcccaggaga gtgtcacaga gcaggacagc aaggacagca cctacagcct cagcagcacc      240
ctgacgctga gcaaagcaga ctacgagaaa cacaaagtct acgcctgcga agtcacccat      300
cagggcctga gctcgcccgt cacaaagagc ttcaacaggg gagagtgtga gcctaagtca      360
tgcgacaaga cccacacctg tccaccttgt tgaggatccc cgacctcga cctctggct       419

<210> SEQ ID NO 118
<211> LENGTH: 392
<212> TYPE: DNA
<213> ORGANISM: Artificial Sequence
<220> FEATURE:
<223> OTHER INFORMATION: Herceptin VL and hIgk constant region (Km3
      allotype) + a EPKSC tail (sequence from human IgG1 hinge)

<400> SEQUENCE: 118
ggccagggca ccaaggtgga gatcaagcgt acggtggctg caccatctgt cttcatcttc       60
ccgccatctg atgagcagtt gaaatctgga actgcctctg ttgtgtgcct gctgaataac      120
ttctatccca gagaggccaa agtacagtgg aaggtggata acgccctcca atcgggtaac      180
tcccaggaga gtgtcacaga gcaggacagc aaggacagca cctacagcct cagcagcacc      240
ctgacgctga gcaaagcaga ctacgagaaa cacaaagtct acgcctgcga agtcacccat      300
cagggcctga gctcgcccgt cacaaagagc ttcaacaggg gagagtgtga accaaagtcc      360
tgttgaggat cccccgacct cgacctctgg ct                                    392

<210> SEQ ID NO 119
<211> LENGTH: 401
<212> TYPE: DNA
<213> ORGANISM: Artificial Sequence
<220> FEATURE:
<223> OTHER INFORMATION: Herceptin VL and hIgk constant region (Km3
      allotype) + a ESKYGPPC tail (sequence from human IgG4 hinge)

<400> SEQUENCE: 119
ggccagggca ccaaggtgga gatcaagcgt acggtggctg caccatctgt cttcatcttc       60
ccgccatctg atgagcagtt gaaatctgga actgcctctg ttgtgtgcct gctgaataac      120
ttctatccca gagaggccaa agtacagtgg aaggtggata acgccctcca atcgggtaac      180
tcccaggaga gtgtcacaga gcaggacagc aaggacagca cctacagcct cagcagcacc      240
ctgacgctga gcaaagcaga ctacgagaaa cacaaagtct acgcctgcga agtcacccat      300
cagggcctga gctcgcccgt cacaaagagc ttcaacaggg gagagtgtga gtctaaatat      360 ggaccccgt gctgaggatc ccccgacctc gacctctggc t                          401

<210> SEQ ID NO 120
<211> LENGTH: 410
<212> TYPE: DNA
<213> ORGANISM: Artificial Sequence
<220> FEATURE:
<223> OTHER INFORMATION: Herceptin VL and hIgk constant region (Km3
      allotype) + a ERKCCVECPPC tail (sequence from human IgG2 hinge)

<400> SEQUENCE: 120
ggccagggca ccaaggtgga gatcaagcgt acggtggctg caccatctgt cttcatcttc       60
ccgccatctg atgagcagtt gaaatctgga actgcctctg ttgtgtgcct gctgaataac      120
ttctatccca gagaggccaa agtacagtgg aaggtggata acgccctcca atcgggtaac      180
tcccaggaga gtgtcacaga gcaggacagc aaggacagca cctacagcct cagcagcacc      240
ctgacgctga gcaaagcaga ctacgagaaa cacaaagtct acgcctgcga agtcacccat      300
```

```
cagggcctga gctcgcccgt cacaaagagc ttcaacaggg gagagtgtga gagaaagtgt    360
tgcgtagagt gtcctccctg ctgaggatcc cccgacctcg acctctggct               410
```

<210> SEQ ID NO 121
<211> LENGTH: 389
<212> TYPE: DNA
<213> ORGANISM: Artificial Sequence
<220> FEATURE:
<223> OTHER INFORMATION: Herceptin VL and hIgk constant region (Km3
      allotype) + a ERKC tail (sequence from human IgG2 hinge)

<400> SEQUENCE: 121

```
ggccagggca ccaaggtgga gatcaagcgt acggtggctg caccatctgt cttcatcttc    60
ccgccatctg atgagcagtt gaaatctgga actgcctctg ttgtgtgcct gctgaataac   120
ttctatccca gagaggccaa agtacagtgg aaggtggata acgccctcca atcgggtaac   180
tcccaggaga gtgtcacaga gcaggacagc aaggacagca cctacagcct cagcagcacc   240
ctgacgctga gcaaagcaga ctacgagaaa cacaaagtct acgcctgcga agtcacccat   300
cagggcctga gctcgcccgt cacaaagagc ttcaacaggg gagagtgtga gcggaaatgc   360
tgaggatccc ccgacctcga cctctggct                                     389
```

<210> SEQ ID NO 122
<211> LENGTH: 410
<212> TYPE: DNA
<213> ORGANISM: Artificial Sequence
<220> FEATURE:
<223> OTHER INFORMATION: Herceptin VL and hIgk constant region (Km3
      allotype) + a DVITMDPKDNC tail (sequence from human TCRg hinge)

<400> SEQUENCE: 122

```
ggccagggca ccaaggtgga gatcaagcgt acggtggctg caccatctgt cttcatcttc    60
ccgccatctg atgagcagtt gaaatctgga actgcctctg ttgtgtgcct gctgaataac   120
ttctatccca gagaggccaa agtacagtgg aaggtggata acgccctcca atcgggtaac   180
tcccaggaga gtgtcacaga gcaggacagc aaggacagca cctacagcct cagcagcacc   240
ctgacgctga gcaaagcaga ctacgagaaa cacaaagtct acgcctgcga agtcacccat   300
cagggcctga gctcgcccgt cacaaagagc ttcaacaggg gagagtgtga cgttataacc   360
atggacccga aagacaattg ctgaggatcc cccgacctcg acctctggct              410
```

<210> SEQ ID NO 123
<211> LENGTH: 443
<212> TYPE: DNA
<213> ORGANISM: Artificial Sequence
<220> FEATURE:
<223> OTHER INFORMATION: Herceptin VL and hIgk constant region (Km3
      allotype) + a DHVKPKETENTKQPSKSCHKPK tail (sequence from human
      TCRd hinge)

<400> SEQUENCE: 123

```
ggccagggca ccaaggtgga gatcaagcgt acggtggctg caccatctgt cttcatcttc    60
ccgccatctg atgagcagtt gaaatctgga actgcctctg ttgtgtgcct gctgaataac   120
ttctatccca gagaggccaa agtacagtgg aaggtggata acgccctcca atcgggtaac   180
tcccaggaga gtgtcacaga gcaggacagc aaggacagca cctacagcct cagcagcacc   240
ctgacgctga gcaaagcaga ctacgagaaa cacaaagtct acgcctgcga agtcacccat   300
cagggcctga gctcgcccgt cacaaagagc ttcaacaggg gagagtgtga tcacgtgaag   360
```

```
cccaaggaga cggagaatac caaacaacct tccaaatcat gtcacaaacc aaaatgagga      420
tcccccgacc tcgacctctg gct                                             443
```

<210> SEQ ID NO 124
<211> LENGTH: 389
<212> TYPE: DNA
<213> ORGANISM: Artificial Sequence
<220> FEATURE:
<223> OTHER INFORMATION: Herceptin VL and hIgk constant region (Km3
      allotype) + a ESSC tail (sequence from human TCRa hinge)

<400> SEQUENCE: 124

```
ggccagggca ccaaggtgga gatcaagcgt acggtggctg caccatctgt cttcatcttc      60
ccgccatctg atgagcagtt gaaatctgga actgcctctg ttgtgtgcct gctgaataac     120
ttctatccca gagaggccaa agtacagtgg aaggtggata cgccctcca atcgggtaac     180 tcccaggaga gtgtcacaga gcaggacagc aaggacagca cctacagcct cagcagcacc     240
ctgacgctga gcaaagcaga ctacgagaaa cacaaagtct acgcctgcga agtcacccat     300
cagggcctga gctcgcccgt cacaaagagc ttcaacaggg gagagtgtga agcagctgt      360 tgaggatccc ccgacctcga cctctggct                                       389
```

<210> SEQ ID NO 125
<211> LENGTH: 404
<212> TYPE: DNA
<213> ORGANISM: Artificial Sequence
<220> FEATURE:
<223> OTHER INFORMATION: Herceptin VL and hIgk constant region (Km3
      allotype) + a ESSCDVKLV tail (sequence from human TCRa hinge)

<400> SEQUENCE: 125

```
ggccagggca ccaaggtgga gatcaagcgt acggtggctg caccatctgt cttcatcttc      60
ccgccatctg atgagcagtt gaaatctgga actgcctctg ttgtgtgcct gctgaataac     120
ttctatccca gagaggccaa agtacagtgg aaggtggata cgccctcca atcgggtaac     180 tcccaggaga gtgtcacaga gcaggacagc aaggacagca cctacagcct cagcagcacc     240
ctgacgctga gcaaagcaga ctacgagaaa cacaaagtct acgcctgcga agtcacccat     300
cagggcctga gctcgcccgt cacaaagagc ttcaacaggg gagagtgtga gagcagctgc     360
gatgtgaaat tggtctgagg atcccccgac ctcgacctct ggct                      404
```

<210> SEQ ID NO 126
<211> LENGTH: 431
<212> TYPE: DNA
<213> ORGANISM: Artificial Sequence
<220> FEATURE:
<223> OTHER INFORMATION: Herceptin VL and hIgk constant region (Km3
      allotype) + a DHVKPKETENTKQPSKSC tail (sequence from human TCRd
      hinge)

<400> SEQUENCE: 126

```
ggccagggca ccaaggtgga gatcaagcgt acggtggctg caccatctgt cttcatcttc      60
ccgccatctg atgagcagtt gaaatctgga actgcctctg ttgtgtgcct gctgaataac     120
ttctatccca gagaggccaa agtacagtgg aaggtggata cgccctcca atcgggtaac     180 tcccaggaga gtgtcacaga gcaggacagc aaggacagca cctacagcct cagcagcacc     240
ctgacgctga gcaaagcaga ctacgagaaa cacaaagtct acgcctgcga agtcacccat     300
cagggcctga gctcgcccgt cacaaagagc ttcaacaggg gagagtgtga tcatgtgaag     360
cctaaagaaa cggagaatac aaaacagccc agtaagagct gttgaggatc cccgacctc     420
```

```
gacctctggc t                                                          431

<210> SEQ ID NO 127
<211> LENGTH: 425
<212> TYPE: DNA
<213> ORGANISM: Artificial Sequence
<220> FEATURE:
<223> OTHER INFORMATION: Herceptin VL and hIgk constant region (Km3
      allotype) + a DVITMDPKDNCSKDAN tail (sequence from human TCRg
      hinge)

<400> SEQUENCE: 127
ggccagggca ccaaggtgga gatcaagcgt acggtggctg caccatctgt cttcatcttc    60
ccgccatctg atgagcagtt gaaatctgga actgcctctg ttgtgtgcct gctgaataac   120
ttctatccca gagaggccaa agtacagtgg aaggtggata acgccctcca atcgggtaac   180
tcccaggaga gtgtcacaga gcaggacagc aaggacagca cctacagcct cagcagcacc   240
ctgacgctga gcaaagcaga ctacgagaaa cacaaagtct acgcctgcga agtcacccat   300
cagggcctga gctcgcccgt cacaaagagc ttcaacaggg gagagtgtga tgtgattact   360
atggacccaa aggataattg cagtaaggac gctaattgag atcccccga cctcgacctc   420 tggct                                                              425

<210> SEQ ID NO 128
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 128

Gly Gly Gly Gly Ser
1               5

<210> SEQ ID NO 129
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 129

Ala Ala Cys Ala Ala
1               5

<210> SEQ ID NO 130
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 130

Gly Gly Gly Gly Ser Cys Ala Ala
1               5

<210> SEQ ID NO 131
<211> LENGTH: 12
```

```
<212> TYPE: PRT
<213> ORGANISM: Artificial sequence
<220> FEATURE:
<223> OTHER INFORMATION: Synthetic polypeptide

<400> SEQUENCE: 131

Gly Gly Gly Gly Ser Ser Gly Gly Gly Ser Ser
1               5                   10

<210> SEQ ID NO 132
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: NON_TER
<222> LOCATION: (1)..(1)

<400> SEQUENCE: 132

Cys Cys Ala Ala
1
```